(12) United States Patent
An et al.

(10) Patent No.: US 11,666,623 B2
(45) Date of Patent: Jun. 6, 2023

(54) TETRAMALEIMIDE LINKERS AND USE THEREOF

(71) Applicant: NewBio Therapeutics, Inc., Shanghai (CN)

(72) Inventors: Deqiang An, Shanghai (CN); Nianhe Han, Shanghai (CN); Peng Zhu, Shanghai (CN); Di Zeng, Shanghai (CN); Baoxiang Wang, Shanghai (CN); Huali Li, Shanghai (CN); Chun Yang, Shanghai (CN)

(73) Assignee: NewBio Therapeutics, Inc., Shanghai (CN)

( * ) Notice: Subject to any disclaimer, the term of this patent is extended or adjusted under 35 U.S.C. 154(b) by 356 days.

(21) Appl. No.: 16/638,624

(22) PCT Filed: Apr. 18, 2018

(86) PCT No.: PCT/CN2018/083515
§ 371 (c)(1),
(2) Date: Feb. 12, 2020

(87) PCT Pub. No.: WO2019/033773
PCT Pub. Date: Feb. 21, 2019

(65) Prior Publication Data
US 2021/0128668 A1    May 6, 2021

(30) Foreign Application Priority Data

Aug. 14, 2017 (CN) .......................... 201710691056.X

(51) Int. Cl.
| | | |
|---|---|---|
| *C07D 207/452* | (2006.01) | |
| *C07D 403/14* | (2006.01) | |
| *C07K 7/06* | (2006.01) | |
| *A61K 38/07* | (2006.01) | |
| *A61K 47/65* | (2017.01) | |
| *A61K 45/00* | (2006.01) | |
| *A61P 29/00* | (2006.01) | |
| *A61P 35/00* | (2006.01) | |
| *A61P 37/00* | (2006.01) | |
| *A61K 47/68* | (2017.01) | |

(52) U.S. Cl.
CPC .............. *A61K 38/07* (2013.01); *A61K 47/65* (2017.08); *A61K 47/6849* (2017.08); *A61K 47/6889* (2017.08); *A61P 35/00* (2018.01); *C07D 403/14* (2013.01)

(58) Field of Classification Search
CPC .... C07D 207/452; C07D 403/14; C07K 7/06; A61K 38/07; A61K 47/65; A61K 47/6849; A61K 47/6889; A61K 47/6803; A61K 45/00; A61K 47/545; A61P 29/00; A61P 35/00; A61P 37/00
See application file for complete search history.

(56) References Cited

U.S. PATENT DOCUMENTS 5,185,433 A    2/1993   Dean et al.

FOREIGN PATENT DOCUMENTS

| WO | 2014114207 A1 | 7/2014 |
| WO | 2016192528 A1 | 12/2016 |

OTHER PUBLICATIONS

Search Report in corresponding International Application No. PCT/CN2018/083515, dated Jul. 24, 2018.

*Primary Examiner* — Brenda L Coleman
(74) *Attorney, Agent, or Firm* — Edell, Shapiro & Finnan, LLC

(57) ABSTRACT

The present invention is directed to tetramaleimide linkers and use thereof, more specifically to the compounds represented by formula I and their use in the preparation of antibody-drug conjugates (ADCs). The ADCs obtained from the tetramaleimide linkers have high homogeneity and stability, and could be used effectively for the treatment of various diseases including tumors. The definition of the groups in formula I is the same as that in the description.

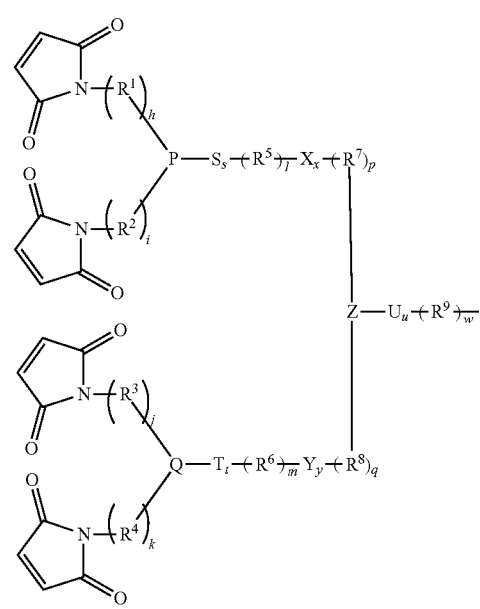

15 Claims, 9 Drawing Sheets

TETRAMALEIMIDE LINKERS AND USE THEREOF

CROSS REFERENCE TO RELATED APPLICATIONS

This application is a National Phase application of International Application No. PCT/CN2018/083515, filed on Apr. 18, 2018, which claims priority under 35 U.S.C. § 119 to Application No. CN 201710691056.X filed on Aug. 14, 2017, the contents of each of which are hereby incorporated by reference in their entireties.

FIELD OF THE INVENTION

The invention relates to novel tetramaleimide linkers, antibody-drug conjugates prepared from these tetramaleimide linkers, and use of the antibody-drug conjugates in the treatment of tumors and other diseases.

BACKGROUND OF THE INVENTION

Antibody-drug conjugates (ADCs) are a kind of novel targeted therapeutic agents for the treatment of cancer and auto-immune diseases. The basic design philosophy originated from the notions of "magic bullet" and "drug targeting", i.e. delivering drugs to the target region via specific carriers, which was firstly proposed by Paul Ehrlich in 1931. However, restricted by the technologies of antibody and high potency cytotoxic drug, the first ADC drug, Mylotarg™, which is for the treatment of acute myleocytic leukemia (AML), was not approved by FDA until 2000. Recently, two ADC drugs were approved by FDA, that is Adcetris™ developed by Seattle Genetics (2011), which is for the treatment of HL/ALCL, and Kadcyla™ developed by Genentech (2013), which is for the treatment of breast cancer. This indicates that the rapid development stage of ADCs for cancer treatment is coming.

ADC is composed of three independent parts, an antibody or antibody-like ligand, high-potency cytotoxic drugs, and linkers that conjugate the drugs to the ligand. The mechanism of action (MOA) of an antibody-drug conjugate is as follows. An antibody or antibody-like ligand specifically recognizes and binds to the cell surface protein receptors (antigens). Once binding to the antigens, the binding complex will be internalized and thus deliver the linked drugs into the cell. The antibody or antibody-like ligand will be digested by enzymes, or the linkers will be cleaved, thereby the high-potency cytotoxic drugs could be released in an active form and kill the cells.

In traditional ADC structures, high-potency cytotoxic drugs are normally linked to the ε-amino group of lysine residues or cysteine residues after full/partial reduction of interchain disulfide bonds via bifunctional linkers. The optimized DAR (Drug/Antibody Ratio) is 2~4. The large number of ε-amino groups of lysine residues (~80/mAb) and the non-selective conjugation mode result in the uncertainty of conjugation sites and conjugated drug numbers, and thus afford ADC product with high heterogeneity. For example, Kadcyla™ with average DAR~3.5 has a DAR distribution ranging from 0 to 8 (Rapid Commun. Mass Spectrom. 2005, 19, 1806-1814). Similarly, when cysteine residues are selected as conjugation sites, although there are only four reducible interchain disulfide bonds in the antibody, they should be partially reduced in order to provide ADCs with optimal average DAR (2~4) (Bioconjugate Chem. 2005, 16, 1282-1290). As existing reducing agents (DTT, TCEP, etc) cannot selectively reduce the interchain disulfide bonds, the conjugation products thus obtained are not homogeneous and contain multi-conjugates with DAR of 0, 2, 4, 6 and 8. Even for a fraction with specific DAR value, it is a mixture that contains conjugates with drugs conjugated at different sites. The heterogeneity of ADC products may ultimately lead to different PK, efficacy, and toxicity properties. For example, the conjugates with higher DAR have been reported, in some cases, to clear more rapidly and contribute to more severe toxicity (Bioconjugate Chem. 2011, 22, 1994-2004).

To overcome the above mentioned shortcomings of traditional linker technologies, new linker technology is highly needed to provide site-specific conjugation products.

SUMMARY OF THE INVENTION

The present invention intends to provide a novel tetramaleimide linker that can be used to produce ADCs via chemical coupling methods, and ADCs prepared via said linkers, as well as their use in the treatment of various diseases including tumors.

Based on extensive research, the inventor developed a novel tetramaleimide linker. This type of linkers incorporates four maleimide groups in its structure, which can simultaneously link to interchain cysteine or other amino acid residues within an antibody. The conjugates obtained from the tetramaleimide linkers and antibodys can have an average DAR of ~2 (i.e. averagely two drugs per antibody), and the DAR2 (2 drugs/antibody) fraction was the main component (90%+). This type of linkers can be widely used for conjugation with most antibodies, such as IgG1, and thus have great application prospect.

In the first aspect, the invention provides a compound of formula I,

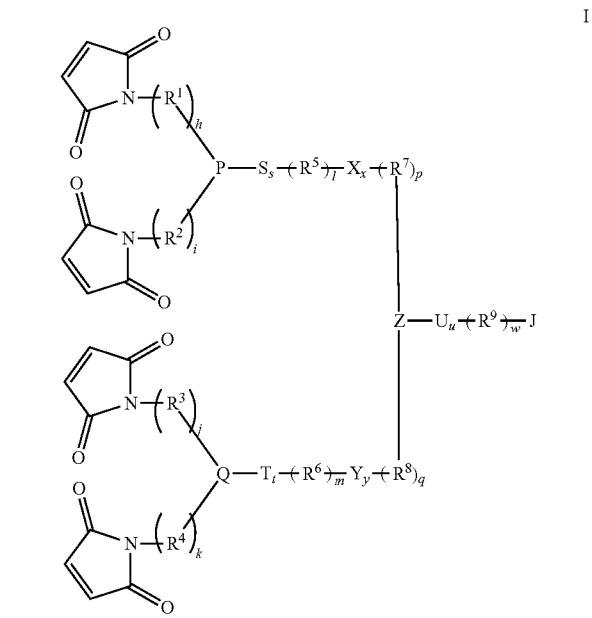

I and pharmaceutically acceptable salt thereof,
wherein
P and Q are each independently selected from $CR^{10}$, N and aryl;

S and T are each independently selected from C=O and O;

X and Y are each independently selected from —C(O)N($R^{11}$)—, —N($R^{12}$)C(O)— and —O—;

Z is selected from $CR^{13}$, N and aryl;

U is selected from C=O and O;

J is selected from —COOH, —OH and —$NHR^{14}$;

h, i, j, k, l, m, p, q, s, t, x, y, u and w are each independently selected from 0 and 1;

$R^1$, $R^2$, $R^3$, $R^4$, $R^5$, $R^6$, $R^7$, $R^8$ and $R^9$ are each independently selected from $C_1$-$C_6$ alkylene, and $C_1$-$C_6$ alkylene containing O in the backbone;

$R^{10}$, $R^{11}$, $R^{12}$, $R^{13}$ and $R^{14}$ are each independently selected from H and $C_1$-$C_6$ alkyl.

In a preferred embodiment, the invention provides a compound of formula I and pharmaceutical acceptable salt thereof, wherein P and Q are each independently selected from $CR^{10}$, N and aryl;

$R^{10}$ is selected from H and $C_1$-$C_6$ alkyl.

In another preferred embodiment, the invention provides a compound of formula I and pharmaceutical acceptable salt thereof, wherein X, and Y are each independently selected from —C(O)N($R^{11}$)—;

X and y are each independently selected from 0 and 1;

$R^{11}$ is selected from H and $C_1$-$C_6$ alkyl.

In another preferred embodiment, the invention provides a compound of formula I and pharmaceutical acceptable salt thereof, wherein Z is selected from $CR^{13}$, N and $C_6$-$C_{10}$ aryl, preferentially phenyl;

$R^{13}$ is selected from H and $C_1$-$C_6$ alky.

In another preferred embodiment, the invention provides a compound of formula I and pharmaceutical acceptable salt thereof, wherein $R^1$, $R^2$, $R^3$ and $R^4$ are each independently selected from $C_1$-$C_6$ alkylene;

h, i, j and k are each independently selected from 0 and 1.

In another preferred embodiment, the invention provides a compound of formula I and pharmaceutical acceptable salt thereof, wherein S and T are each independently selected from C=O and O;

$R^5$ and $R^6$ are each independently selected from $C_1$-$C_6$ alkylene;

l and m are each independently selected from 0 and 1;

s and t are each independently selected from 0 and 1.

In another preferred embodiment, the invention provides a compound of formula I and pharmaceutical acceptable salt thereof, wherein $R^7$ and $R^8$ are each independently selected from $C_1$-$C_6$ alkylene, and $C_1$-$C_6$ alkylene containing O in the backbone;

p and q are each independently selected from 0 and 1.

In another preferred embodiment, the invention provides a compound of formula I and pharmaceutical acceptable salt thereof, wherein U is selected from C=O and O;

$R^9$ is selected from $C_1$-$C_6$ alkylene;

u and w are each independently selected from 0 and 1.

In another preferred embodiment, the invention provides a compound of formula I and pharmaceutical acceptable salt thereof, wherein J is selected from —COOH, OH and $NH_2$.

A typical compound of the invention includes but not limited to:

| Example No. | Structure and Name |
|---|---|
| 1 | 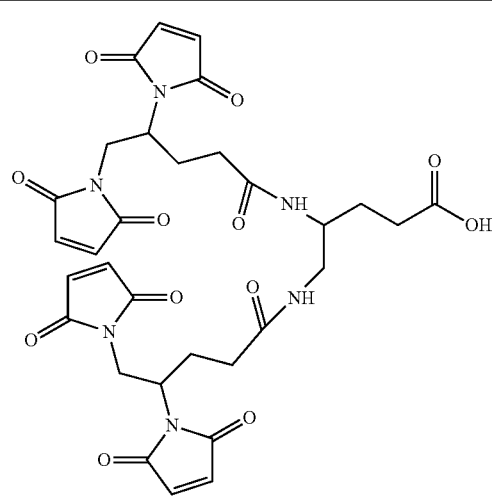<br>1<br>4,5-bis(4,5-bis(2,5-dioxo-2,5-dihydro-1H-pyrrol-1-yl)pentanamido) pentanoic acid |

| Example No. | Structure and Name |
|---|---|
| 2 | 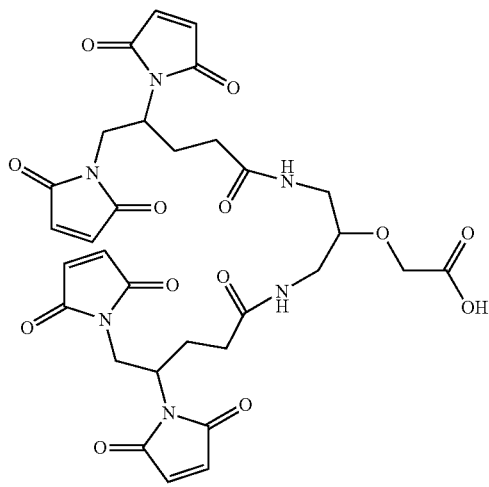<br>2<br>2-(1,3-bis(4,5-bis(2,5-dioxo-2,5-dihydro1H-pyrrol-1-yl)pentanamido)propan-2-yloxy)acetic acid |
| 3 | 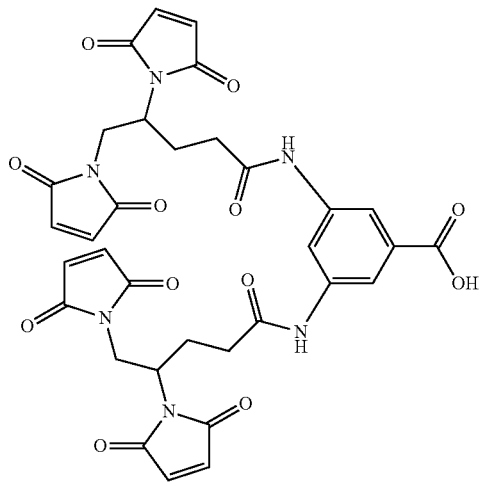<br>3<br>3,5-bis(4,5-bis(2,5-dioxo-2,5-dihydro-1H-pyrrol-1-yl)pentanamido)benzoic acid |

| Example No. | Structure and Name |
|---|---|
| 4 | 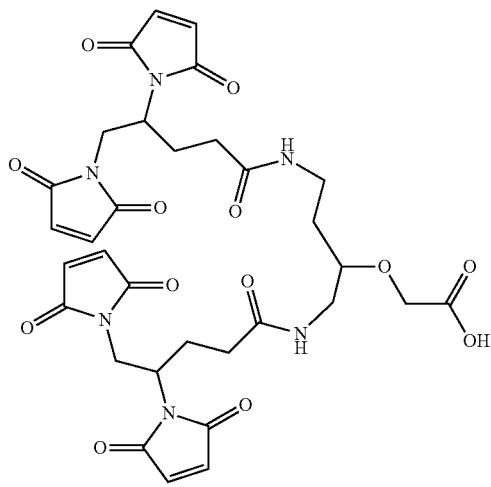<br>4<br><br>2-(1,4-bis(4,5-bis(2,5-dioxo-2,5-dihydro-1H-pyrrol-1-yl)pentan-amido)butan-2-yloxy)acetic acid |
| 5 | 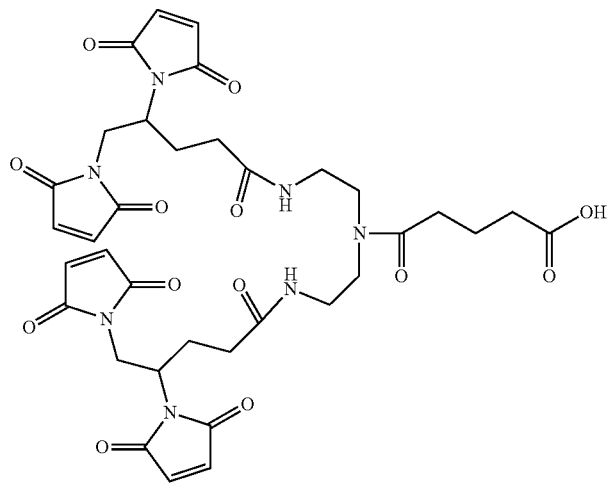<br>5<br><br>5-(bis(2-(4,5-bis(2,5-dioxo-2,5-dihydro-1H-pyrrol-1-yl)pentanamido)ethyl)amino)-5-oxopentanoic acid |

| Example No. | Structure and Name |
|---|---|
| 6 | 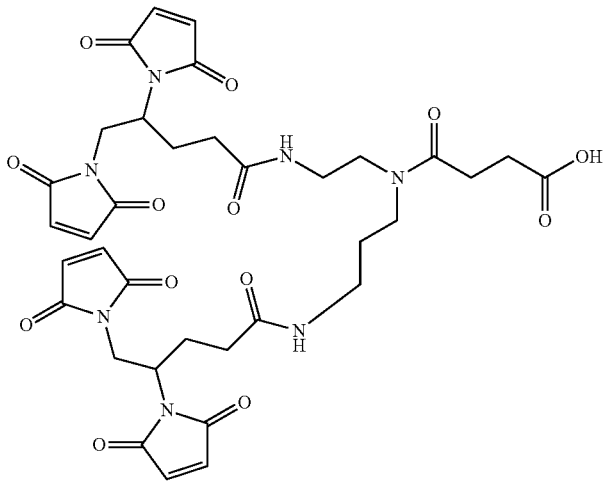<br>6<br><br>4-((2-(4,5-bis(2,5-dioxo-2,5-dihydro-1H-pyrrol-1-yl)pentanamido)ethyl)(3-(4,5-bis(2,5-dioxo-2,5-dihydro-1H-pyrrol-1-yl)pentanamido)propyl)amino)-4-oxobutanoic acid |
| 7 | 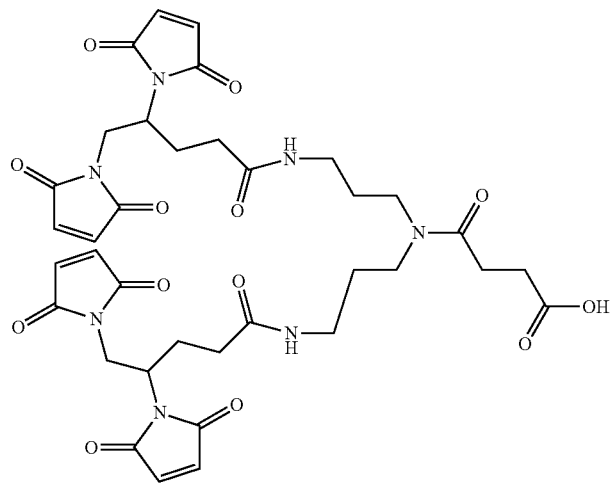<br>7<br><br>4-(bis(3-(4,5-bis(2,5-dioxo-2,5-dihydro-1H-pyrrol-1-yl)pentanamido)propyl)amino)-4-oxobutanoic acid |

| Example No. | Structure and Name |
|---|---|
| 8 | 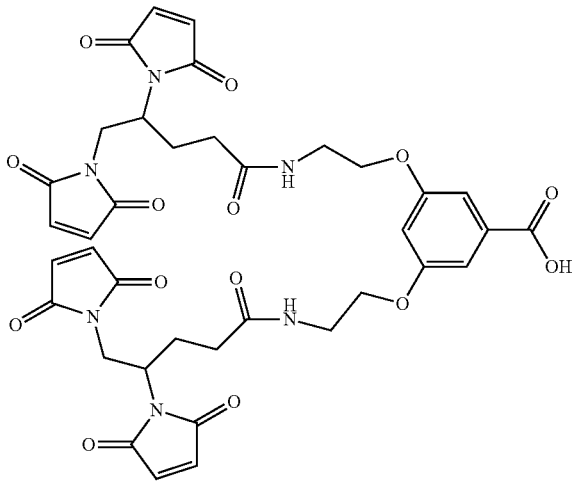<br>3,5-bis(2-(4,5-bis(2,5-dioxo-2,5-dihydro-1H-pyrrol-1-yl)pentanamido)ethoxy)benzoic acid |
| 9 | 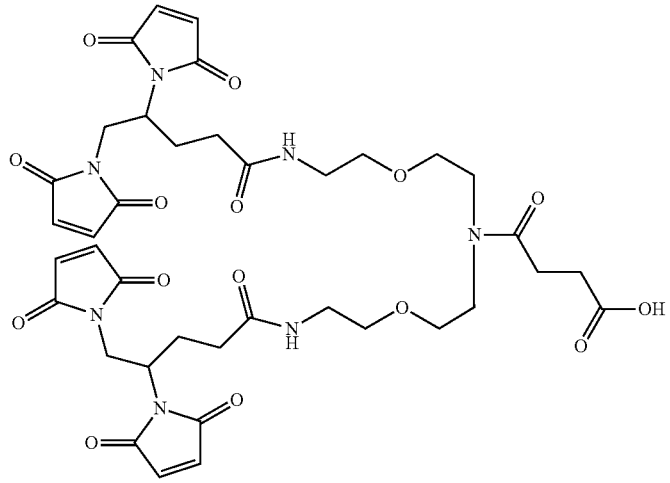<br>4-(bis(2-(2-(4,5-bis(2,5-dioxo-2,5-dihydro-1H-pyrrol-1-yl)pentanamido)ethoxy)ethyl)amino)-4-oxobutanoic acid |

| Example No. | Structure and Name |
|---|---|
| 10 | 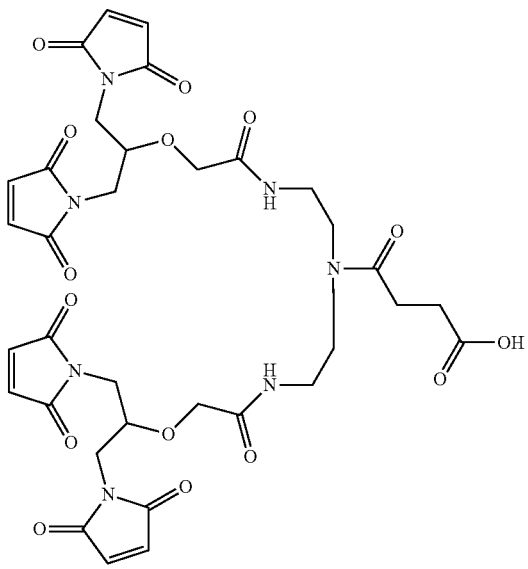<br>10<br>4-(bis(2-(2-(1,3-bis(2,5-dioxo-2,5-dihydro-1H-pyrrol-1-yl)propan-2-yl-oxy)acetamido)ethyl)amino)-4-oxobutanoic acid |
| 11 | 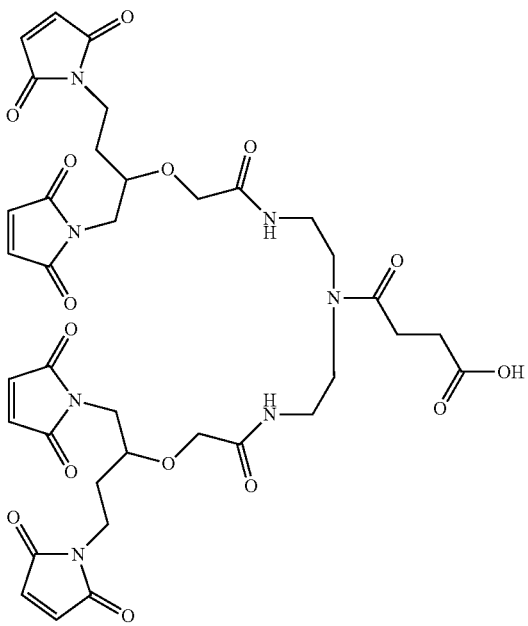<br>11<br>4-(bis(2-(2-(1,4-bis(2,5-dioxo-2,5-dihydro-1H-pyrrol-1-yl)butan-2-yl-oxy)acetamido)ethyl)amino)-4-oxobutanoic acid |

-continued
| Example No. | Structure and Name |
|---|---|
| 12 | 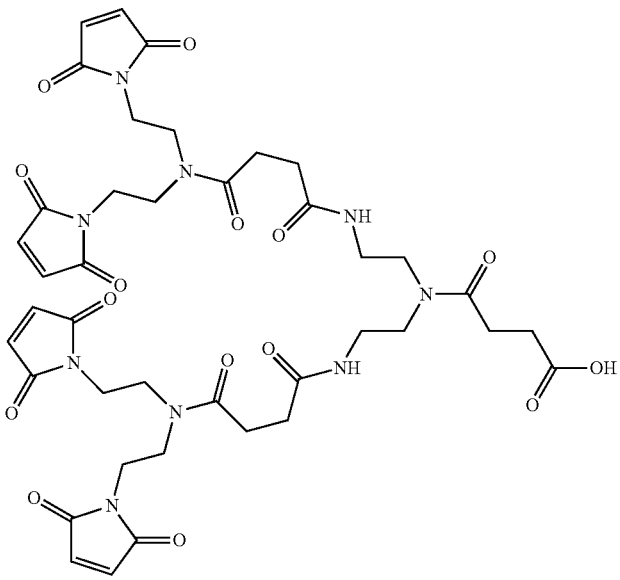
4-(bis(2-(4-(bis(2-(2,5-dioxo-2,5-dihydro-1H-pyrrol-1-yl)ethyl)amino)-4-oxobutanamido)ethyl)amino)-4-oxobutanoic acid |
| 13 | 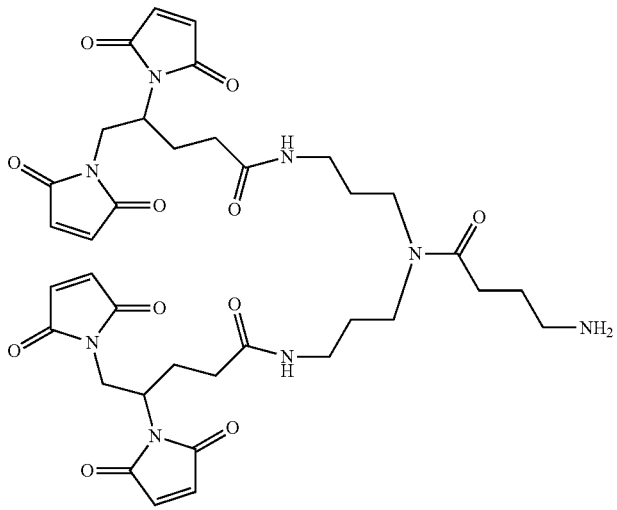
4-(bis(3-(4,5-bis(2,5-dioxo-2,5-dihydro-1H-pyrrol-1-yl)pentanamido)propyl)amino)-4-oxobutylamine |

| Example No. | Structure and Name |
|---|---|
| 14 | 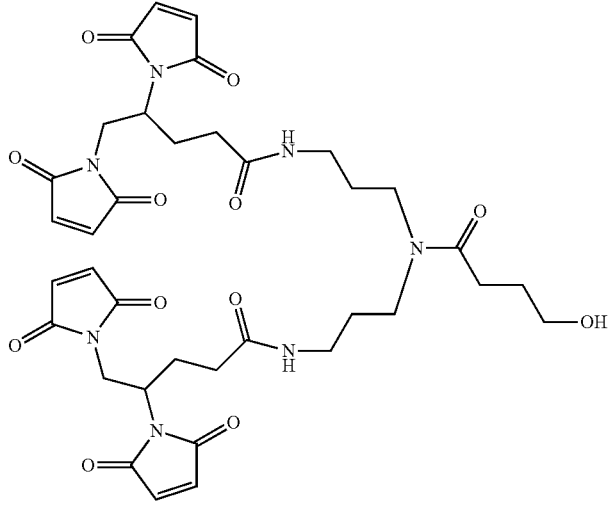<br>14<br>4-(bis(3-(4,5-bis(2,5-dioxo-2,5-dihydro-1H-pyrrol-1-yl)pentanamido)propyl)amino)-4-oxobutanol | or pharmaceutically acceptable salts thereof.

The invention further provides a compound of formula II,

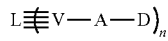

V-A-D    II wherein
- V is a compound of formula I according to the present invention;
- A is optionally other linker;
- D is a drug molecule;
- wherein V is linked to A or D by reaction between a terminal J group of V and a terminal group of A or D.

The invention further provides an antibody-drug conjugate of formula III, $$L \equiv V-A-D)_n \quad \text{III}$$

wherein
- L is an antibody or antibody fragment;
- V is a compound of formula I according to the present invention;
- A is optionally other linker;
- D is a drug molecule;
- n is an integer of 1 to 4;
- wherein V is linked to A or D by reaction between a terminal J group of V and a terminal group of A or D, and is linked to L by reaction between the cysteines or other amino acid residues of L and four maleimide groups.

In a preferred embodiment, the invention provides an antibody-drug conjugate of formula III according to the present invention, wherein A is an optional other linker than tetrameleimide linker, including cleavable and noncleavable linkers.

In another preferred embodiment, the invention provides an antibody-drug conjugate of formula III according to the present invention, wherein A has a formula of C-$E_e$-$F_f$ or $G_g$, wherein
- C is a cleavable linker;
- E and F are self-immolative linkers;
- e and f are each independently selected from an integer of 0 to 5;
- G is a noncleavable linker;
- g is an integer of 0 to 5.

In another preferred embodiment, the invention provides an antibody-drug conjugate of formula III according to the present invention, wherein it is the antibody-drug conjugate of formula IV:

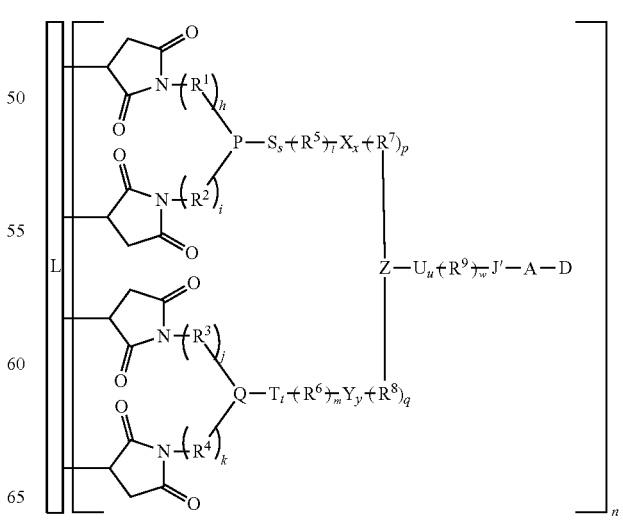

IV wherein

L is an antibody or antibody fragment;

A is optionally other linker than tetramaleimide linker, including cleavable and noncleavable linker;

D is a drug molecule;

Four maleimide groups are simultaneously linked to the same antibody or antibody fragment;

P and Q are each independently selected from $CR^{10}$, N and aryl;

S and T are each independently selected from C=O and O;

X and Y are each independently selected from —C(O)N($R^{11}$)—, —N($R^{12}$)C(O)— and —O—;

Z is selected from $CR^{13}$, N and aryl;

U is selected from C=O and O;

J' is selected from C=O, O and $NR^{14}$;

h, i, j, k, l, m, p, q, s, t, x, y, u and w are each independently selected from 0 and 1;

$R^1$, $R^2$, $R^3$, $R^4$, $R^5$, $R^6$, $R^7$, $R^8$ and $R^9$ are each independently selected from $C_1$-$C_6$ alkylene, and $C_1$-$C_6$ alkylene containing O in the backbone;

$R^{10}$, $R^{11}$, $R^{12}$, $R^{13}$ and $R^{14}$ are each independently selected from H and $C_1$-$C_6$ alkyl.

In another preferred embodiment, the invention provides an antibody-drug conjugate of formula III according to the present invention, wherein the antibody targets cell surface receptors or tumor-related antigens.

In another preferred embodiment, the invention provides an antibody-drug conjugate of formula III according to the present invention, wherein the antibody is IgG1.

In another preferred embodiment, the invention provides an antibody-drug conjugate of formula III according to the present invention, wherein the drug is cytotoxic drug, anti-autoimmune disease drug, or anti-inflammation drug.

The invention further provides a pharmaceutical composition comprising an antibody-drug conjugate of formula III according to the present invention and pharmaceutically acceptable carriers.

The invention further provides the use of the compound of the formula I according to the present invention as linkers in the preparation of antibody-drug conjugates.

The invention further provides the use of an antibody-drug conjugate of formula III according to the present invention, or the pharmaceutical composition comprising the same, in the preparation of drugs for the treatment of cancers, auto-immune diseases and inflammation diseases.

The invention further provides a compound of formula I according to the present invention, for use as a linker in the preparation of antibody-drug conjugates.

The invention further provides an antibody-drug conjugates of formula III according to the present invention, for use as a drug which is prepared for the treatment of cancers, auto-immune diseases or inflammation diseases.

The invention further provides a method for the treatment of cancers, auto-immune diseases or inflammation diseases, comprising administrating to the subject in need of it a therapeutically effective amount of the antibody-drug conjugates of formula III according to the present invention, or the pharmaceutical composition comprising the same.

DETAILED DESCRIPTION OF THE INVENTION

The tetramaleimide linker according to the present invention contains four maleimide groups and a fifth coupling group. The four maleimide groups are used to crosslink the interchain cysteine (after reduction) or other amino acid residues, while the fifth coupling group is used to link small-molecule drug or drug-linker unit, as shown by scheme 1.

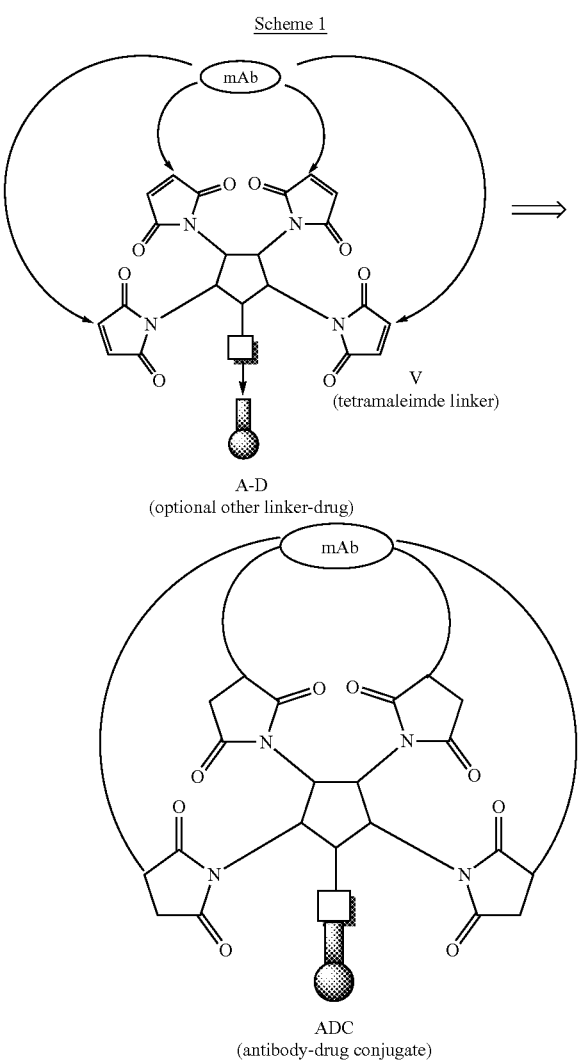

Scheme 1

The ADCs thus obtained can be used to selectively deliver cytotoxic drugs to target cells, for example, tumor cells. The antibody-drug conjugate will bind specifically to the cell surface proteins, and the binding complex will be internalized rapidly by the cells. Once internalized, the cytotoxic drug will be released in certain active form and take effects.

As used herein, the antibody includes chimeric, humanized, or human antibody; antibody fragment that can bind to antigen; or Fc fused protein; or protein.

As used herein, the drug is high-potency cytotoxic drug, including but not limited to, maytansinoids, auristatins, calicheamicins, doxorubicins, CC-1065 and duocarmycins derivatives, PBD dimers, and tubulysins, etc. Under certain conditions, the drug could be poly(ethylene glycol).

The drug itself or drug-linker unit may be conjugated to the antibody via tetramaleimide linkers, producing interchain crosslinked conjugates. Compared to traditional ones, the antibody-drug conjugate provided according to the present invention has much narrower DAR distribution with DAR2 fraction as the main component, and thus greatly improves both structural and pharmacological homogeneities.

Antibody

As used herein, the term "antibody" or "antibody unit" includes within its scope any fragments of an antibody that binds to or reactively associates or complexes with a receptor, antigen or other receptor unit associated with a given target-cell population. An antibody can be any protein or protein-like molecule that binds to, complexes with, or reacts with a moiety of a cell population to be therapeutically or otherwise biologically modified.

Antibody that makes up the ADCs of the invention preferably retains the antigen binding capability of their native, wild type counterparts. Thus, antibodies of the invention are capable of binding, preferably specifically, to antigens. Such antigens include, for example, tumor-associated antigens (TAA), cell surface receptor proteins and other cell surface molecules, cell survival regulatory factors, cell proliferation regulatory factors, molecules associated with tissue development or differentiation (e.g., known or suspected to contribute function), lymphokines, cytokines, molecules involved in cell cycle regulation, molecules involved in vasculogenesis and molecules associated with angiogenesis (for e.g. known or suspected to contribute function). The tumor-associated antigen may be a cluster differentiation factor (i.e., a CD protein). Antigens that bind to the antibodies of the present invention may be one or a subset of the above categories, wherein the other subset(s) of said category comprise other molecules/antigens that have a distinct characteristic (with respect to the antigen of interest).

Antibodies used in ADCs include, but not limited to, antibodies against cell surface receptors and tumor-associated antigens (TAA). Such tumor-associated antigens are well known in the art, and can be prepared according to the methods or information which is well known in the art for the preparation of antibodies. In order to develop effective cellular targets that can be used in the diagnosis and treatment for cancer, the researchers sought to find transmembrane or otherwise tumor-associated polypeptides that are specifically expressed on the surface of one or more particular type(s) of cancer cell as compared to the other one or more normal non-cancerous cell(s). Often, such tumor-associated polypeptides are more abundantly expressed on the surface of the cancer cells as compared to the non-cancerous cells. The identification of such tumor-associated factors can greatly enhance the specific targeting properties of antibodies based cancer therapy.

Examples of TAA include, but are not limited to, Tumor-Associated Antigens (1)-(36) listed below. For convenience, information relating to these antigens, all of which are known in the art, is listed below and includes names, alternative names, Genbank accession numbers. Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or exhibit substantially the same biological properties or characteristics as a TAA having a sequence found in the cited references.

Tumor-Associated Antigens (1)-(36):
(1) BMPR1B (bone morphogenetic protein receptor-type IB, Genbank accession no. NM_001203);
(2) E16 (LAT1, SLC7A5, Genbank accession no. NM_003486);
(3) STEAP1 (six transmembrane epithelial antigen of prostate, Genbank accession no. NM_012449);
(4) 0772P (CA125, MUC16, Genbank accession no. AF361486);
(5) MPF (MPF, MSLN, SMR, megakaryocyte potentiating factor, mesothelin, Genbank accession no. NM_005823);
(6) Napi3b (NAPI-3B, NPTIIb, SLC34A2, solute carrier family 34 (sodium phosphate) member 2, type II sodium-dependent phosphate transporter 3b, Genbank accession no. NM_006424);
(7) Sema 5b (FLJ10372, KIAA1445, Mm.42015, SEMA5B, SEMAG, Semaphorin 5b H log, sema domain, seven thrombospondin repeats (type 1 and type 1-like), transmembrane domain (TM) and short cytoplasmic domain, (semaphorin) 5B, Genbank accession no. AB040878);
(8) PSCA hlg (2700050C12Rik, C530008016Rik, RIKEN cDNA 2700050C12, RIKEN cDNA 2700050C12 gene, Genbank accession no. AY358628);
(9) ETBR (Endothelin type B receptor, Genbank accession no. AY275463);
(10) MSG783 (RNF124, hypothetical protein FLJ20315, Genbank accession no. NM_017763);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);
(12) TrpM4 (BR22450, FLJ20041, TRPM4, TRPM4B, transient receptor potential cation channel, subfamily M, member 4, Genbank accession no. NM_017636);
(13) CRIPTO (CR, CR1, CRGF, CRIPTO, TDGF1, teratocarcinoma-derived growth factor, Genbank accession no. NP_003203 or NM_003212;
(14) CD21 (CR2 (Complement receptor 2) or C3DR (C3d/Epstein Barr virus receptor) or Hs. 73792, Genbank accessionno. M26004);
(15) CD79b (CD79B, CD79β, IGb (immunoglobulin associated beta), B29, Genbank accession no. NM_000626);
(16) FcRH2 (IFGP4, IRTA4, SPAP1A (SH2 domain containing phosphatase anchor protein 1a), SPAP1B, SPAP1C, Genbank accession no. NM_030764);
(17) HER2 (ErbB2, Genbank accession no. M11730);
(18) NCA (CEACAM6, Genbank accession no. M18728);
(19) MDP (DPEP1, Genbank accession no. BC017023);
(20) IL20Rα (IL20Ra, ZCYTOR7, Genbank accession no. AF184971);
(21) Brevican (BCAN, BEHAB, Genbank accession no. AF229053);
(22) EphB2R (DRT, ERK, Hek5, EPHT3, Tyro5, Genbank accession no. NM_004442);
(23) ASLG659 (B7h, Genbank accession no. AX092328);
(24) PSCA (Prostate stem cell antigen precursor, Genbank accession no. AJ297436);
(25) GEDA (Genbank accession no. AY260763);
(26) BAFF-R (B-cell activating factor receptor, BLys receptor 3, BR3, Genbank accession no. AF116456);
(27) CD22 (B-cell receptor CD22-β form, Genbank accession no. AK026467);
(28) CD79a (CD79A, CD79α, immunoglobulin-associated alpha, a B-cell specific protein that covalently interacts with Ig beta (CD79B) and forms a complex on the surface with Ig M molecules, transduces a signal involved in B-cell differentiation, Genbank accession No. NP-001774.1);

(29) CXCR5 (Burkitt's lymphoma receptor 1, a G protein-coupled receptor that is activated by the CXCL13 chemokine, plays a role in lymphocyte migration and humoral defense, plays a role in HIV-2 infection and perhaps development of AIDS, lymphoma, myeloma, and leukemia, Genbank accession No. NP_001707.1);

(30) HLA-DOB (Beta subunit of MHC class II molecule (Ia antigen) that binds peptides and presents them to CD4+ T lymphocytes, Genbank accession No. NP_002111.1);

(31) P2X5 (Purinergic receptor P2X ligand-gated ion channel 5, an ion channel gated by extracellular ATP, may be involved in synaptic transmission and neurogenesis, its deficiency may contribute to the pathophysiology of idiopathic detrusor instability, Genbank accession No. NP_002552.2);

(32) CD72 (B-cell differentiation antigen CD72, Lyb-2, Genbank accession No. NP_001773.1);

(33) LY64 (lymphocyte antigen 64 (RP105), type I membrane protein family which is rich in leucine repeat (LRR), regulates B-cell activation and apoptosis, loss of function is associated with increased disease activity in patients with systemic lupus erythematosis, Genbank accession No. NP_005573.1);

(34) FcRH1 (Fc receptor-like protein 1, a putative receptor for the immunoglobulin Fc domain that contains C2 type Ig-like and ITAM domains, may play a role in B-lymphocyte differentiation, Genbank accession No. NP_443170.1);

(35) IRTA2 (Translocation-related immunoglobulin superfamily receptor 2, a putative immunoreceptor with possible roles in B cell development and lymphomagenesis; gene disorder caused by translocation occurs in certain B-cell malignancies, Genbank accession No. NP_112571.1);

(36) TENB2 (putative transmembrane proteoglycan, related to the EGF/heregulin family of growth factors and follistatin, Genbank accession No. AF179274).

Drug

As used herein, the term "drug" or "D" refers to any compound possessing a desired biological activity and having a reactive functional group that may be used to incorporate the drug into the conjugate of the invention. The desired biological activity includes diagnosis, cure, alleviation, treatment, or prevention of disease in human or other animals. Thus, so long as it has the necessary reactive functional group, the term "drug" refers to the drugs recognized by the official United States Pharmacopeia, official Homeopathic Pharmacopeia of the United States, official National Formulary, or any supplement thereof. Exemplary drugs are set forth in the Physician's Desk Reference (PDR) and in the Orange Book maintained by the U.S. Food and Drug Administration (FDA). New drugs are continually being discovered and developed, and the present invention provides that these new drugs may also be incorporated into the prodrugs of the present invention.

Preferably, the drug is a cytotoxic drug useful in cancer therapy; a protein or polypeptide possessing a desired biological activity, such as a toxin, e.g., abrin, ricin A, *Pseudomonas* exotoxin, and diphtheria toxin; other suitable proteins including tumor necrosis factor, α-interferon, β-interferon, nerve growth factor, platelet derived growth factor, tissue plasminogen activator, and biological response modifiers, such as lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In one aspect, the drugs are maytansine or maytansinoids. Maytansine inhibits cell proliferation by inhibiting the formation of microtubules of the microtubulin protein (Science 1975, 189, 1002-1005; U.S. Pat. No. 5,208,020). Maytansinoids are derivatives of maytansine. Both maytansine and maytansinoids are highly cytotoxic, but their clinical use in cancer therapy has been greatly limited due to poor selectivity for tumors. However, the high cytotoxic potency enables them to be attractive drug moieties in ADCs. The structures shown below are maytansine, maytansinoids, and three representative maytansinoids commonly used in ADC:

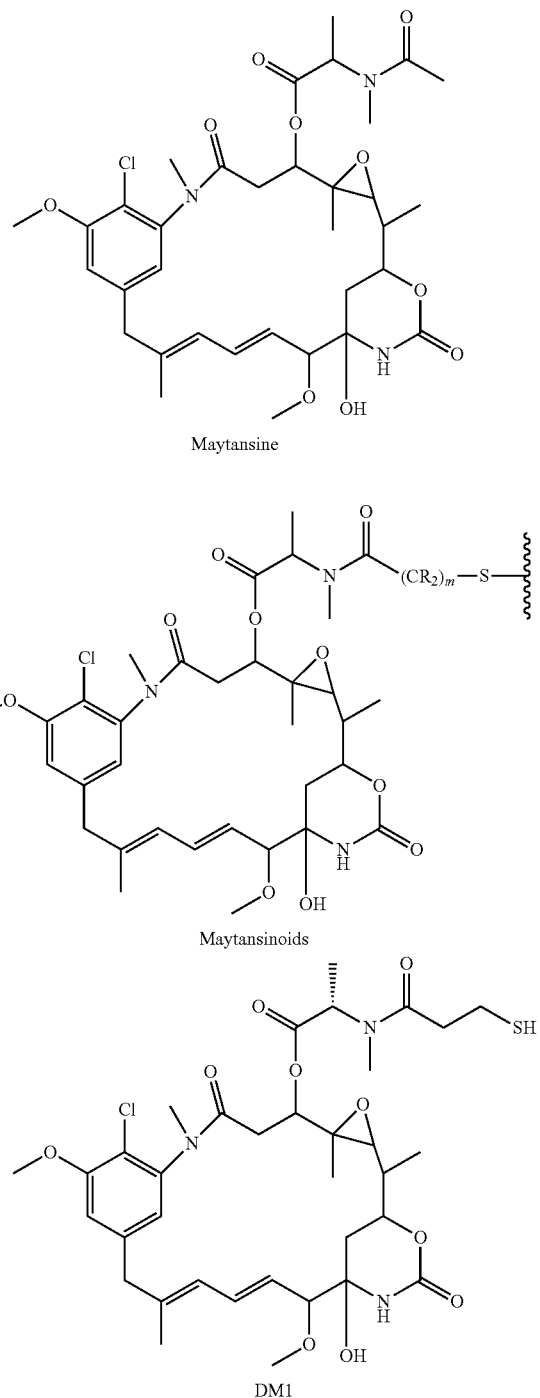

25

-continued

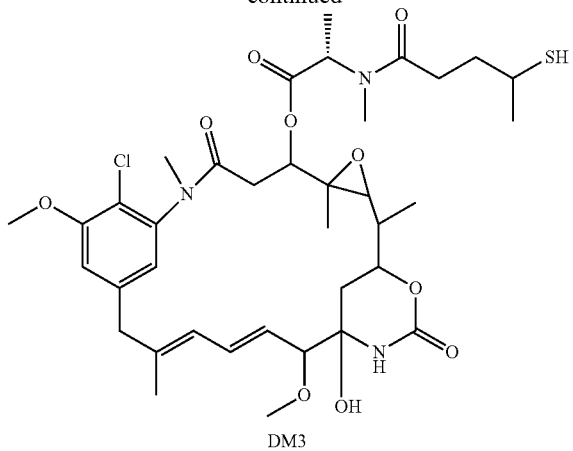

DM3

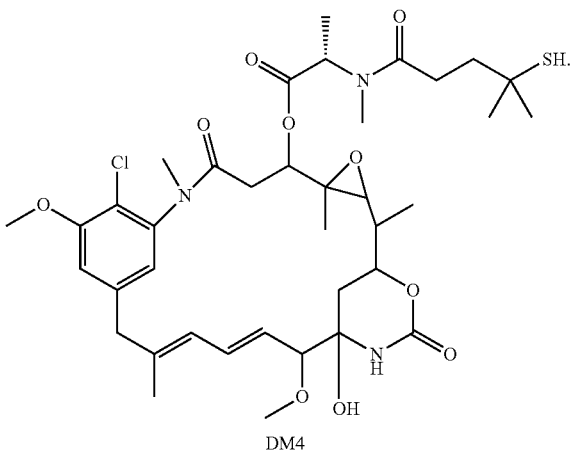

DM4

The main raw material for preparing maytansinoids is maytansinol, which is mainly obtained from ansamitocins hydrolysis. Ansamitocins could be accessibly produced by fermentation. Ansamitocin derivatives (WO 2012/061590) and alaninyl maytansinol (US 2012/0121615) are also reported to be good candidates as ADC "warheads".

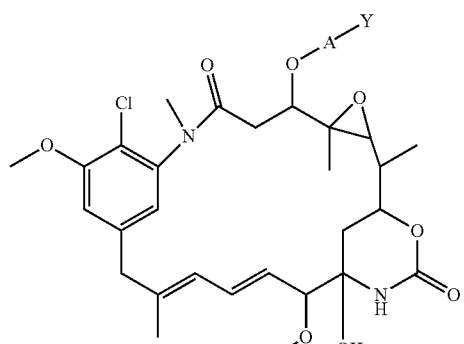

A is C=O, (C=O)NR', and (C=O)O
Y is a substituent group
Ansamitocin derivatives

26

-continued

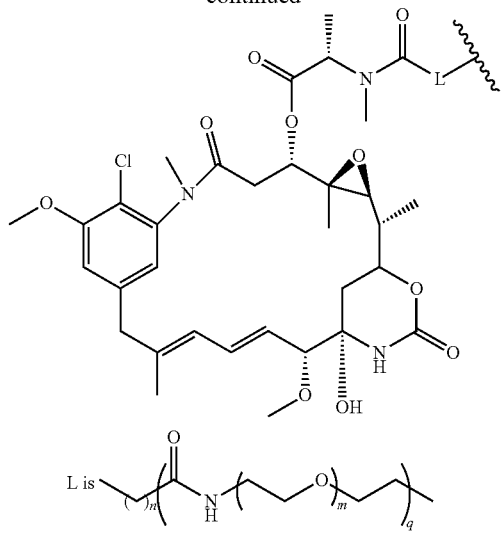

L is

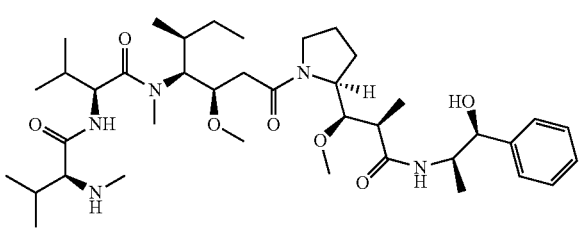

Alaninyl maytansinol

In another aspect, the drugs are auristatins. Auristatins are synthetic analogues of Dolastatin 10, which was biologically active polypeptide isolated from the marine mollusk *Dolabella auricularia*(U.S. Pat. No. 7,498,298). Dolastatin 10 is an agent that inhibits tubulin polymerization by binding to the same domain on tubulin as the anticancer drug vincristine. Dolastitin 10, auristatin PE, and auristatin E are all linear peptides having four amino acids, three of which are unique to the dolastatins, and a C-terminal amide. Two representative auristatins, monomethyl auristatin E (MMAE) and monomethyl auristatin F (MMAF), are preferred drug moiety candidates for ADCs.

MMAE

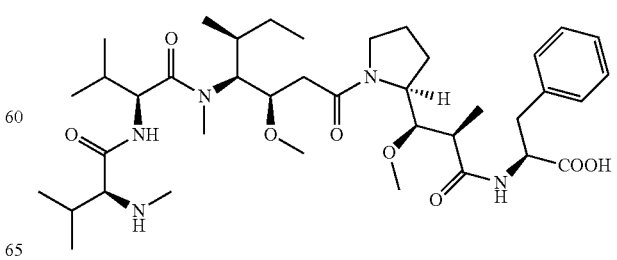

MMAF

In another aspect, the drugs are tubulysins. Tubulysins are natural products first isolated from myxobacterial culture, which are potent cell growth inhibitor that act by inhibiting tubulin polymerization, and among which Tubulysin D is the most potent. Tubulysin D is a complex tetrapeptide, and unstable in both acidic or basic conditions due to the o-acyl/N,O-acetal functional groups. US 2011/0021568 and US 2013/0224228 disclosed a series of tubulysin analogs respectively, which remove the unstable groups from the structure and have high cytotoxic potency.

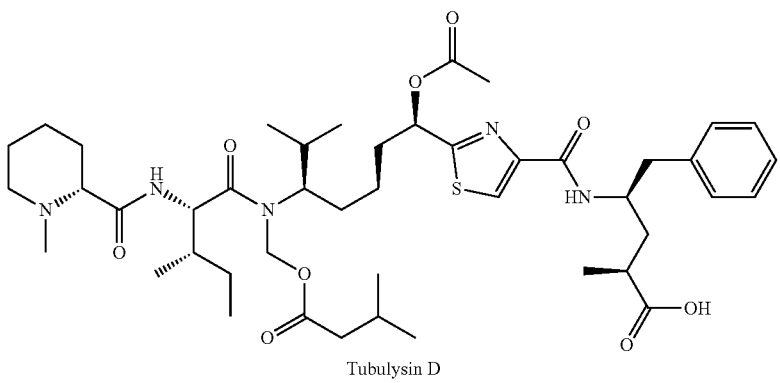

Tubulysin D

In another aspect, the drugs are calicheamicins. Calicheamicins are antitumor antibiotics that bind to the minor groove of DNA to promote double-stranded DNA cleavage at a specific site, thus causing cell death. Calicheamicins are potent at sub-picomolar concentrations in vitro, but their low therapeutic index precluded further clinical development. The high potency, however, makes them good candidates for ADCs (such as Gemtuzumab Ozogamicin and Inotuzumab Ozogamicin).

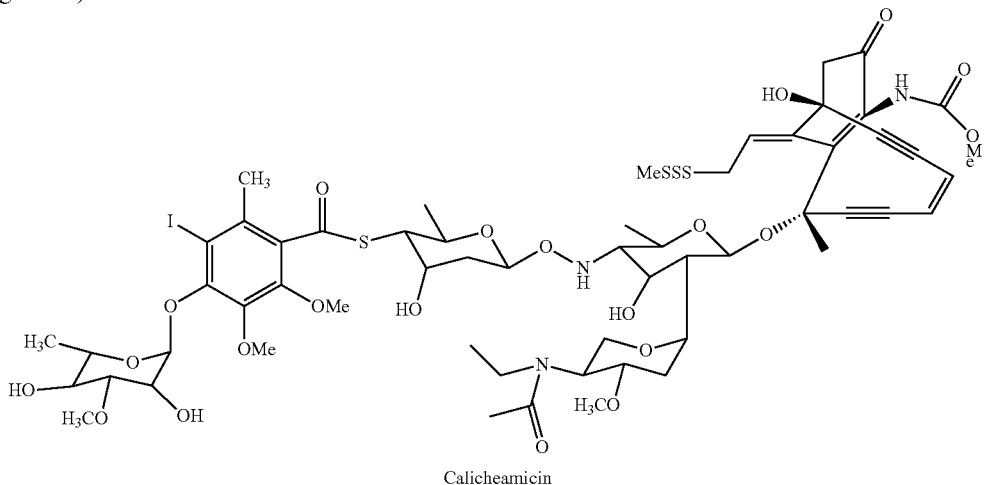

Calicheamicin

In another aspect, the drugs are doxorubicins. Doxorubicin is an intercalating agent that embeds DNA double helix structure to block DNA replication and is used as chemotherapeutic agent. Due to the relative low potency of doxorubicin ($IC_{50}$ of 0.1-0.2 µM for human carcinoma lines, whereas subnanomolar activities are now typically seen for ADC payloads), application of doxorubicin as ADC drug moiety is not popular.

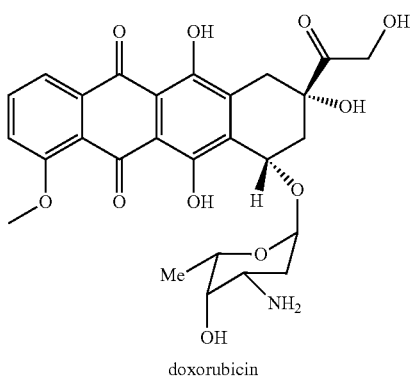 [SMILES: COc1cccc2c1C(=O)c1c(O)c3c(c(O)c1C2=O)C[C@@](O)(C(=O)CO)C[C@@H]3OC1CC(N)C(O)C(C)O1]

doxorubicin

In another aspect, the drugs are duocarmycins, CC-1065 and other cyclopropapyrroloind-4-one (CPI) derivatives,

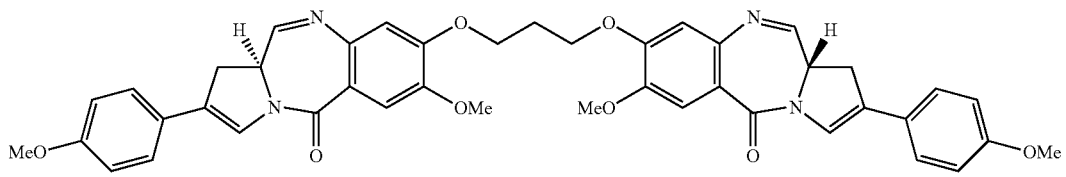

SG2201

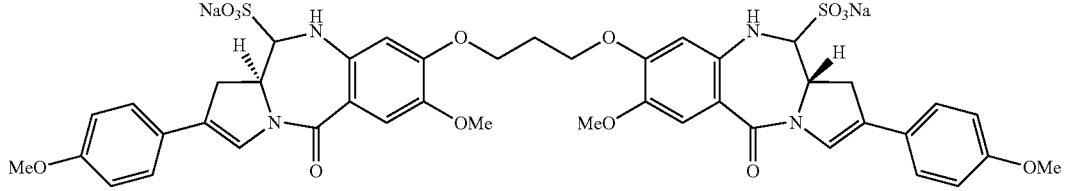

SG2285 which are potent minor-groove binding DNA alkylating agents. Cyclopropabenzindol-4-one analogues (CBI) are chemically more stable, biologically more potent, and synthetically more accessible than their parent compounds comprising the nature CPI alkylating subunit. One representative CBI derivative is the phenolic hydroxyl group-protected CBI (see the formula below), which has decreased prodrug toxicity and improved water solubility.

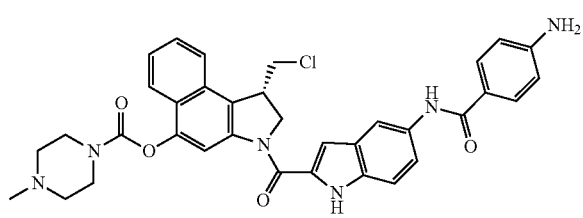 [SMILES: CN1CCN(C(=O)Oc2cc3c(c4ccccc24)[C@H](CCl)CN3C(=O)c2cc3cc(NC(=O)c4ccc(N)cc4)ccc3[nH]2)CC1]

In another aspect, the drugs are pyrrolo[2,1-c][1,4]benzodiazepines (PBDs) or PBD dimers. The pyrrolo[2,1-c][1,4]benzodiazepines (PBDs) are natural products produced by Streptomyces species with the unique characteristic of forming nondistortive covalent adducts in the minor groove of DNA, specifically at the purine-guanine-purine sequences. There is a growing interest in using PBDs as part of a small-molecule strategy for targeting DNA sequences and also as novel anticancer and antibacterial agents (Biochemistry 2008, 47, 11818-11829). The biological activity of these molecules can be potentiated by Joining two PBD units together through their C8/C8-hydroxyl groups via a flexible alkylene linker (WO 2011/130616). The PBD dimers are thought to form sequence-selective DNA lesions such as the palindromic 5'-Pu-GATC-Py-3' interstrand cross-link, which mainly accounts for their biological activity. These compounds have been shown to be highly useful cytotoxic agents and good candidates as ADC warheads.

In another aspect, the drugs are not limited to above-mentioned categories and also include all drugs that could be used in ADCs.

Linker

As used herein, the term "linker" or "ADC linker" refers to a bifunctional or multifunctional molecule that can react with a protein/antibody and a drug respectively, and thus link the protein/antibody to the drug as a "bridge". According to drug release mechanism in cells, "linker" or "ADC linker" could be classified into two categories: noncleavable linker and cleavable linker.

Noncleavable linker is a kind of relatively stable linker, which is difficult to be cleaved under in vivo conditions. For ADCs with noncleavable linkers, the release mechanism is believed to occur via internalization of the ADC followed by degradation of the mAb component in the lysosome, resulting in the release of the small molecular drug still attached via the linker to an antibody amino acid residue. The chemical modification of the drug didn't diminish its cytotoxic potential. This form of the drug is, however, charged (amino acid residue) and presumably hard to diffuse into neighboring cells. Hence, it can't kill adjacent tumor cells (bystander effects) that don't express the target antigen (antigen-negative cells) (Bioconjugate Chem. 2010, 21, 5-13). Some common linkers, such as MC linker, MCC linker, etc., are shown as below:

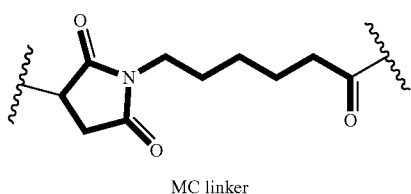

MC linker

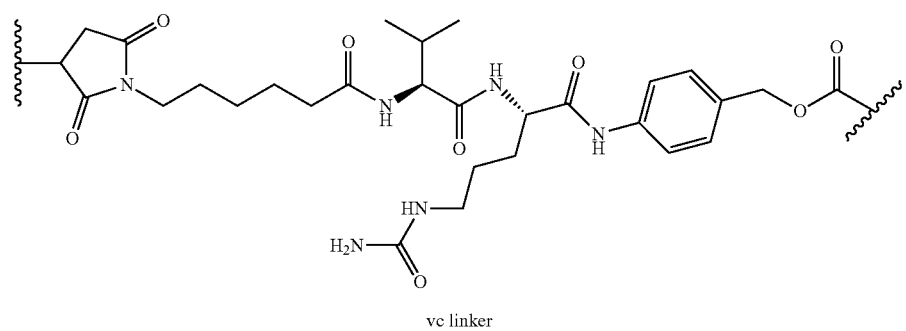 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

vc linker

-continued

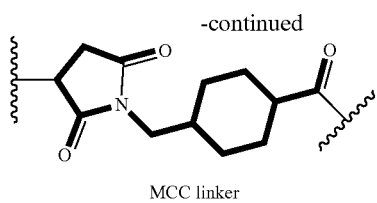

MCC linker

Cleavable linkers, as the name implies, could be cleaved within the target cells to release the active drugs (small molecule drugs themselves). Cleavable linkers can be categorized into two main groups: chemically labile and enzyme-labile linkers.

Chemically labile linkers could be selectively cleaved according to the properties of the plasma and cytoplasm. Such properties include pH value, glutathione concentration, etc.

For pH sensitive linkers, generally called acid-cleavable linker, the linkers are relatively stable in the neutral environment (pH 7.3-7.5) of blood, but will undergo hydrolysis in the mildly acidic endosomes (pH 5.0-6.5) and lysosomes (pH 4.5-5.0). Most of the linkers, such as hydrozones, carbonates, acetals, ketals, were used for the first generation of ADCs. However, due to the limited plasma stability of the acid-cleavable linkers, the ADCs based on this kind of linkers have relatively short half-life (2-3 days). The shortened half-lives preclude the application of pH-sensitive linkers in the new generations of ADCs to a certain degree.

For glutathione-sensitive linkers, generally called disulfide linkers, the release is attributed to the high intracellular concentration in the cytoplasma (millimolar range) versus the relatively low concentration in the blood (micromolar range) of glutathione. This is especially true for tumor cells, where the hypoxic state results in enhanced activity of reductive enzymes and thus even higher glutathione concentrations. Disulfide bonds are thermodynamically stable and thus provide good stability in plasma.

Enzyme-labile linkers, such as peptide linkers, are alternative approaches to achieve better control of the drug release. The peptide linkage will be effectively cleaved by lysosomal proteases, such as cathepsin B or plasmin (elevated levels in certain tumor tissues). Such peptidic linkages are deemed stable in plasma circulation, as proteases are usually not extracellularly active due to the extracellular unfavorable pH and the serum protease inhibitors. In view of the high plasma stability and good intracellular cleaving selectivity and efficiency, enzyme-labile linkers are broadly selected as cleavable linker candidates in ADCs. Typical enzyme-labile linkers include Val-Cit (vc), etc.

Self-immolative linker is generally sited between cleavable linker and cytotoxic drug, or is part of a cleavable linker itself. The working mechanism of self-immolative linker is that it can undergo self-structural rearrangement to release the linked active drug when the cleavable linker was cut by protease. Typical self-immolative linkers include p-aminobenzyl alcohol (PAB), etc.

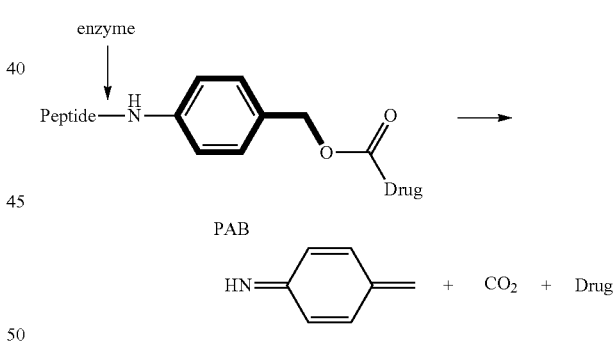

PAB

Antibody-Drug Conjugate

The antibody-drug conjugate according to the present invention is composed of antibody, tetramaleimide linker, optional other linker, and drug. The optional other linker is referred to cleavable linker or non-cleavable linker.

Antibodies are comprised of globular proteins, which have an array of amino acids linkage sites that can be used to conjugate drug-linker unit. Due to their tertiary and quaternary structure, only solvent-accessible amino acid residues can be conjugated. In practice, high-yielding conjugations usually occur on the ε-amino group of lysine residues or the sulfhydryl group of cysteine residues.

The abundance of lysine side-chains at the antibody surface provide multiple linkage sites for conjugation, which leads to a mixture of ADCs with different payload numbers (DARs) and conjugation sites.

Compared to the ones traditionally made, the ADCs prepared according to the present invention not only have the average DAR around 2, residing in the optimized ADC DAR range of 2-4, but also have much narrower DAR distribution, with the DAR2 fraction being the main component (more than 90%). In addition, the conjugation products don't contain naked antibody (DAR=0), which has no cell killing effect. Also, the conjugation products don't contain heavily conjugated antibody (for example DAR>6), which is cleared more rapidly than those with low DAR numbers. As a result, the ADC products provided according to the present invention show much improved homogeneity.

Definition

Unless otherwise stated, the terms used in the specification and claims have the meanings described below.

"Alkyl" refers to a saturated straight or branched aliphatic hydrocarbon group including 1-20 carbon atoms. Preferably, an alkyl group is an alkyl having 1 to 12 carbon atoms, more preferably 1 to 10 carbon atoms, and most preferably an alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and isomers of branched chains thereof. More preferably, an alkyl group is a lower alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When substituted, the substituent group(s) can be substituted at any available connection point, and preferably the substituent group(s) is one or more groups independently selected from the group consisting of alkyl, alkenyl, alkynyl, alkyloxyl, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, oxo group.

"Alkylene" means an alkyl group as defined above wherein one of the hydrogen atoms is further removed to form a divalent group. Representative examples include, but are not limited to, methylene (—$CH_2$—), ethylene (—$(CH_2)_2$—), propylene (($CH_2)_3$—), butylene (—$(CH_2)_4$—), and the like.

"Alkenyl" refers to an alkyl group as defined above consisting of at least two carbon atoms and at least one carbon-carbon double bond, for example vinyl, 1-propenyl, 2-propenyl, 1-, 2- or 3-butenyl and the like. The alkenyl group may be substituted or unsubstituted, and when substituted, the substituent group(s) can be substituted at any available connection point, and preferably one or more groups independently selected from the group consisting of alkyl, alkenyl, alkynyl, alkoxy, alkylthio, alkylamino, halogen, mercapto, hydroxy, nitro, cyano, cycloalkyl, heterocloalkyl, aryl, heteroaryl, cycloalkoxy, heterocycloalkoxy, cycloalkylthio, heterocycle alkylthio.

"Alkynyl" refers to an alkyl group as defined above consisting of at least two carbon atoms and at least one carbon-carbon triple bond, for example ethynyl, propynyl, butynyl and the like. The alkynyl group may be substituted or unsubstituted, and when substituted, the substituent group(s) can be substituted at any available connection point, and preferably one or more groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycle alkylthio.

"Alkenylene" is an unsaturated linear, branched or carbocyclic ring hydrocarbon group containing two monovalent radical centers due to the removal of two hydrogen atoms on the same or two different carbon atoms of the parent alkene. Representative examples include, but are not limited to, vinylene (—CH=CH—), 1,3-propenylene (—$CH_2$CH=CH—), and the like.

"Alkynylene" is an unsaturated linear, branched or carbocyclic ring hydrocarbon group containing two monovalent radical centers due to the removal of two hydrogen atoms on the same or two different carbon atoms of the parent alkyne. Representative examples include, but are not limited to, ethynylene (—CH≡CH—), 1,3-propynyl (—$CH_2$C≡CH—), and the like.

"Arylene" refers to an aromatic hydrocarbon group of 6 to 12 carbon atoms comprising two monovalent radical centers due to the removal of two hydrogen atoms from two different carbon atoms of the parent aromatic ring system. Representative examples include, but are not limited to, 1,2-Phenylene, 1,3-phenylene, 1,4-phenylene and the like.

"Cycloalkyl" refers to a saturated and/or partially unsaturated monocyclic or polycyclic hydrocarbon group having 3 to 20 carbon atoms, preferably 3 to 12 carbon atoms, more preferably 3 to 10 carbon atoms, and most preferably 3 to 8 carbon atoms. Unlimited examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more rings may contain one or more double bonds, but none of the rings has a completely conjugated pi-electron system, preferably 6 to 14 membered spiro cycloalkyl, and more preferably 7 to 10 membered spiro cycloalkyl. According to the number of the common spiro atoms, spiro cycloalkyl may be divided into mono-spiro cycloalkyl, di-spiro cycloalkyl, or poly-spiro cycloalkyl, and preferably a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Unlimited examples of spiro cycloalkyls include, but are not limited to:

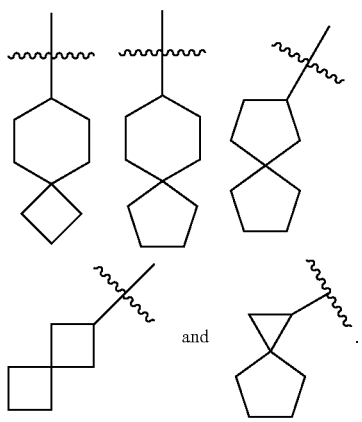

"Fused cycloalkyl" refers to a 5 to 20 membered full-carbon polycyclic group, wherein each ring in the system shares an adjacent pair of carbon atoms with another ring, wherein one or more rings may contain one or more double bonds, but none of the rings has a completely conjugated pi-electron system, preferably 6 to 14 membered fused cycloalkyl, more preferably 7 to 10 membered fused cycloalkyl. According to the number of membered rings, fused cycloalkyl may be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Unlimited examples of fused cycloalkyl include, but are not limited to:

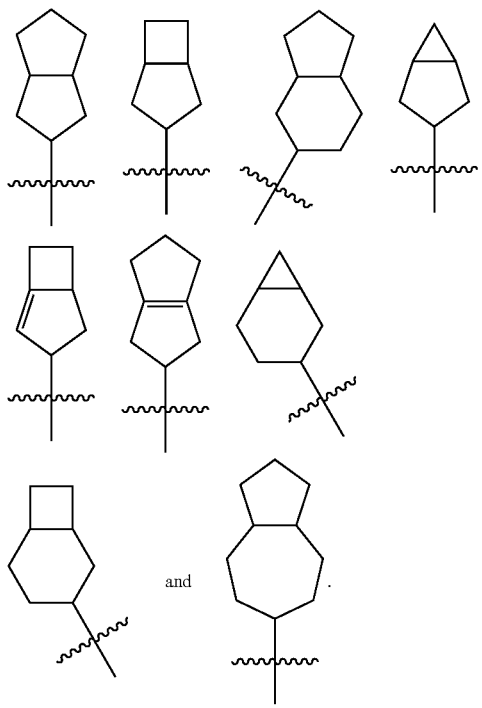

"Bridged cycloalkyl" refers to a 5 to 20 membered full-carbon polycyclic group, wherein every two rings in the system share two disconnected atoms, wherein the rings may have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl may be divided into bicyclic, tricyclic, tetracyclic or polycyclic bridged cycloalkyl, and preferably bicyclic, tricyclic or tetracyclic bridged cycloalkyl, and more preferably bicyclic or tricyclic bridged cycloalkyl. Unlimited examples of bridged cycloalkyls include, but are not limited to:

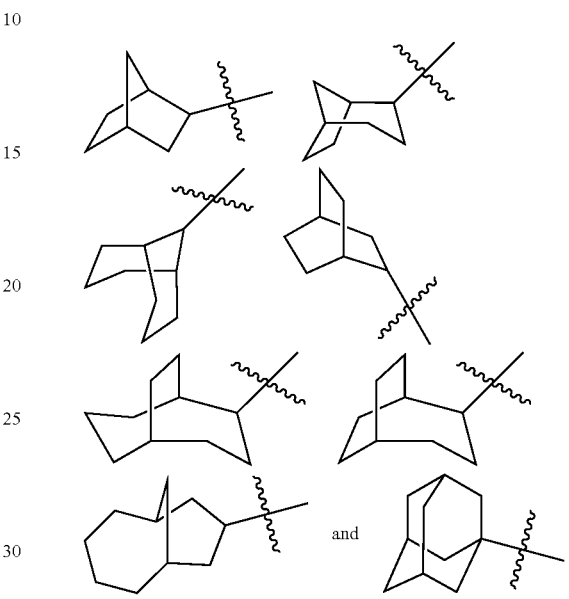

Said cycloalkyl can be fused to aryl, heteroaryl or heterocyclyl, wherein the ring bound to the parent structure is cycloalkyl. Unlimited examples include indanyl, tetrahydronaphthyl, benzocycloheptyl and the like. The cycloalkyl may be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, amino, haloalkyl, hydroxyalkyl, carboxyl, carboxylic ester.

"Heterocyclyl" refers to a 3 to 20 membered saturated and/or partially unsaturated monocyclic or polycyclic hydrocarbon group having one or more heteroatoms selected from the group consisting of N, O, and S(O)$_m$ (wherein m is an integer selected from 0 to 2) as ring atoms, but excluding —O—O—, —O—S— or —S—S— in the ring, and the remaining ring atoms being carbon atoms. Preferably, heterocyclyl has 3 to 12 atoms with 1 to 4 heteroatoms, more preferably 3 to 10 atoms with 1 to 3 heteroatoms, and most preferably 5 to 6 atoms with 1 to 2 heteroatoms. Unlimited examples of monocyclic heterocyclyl include, but are not limited to, pyrrolidinyl, piperidyl, piperazinyl, morpholinyl, thiomorpholinyl, homopiperazinyl, pyranyl, tetrahydrofuranyl, and the like. Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called a spiro atom), wherein said rings have one or more heteroatoms selected from the group consisting of N, O, and S(O)$_m$ (wherein m is an integer selected from 0 to 2) as ring atoms and the remaining ring atoms being carbon atoms, wherein one or more rings may contain one or more double bonds, but none of the rings has a completely conjugated pi-electron system; preferably 6 to 14 membered spiro heterocyclyl, and more preferably 7 to 10 membered spiro heterocyclyl. According to the number of common spiro atoms, spiro heterocyclyl may be divided into mono-spiro heterocyclyl, di-spiro heterocyclyl, or poly-spiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Unlimited examples of spiro heterocyclyls include, but are not limited to:

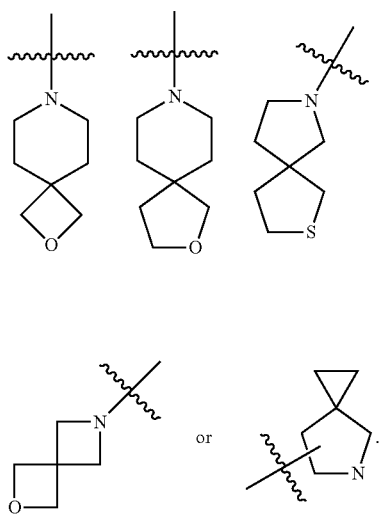

"Fused heterocyclyl" refers to a 5 to 20 membered polycyclic heterocyclyl group, wherein each ring in the system shares an adjacent pair of atoms with another ring, wherein one or more rings may contain one or more double bonds, but none of the rings has a completely conjugated pi-electron system, and wherein said rings have one or more heteroatoms selected from the group consisting of N, O, and $S(O)_m$ (wherein m is an integer selected from 0 to 2) as ring atoms, and the remaining ring atoms being carbon atoms; preferably 6 to 14 membered fused heterocyclyl, and more preferably 7 to 10 membered fused heterocyclyl. According to the number of membered rings, fused heterocyclyl may be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Unlimited examples of fused heterocyclyl include, but are not limited to:

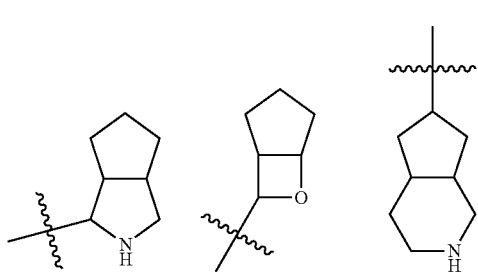

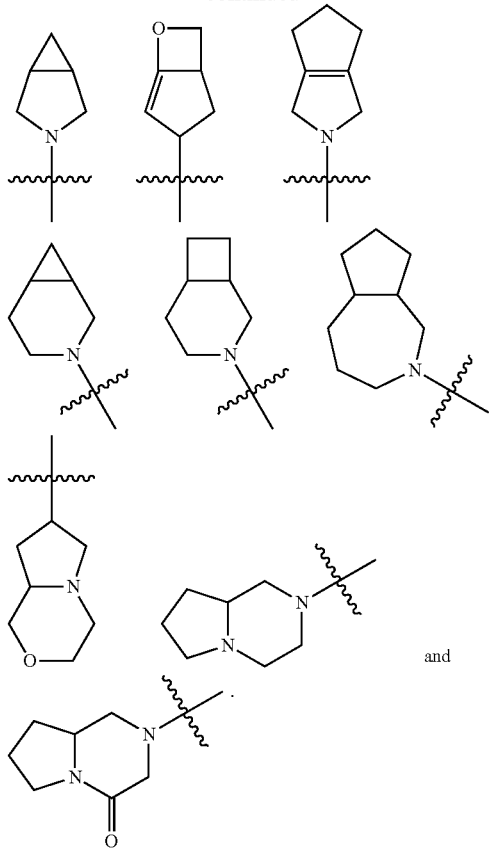

"Bridged heterocyclyl" refers to a 5 to 14 membered poly cyclic heterocyclyl group, wherein every two rings in the system share two disconnected atoms, wherein the rings may have one or more double bonds, but none of the rings has a completely conjugated pi-electron system, and the rings have one or more heteroatoms selected from the group consisting of N, O, and $S(O)_m$ (wherein m is an integer selected from 0 to 2) as ring atoms, and the remaining ring atoms being carbon atoms; preferably 6 to 14 membered bridged heterocyclyl, and more preferably 7 to 10 membered bridged heterocyclyl. According to the number of membered rings, bridged heterocyclyl may be divided into bicyclic, tricyclic, tetracyclic or polycyclic bridged heterocyclyl, and preferably bicyclic, tricyclic or tetracyclic bridged heterocyclyl, and more preferably bicyclic or tricyclic bridged heterocyclyl. Unlimited examples of bridged heterocyclyls include, but are not limited to:

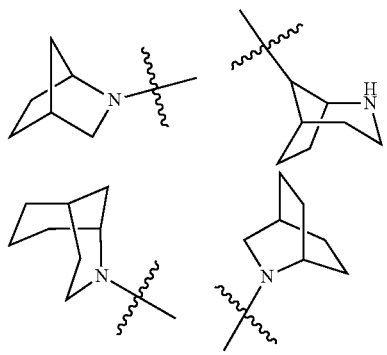

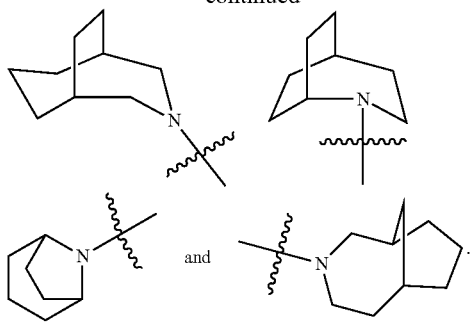

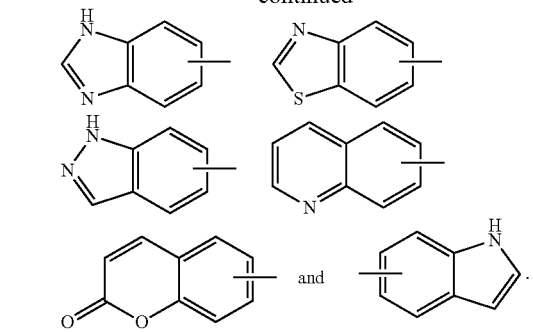

Said heterocyclyl can be fused to aryl, heteroaryl or cycloalkyl, wherein the ring bound to the parent structure is heterocyclyl. Unlimited examples include, but are not limited to:

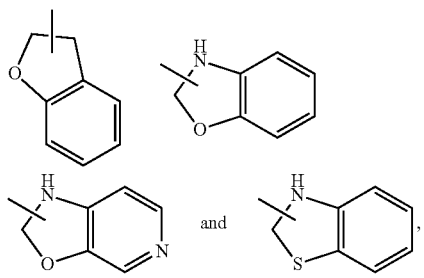

etc.

The heterocyclyl may be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, amino, haloalkyl, hydroxyalkyl, carboxyl, carboxylic ester.

"Aryl" refers to a 6 to 14 membered full-carbon monocyclic ring or polycyclic fused ring (i.e. each ring in the system shares an adjacent pair of carbon atoms with another ring in the system) group having a completely conjugated pi-electron system; preferably 6 to 10 membered aryl, more preferably phenyl and naphthyl, and most preferably phenyl. The aryl can be fused to heteroaryl, heterocyclyl or cycloalkyl, wherein the ring bound to parent structure is aryl. Unlimited examples include, but are not limited to:

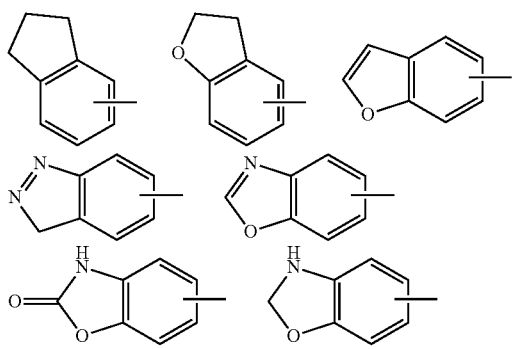

The aryl may be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, amino, haloalkyl, hydroxyalkyl, carboxyl, carboxylic ester.

"Heteroaryl" refers to 5 to 14 membered aryl having 1 to 4 heteroatoms selected from the group consisting of O, S and N as ring atoms and remaining ring atoms being carbon atoms; preferably 5 to 10 membered heteroaryl, more preferably 5- or 6-membered heteroaryl such as furyl, thienyl, pyridyl, pyrrolyl, N-alkyl pyrrolyl, pyrimidinyl, pyrazinyl, imidazolyl, tetrazolyl and the like. The heteroaryl can be fused to aryl, heterocyclyl or cycloalkyl, wherein the ring bound to parent structure is heteroaryl. Unlimited examples include, but are not limited to:

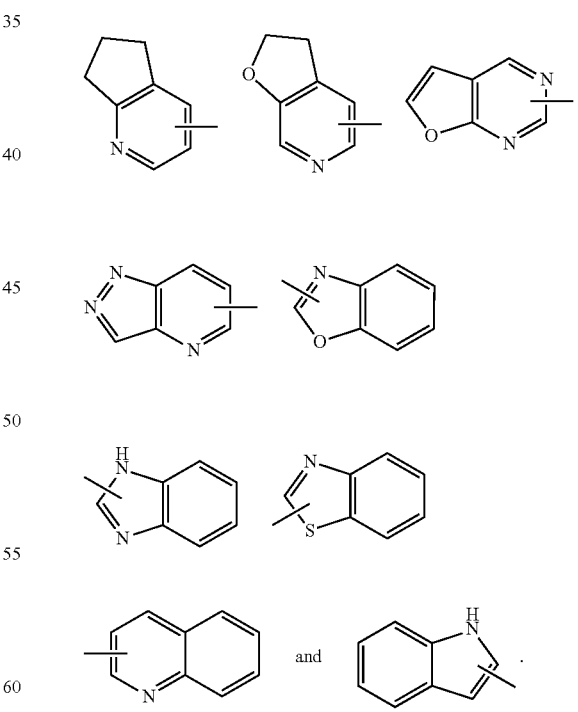

The heteroaryl may be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, amino, haloalkyl, hydroxyalkyl, carboxyl, carboxylic ester.

"Optional" or "optionally" means that the event or circumstance described subsequently can, but need not, occur, and such description includes the situation in which the event or circumstance may or may not occur. For example, "the heterocyclic group optionally substituted with an alkyl" means that an alkyl group can be, but need not be, present, and such description includes the situation of the heterocyclic group being substituted with an alkyl and the heterocyclic group being not substituted with an alkyl.

"Substituted" refers to one or more hydrogen atoms in a group, preferably up to 5, more preferably 1 to 3 hydrogen atoms, independently substituted with a corresponding number of substituents. It goes without saying that the substituents only exist in their possible chemical position. The person skilled in the art is able to determine whether the substitution is possible or impossible by experiments or theory without paying excessive efforts. For example, when amino or hydroxy having free hydrogen is bound to a carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism and the absorption of the active ingredient and thus displaying biological activity.

"Pharmaceutically acceptable salts" refers to salts of the compounds of the invention that are safe and effective in mammals and have the desired biological activity.

The term "Drug/Antibody Ratio (DAR)" as used herein refers to the number of drugs that are conjugated to each antibody molecule. Because antibody-drug conjugate samples contain multiple components with different DAR values, the concepts of "average DAR value" and "DAR value distribution" are more suitable for describing the composition of antibody drug conjugates. The average DAR value is the ratio of the total number of drug molecules in a sample to the total number of antibodies, and the DAR value distribution refers to the content distribution of the components with various DAR value in the sample.

The pharmaceutically acceptable salts of the compound of formula I according to the present invention may be an acid addition salt or a basic addition salts. The acid may be inorganic acids including, but not limited to, hydrochloric acid, sulfuric acid, phosphoric acid, hydrobromic acid; or organic acids including, but not limited to, citric acid, maleic acid, oxalic acid, formic acid, acetic acid, propionic acid, glycolic acid, benzoic acid, fumaric acid, trifluoroacetic acid, succinic acid, tartaric acid, lactic acid, glutamic acid, aspartic acid, salicylic acid, pyruvic acid, methanesulfonic acid, benzenesulfonic acid, p-toluenesulfonic acid. The base may be inorganic bases including, but not limited to, sodium hydroxide, potassium hydroxide, magnesium hydroxide, calcium hydroxide; or organic bases including, but not limited to, ammonium hydroxide, triethylamine, arginine, or lysine.

In another aspect of the invention, the antibody drug conjugate according to the present invention can be prepared as a clinically useful pharmaceutical composition. According to clinical indications, administration route and method, the pharmaceutical preparations include, but are not limited to, oral preparations such as tablets, gels, soft/hard capsules, emulsions, dispersible powders, granules, water/oil suspoemulsions; injections including intravenous injections, intramuscular injections, intraperitoneal injections, rectal administration suppositories, intracranial injections, which may be aqueous solutions or oil solutions; topical formulations including creams, ointments, gels, water/oil solutions, and packages; inhalation formulations including fine powders, liquid aerosols, and various dosage forms suitable for in vivo implantation.

The pharmaceutical composition of the present invention may be added with conventional pharmaceutical excipients as needed. These excipients should comply with the pharmaceutical preparation process rules and be compatible with the active ingredient. The solid oral preparation excipients include, but are not limited to, mannitol, lactose, starch, magnesium stearate, cellulose, glucose, sucrose, cyclodextrin, and vitamin E-PEG 1000 which promotes intestinal absorption. Oral formulations may be added with suitable colorants, sweeteners, flavoring agents and preservatives.

It is well-known to those skilled in the art that the dosage of the drug to be administered depends on a variety of factors including, but not limited to, the activity of the specific compound employed, the age of the patient, the patient's body weight, the patient's condition, diet, time of administration, mode of administration, rate of excretion, combination of drugs, and the like. In addition, the optimal treatment modalities such as the mode of treatment, the daily dosage of the compound of the general formula, or the type of pharmaceutically acceptable salt can be verified according to conventional treatment regimens.

For tetramaleimide linkers, the distance between any two maleimide groups (linker size) may affect the interchain crosslinking between tetramaleimide linkers and antibodies. The length and structure of the side chain used to link the drugs may also affect the ADC property and potency. Therefore, the inventor synthesized a series of tetramaleimide linkers with different sizes to study the above-mentioned influence factors.

Preparation Method for ADCs
The ADCs according to the invention can be prepared via the method as following.
Method 1 is shown in scheme 2.
Scheme 2
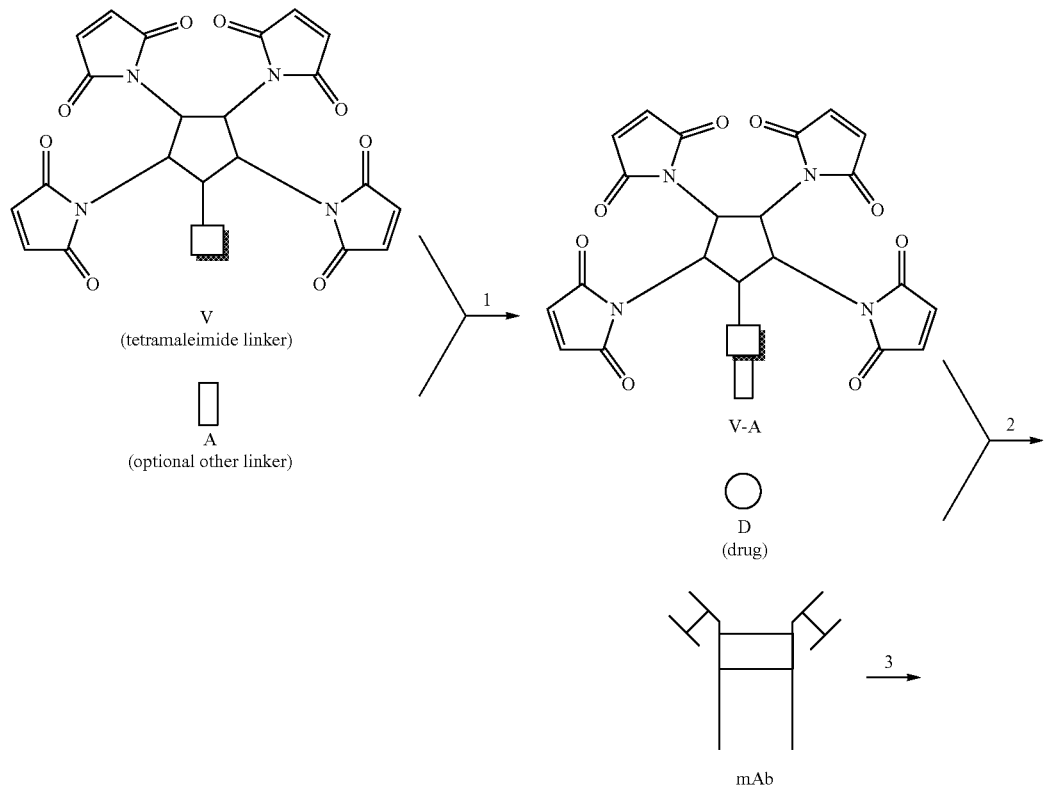
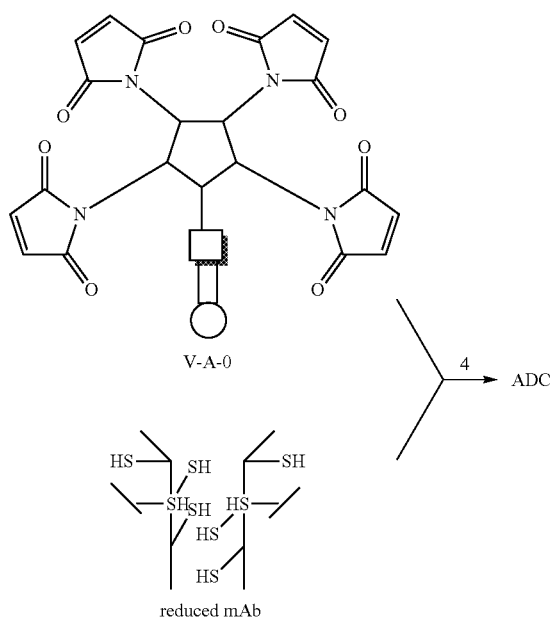

Step 1: The optional other linker (A) and a tetramaleimide linker (V) are conjugated to afford a linker molecule (V-A);

Step 2: V-A and a drug (D) are conjugated to give tetramaleimide linker-optional other linker-drug (V-A-D);

Step 3: The inter-chain disulfide bonds of an antibody (L) are reduced to produce a total of eight sulfhydryl groups;

Step 4: V-A-D is crosslinked with the reduced sulfhydryl groups or other amino acid residues of the antibody to afford ADC of formula

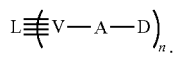

Method 2 is shown in scheme 3.

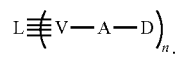

Use

The antibody-drug conjugates according to the present invention target a special cell population and bind to the specific cell surface proteins (antigens) to form a complex, followed by the internalization of the complex into the cell and releasing of the drug within the cell in active form.

The antibody-drug conjugates according to the present invention target a special cell population and bind to the specific cell surface proteins (antigens) to take effects; or release drugs outside the cell, followed by the permeation of the drugs into the cell to take effects.

Scheme 3

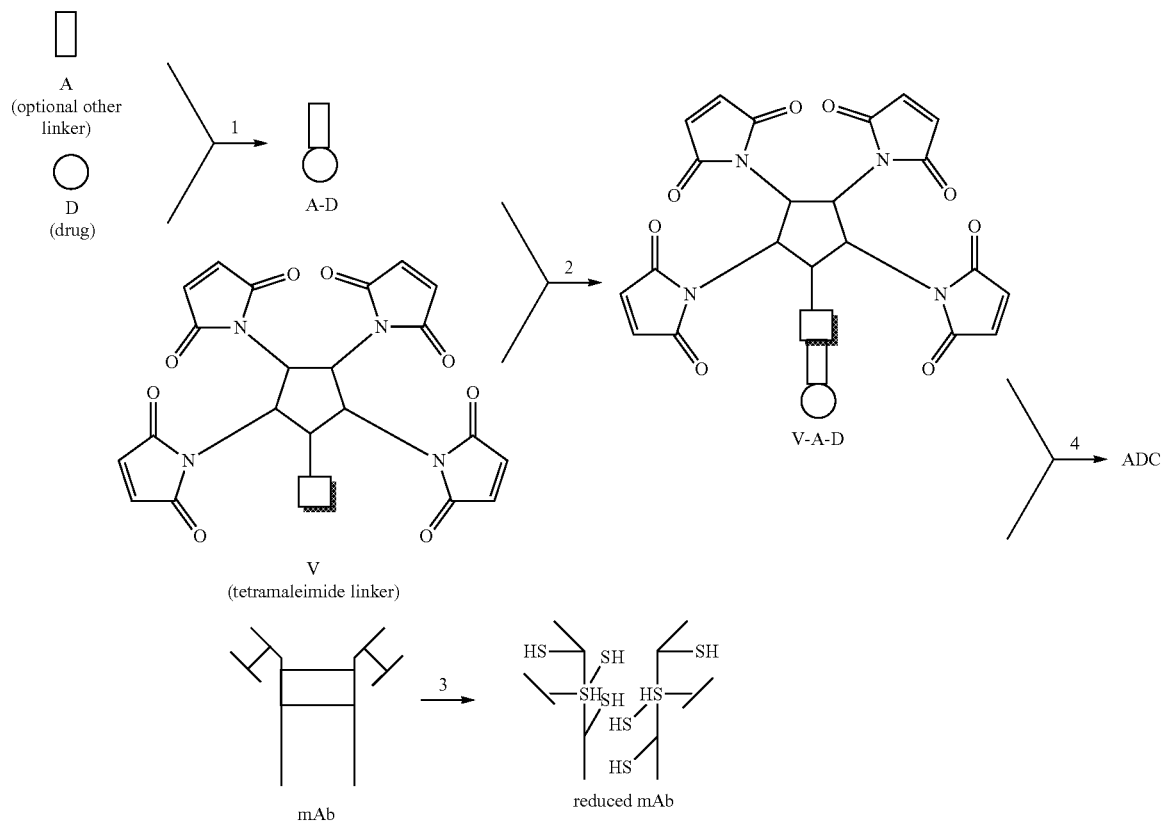

Step 1: The optional other linker (A) and a drug (D) are conjugated to afford a linker-Drug (A-D);

Step 2: A tetramaleimide linker (V) and A-D are conjugated to give tetramaleimide linker-optional other linker-drug (V-A-D);

Step 3: The inter-chain disulfide bonds of an antibody (L) are reduced to produce a total of eight sulfhydryl groups;

Step 4: V-A-D is crosslinked with the sulfhydryl groups or other amino acid residues of the antibody to afford ADC of formula The present invention provides a method for the treatment of cancers or other tumors in animal subjects comprising administration of a therapeutically effective amount of the antibody-drug conjugate according to the invention to a subject suffering from cancers or other tumors.

The present invention provides a method for the treatment of autoimmune disease or infectious disease comprising administration of a therapeutically effective amount of the antibody-drug conjugate according to the invention to a subject suffering from autoimmune diseases or infectious diseases.

The above technical features or features mentioned in the following examples can be combined at will. All the features disclosed in the present invention can be applied together with any combination, and each feature can be substituted with any identical, equal, or similar features. Unless otherwise specific state, all disclosed features are only general examples of the equal or similar features.

The present invention has the following main advantages:
1. The present invention provides, for the first time, a conjugation technology for producing an ADC product with both controlled average DAR of 2 and high homogeneity;
2. The innovative tetramaleimide linkers according to the present invention comprise four maleimide groups, which can conjugate interchain cysteine and/or other amino acid residues in the antibody simultaneously by simple chemical method. Compared to the ones obtained via traditional conjugation methods, the conjugates obtained with the present tetramaleimide linkers have DAR2 fraction as the main components (more than 90%) and much narrower DAR distribution. As a result, the homogeneity of the products is greatly improved;
3. The conjugation technology according to the present invention is applicable to most antibodies, such as IgG1, which can avoid complicated antibody engineering used to introduce specific sites for coupling. Therefore, the conjugation technology may have very broad application prospect.

EXAMPLES

Figure 1:
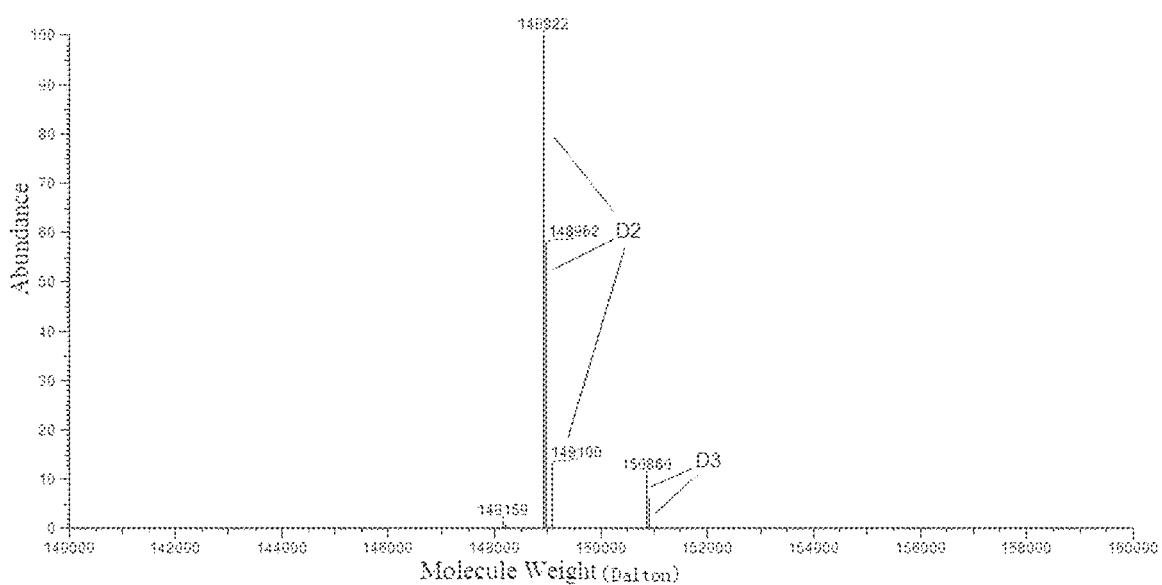
FIG. 1 illustrates the native MS spectrum of H-5-vcM-MAE of the invention.

The present invention will be further described in details with the following examples. However, it should be understood that these examples are used to illustrate the present invention, but should not be considered as limiting the scope of the invention. The unstated experiment conditions are generally according to routine conditions or conditions suggested by manufacturers. All reactions were conducted under nitrogen atmosphere, except for hydrogenation reaction.

Unless otherwise defined, all of the professional and scientific terms used in the present invention have the same meaning as those familiar by the expertise in the art. Furthermore, any method or material similar or equal to those used in the present invention can be applied herein. The optimized methods and materials used in the present invention are only used for illustration while not for limitation.

Abbreviation
Ab antibody
Ac acetyl
ACN acetonitrile
ADC antibody-drug conjugate
BOC (Boc) tert-butoxycarbonyl
Cbz benzyloxy carbonyl
t-Bu tert-butyl
DCM dichloromethane
DIPEA diisopropylethylamine
DMF N,N-dimethylformamide
ELISA enzyme linked immunosorbent assay
EtOAc ethyl acetate
Eq (eq) equivalent
g gram
h hour
HATU 2-(7-Aza-1H-benzotriazole-1-yl)-1,1,3,3-tetramethyluronium hexafluorophosphate
HOSu N-hydroxy succinimide
HIC hydrophobic interaction chromatography
HPLC high performance liquid chromatography
LC-MS liquid chromatography-mass spectrum
mAb monoclonal antibody
min minute
mL milliliter
MS mass spectrometry
nm nanometer
μg microgram
μL microliter
PE petroleum ether
RP-HPLC reverse phase-high performance liquid chromatography
prep-RP-HPLC preparative-reverse phase-high performance liquid chromatography
rt room temperature
$R_t$ retention time
SDS-PAGE sodium dodecyl sulfate polyacrylamide gel electropheresis
SEC size exclusion chromatography
TEA triethylamine
TFA trifluoroacetic acid
THF tetrahydrofuran
TLC thin layer chromatography
TsCl p-tolyl chloride Unless otherwise stated, all of the anhydrous solvents are purchased from the suppliers and kept under nitrogen atmosphere. All other reagents and solvents purchased are of high purity and need not to be purified before use.

The structure of the compound is identified by nuclear magnetic resonance (NMR) and/or mass spectrometry (MS). NMR chemical shifts (δ) are given in $10^{-6}$ (ppm). NMR is determined by Bruker AVANCE III 500. The solvents are deuterated-dimethyl sulfoxide (DMSO-$d_6$), deuterated-chloroform (CDCl$_3$) and deuterated-methanol (CD$_3$OD) with tetramethylsilane (TMS) as an internal standard.

Liquid chromatography-mass spectrometry (LC-MS) is determined on Agilent 6110 (acid method) or 6120B (base method) mass spectrometers coupled with Hewlette-Packard Agilent 1200 HPLC.

Method 1: Waters Sunfire C18 reverse phase column (4.60×50 mm, 3.5 μm) is used in the acid HPLC method for separation, and the eluting gradient is 5%-95% B (acetonitrile, containing 0.01% TFA) in A (water, containing 0.01% TFA) over 1.4 min. The flow rate is 2.0 mL/min, and the column temperature is 50° C.

Method 2: Waters Sunfire C18 reverse phase column (4.60×50 mm, 3.5 μm) is used in the acid HPLC method for separation, and the eluting gradient is 5%-95% B (acetonitrile, containing 0.01% TFA) in A (water, containing 0.01% TFA) over 1.4 min. The flow rate is 2.3 mL/min, and the column temperature is 50° C.

Method 3: Waters Sunfire C18 reverse phase column (3.0×30 mm, 2.5 μm) is used in the acid HPLC method for separation, and the eluting gradient is 5%-95% B (acetonitrile, containing 0.01% TFA) in A (water, containing 0.01% TFA) over 1.5 min. The flow rate is 1.5 mL/min, and the column temperature is 50° C.

Method 4: Waters Sunfire C18 reverse phase column (4.6×50 mm, 3.5 μm) is used in the acid HPLC method for separation, and the eluting gradient is 5%-95% B (acetonitrile, containing 0.01% TFA) in A (water, containing 0.01% TFA) over 1.2 min. The flow rate is 2.0 mL/min, and the column temperature is 50° C.;

Method 5: Waters Xbridge C18 reverse phase column (4.60×50 mm, 3.5 μm) is used in the base HPLC method for separation, and the eluting gradient is 5%-95% B (acetonitrile) in A (water, containing 10 mM ammonium bicarbonate) over 1.5 min. The flow rate is 2.0 mL/min, and the column temperature is 40° C.

Purification by preparative HPLC is conducted on a Gilson instrument. Waters Sunfire C18 reverse phase column (250×19 mm, 10 μm) is used for separation.

Method 6: The acid HPLC preparation method. Mobile phase: A is aqueous solution containing 0.1% TFA; B is ACN. The flow rate is 20 mL/min.

SK-BR-3 human breast cancer cell is purchased from ATCC. Her2 antigen is purchased from Sino Biological Inc (Beijing). Antibody H (Herceptin Biosimilar, IgG1) is purchased from Genor Biopharma Co. Ltd. (Shanghai). Antibody P (Perjeta Biosimilar, IgG1) is purchased from Biochem partner Co. Ltd. (Shanghai). The enzyme labeled anti-antibody is purchased from Sigma (Shanghai). Substrate solution is purchased from Decent Biotech (Shanghai). Cell Counting Kit (CCK-8) cell proliferation-cytotoxicity assay kit is purchased from Dojindo (Shanghai).

Example 1

Synthesis of Compound 1 (Linker 1)

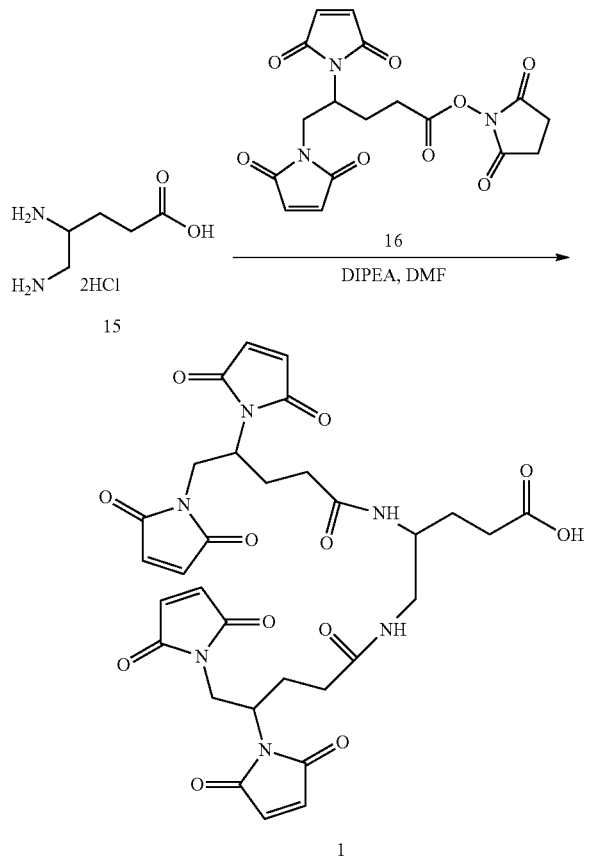

(S)-4,5-Diaminopentanoic acid dihydrochloride (15) (10 mg, 49 μmol, prepared according to Tetrahedron Asymmetry, 1993, 4, 91-100) and compound 16 (38 mg, 98 μmol, prepared according to WO2014114207) were dissolved in DMF (0.5 mL), to which DIPEA (25 mg, 196 μmol) was then added. The reaction mixture was stirred at room temperature for 2 h, and then purified by RP-HPLC (method 6: 32%-40% B in 8 min→95% B in 4 min) to give compound 1 (12 mg) as a white solid.

LC-MS (method 1): Rt=1.39 min; m/z (ES+) 681.1 (M+H)$^+$.

$^1$H NMR (500 MHz, CD$_3$OD) δ 6.80 (s, 4H), 6.78 (s, 4H), 4.20-4.12 (m, 2H), 4.01-3.96 (m, 2H), 3.92-3.87 (m, 1H), 3.71-3.66 (m, 2H), 3.37-3.32 (m, 1H), 3.11-3.07 (m, 1H), 2.42-2.30 (m, 4H), 2.28-2.08 (m, 6H), 1.83-1.76 (m, 1H), 1.66-1.59 (m, 1H).

Example 2

Synthesis of Compound 2 (Linker 2)

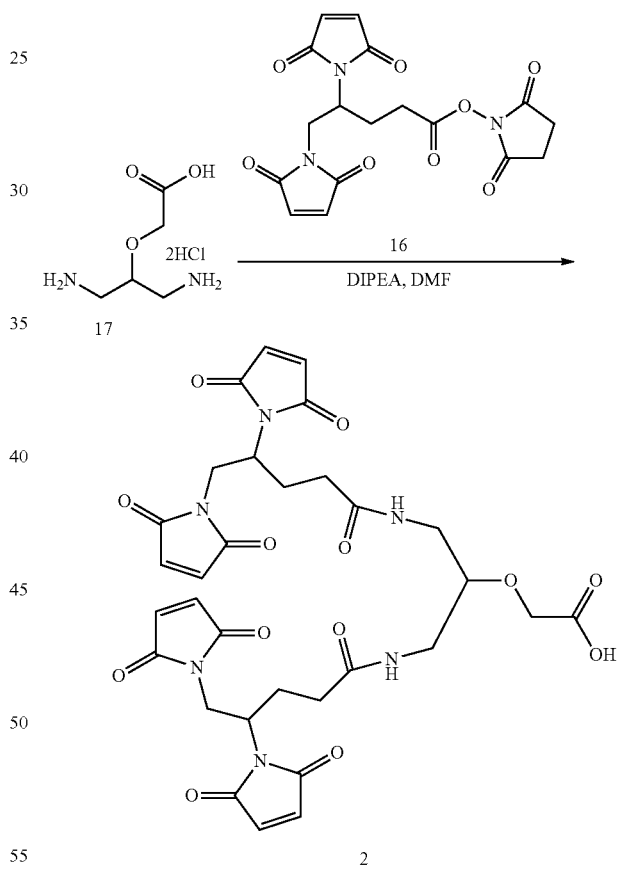

2-(1,3-Diamino-2-propoxy)acetic acid dihydrochloride (17) (10 mg, 45 μmol, preparation according to WO2014114207) and compound 16 (35 mg, 90 μmol) were dissolved in DMF (0.5 mL), to which DIPEA (23 mg, 180 μmol) was then added. The reaction mixture was stirred at room temperature for 4 h, and then purified by RP-HPLC (method 6: 30%-60% B in 8 min→95% B in 4) to give compound 2 (9 mg) as a white solid.

LC-MS (method 2): Rt=1.63 min; m/z (ES+) 697.0 (M+H)$^+$.

¹H NMR (500 MHz, CD₃OD) δ 6.79 (s, 4H), 6.78-6.76 (m, 4H), 4.22 (s, 2H), 4.18-4.14 (m, 2H), 4.00-3.95 (m, 2H), 3.70-3.66 (m, 2H), 3.50-3.45 (m, 1H), 3.31-3.27 (m, 1H), 3.24-3.23 (d, 2H), 3.18-3.14 (m, 1H), 2.46-2.38 (m, 2H), 2.29-2.17 (m, 4H), 2.14-2.08 (m, 2H).

Example 3

Synthesis of Compound 3 (Linker 3)

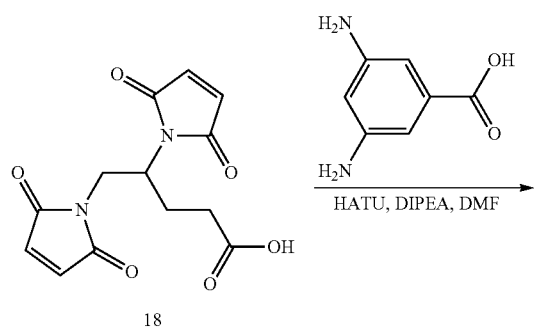

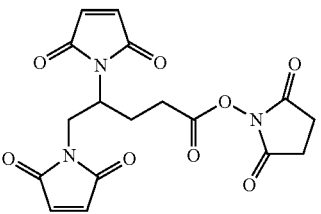

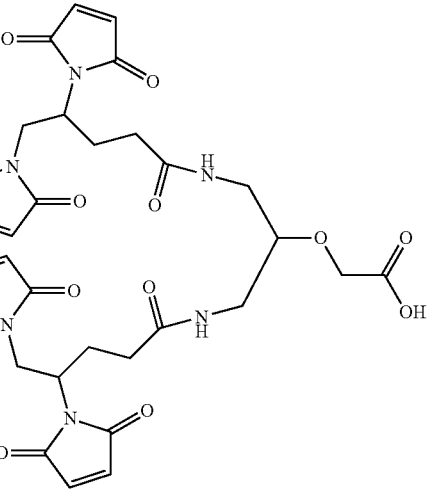

4,5-Bis(2,5-dioxo-2,5-dihydro-1H-pyrrol-1-yl)pentanoic acid (18) (10 mg, 65 µmol, prepared according to WO2014114207) and 3,5-diaminobenzoic acid (38 mg, 130 µmol) were dissolved in DMF (0.6 mL), to which HATU (62 mg, 160 µmol) and DIPA (18 mg, 140 µmol) were then added. The reaction mixture was stirred at room temperature for 18 h, and then purified by RP-HPLC (method 6: 40%-70% B in 8 min→95% B in 4) to give compound 3 (6 mg) as a white solid.

LC-MS (method 2): Rt=1.74 min; mz (ES+) 700.8 (M+H)⁺.

¹H NMR (500 MHz, DMSO-d₆) δ 10.03 (s, 2H), 8.02 (s, 1H), 7.84 (s, 2H), 7.01 (s, 4H), 6.98 (s, 4H), 4.09-4.02 (m, 2H), 3.84-3.75 (m, 2H), 3.65-3.61 (m, 2H), 2.33-2.25 (m, 6H), 2.06-1.95 (m, 2H).

Example 4

Synthesis of Compound 4 (Linker 4)

2-(1,4-Diaminobutan-2-yloxy)acetic acid (19) (20 mg, 85 µmol, prepared according to WO2014114207) and compound 16 (66 mg, 170 µmol) were dissolved in DMF (0.4 mL), to which DIPEA (44 mg, 340 µmol) was then added. The reaction mixture was stirred at room temperature for 4 h, and then purified by RP-HPLC (method 6: 35%-60% B in 8 min→95% B in 4) to give compound 4 (9 mg) as a white solid.

LC-MS (method 1): Rt=1.41 min; m/z (ES+) 711.1 (M+H)⁺.

¹H NMR (500 MHz, CD₃OD) δ 6.80 (s, 4H), 6.77 (s, 4H), 4.21 (s, 2H), 4.18-4.12 (m, 2H), 4.00-3.94 (m, 2H), 3.70-3.65 (m, 2H), 3.55-3.51 (m, 1H), 3.49-3.35 (m, 1H), 3.30-3.14 (m, 3H), 2.46-2.38 (m, 2H), 2.29-2.17 (m, 4H), 2.15-2.08 (m, 2H), 1.68-1.63 (m, 2H).

Example 5

Synthesis of Compound 5 (Linker 5)

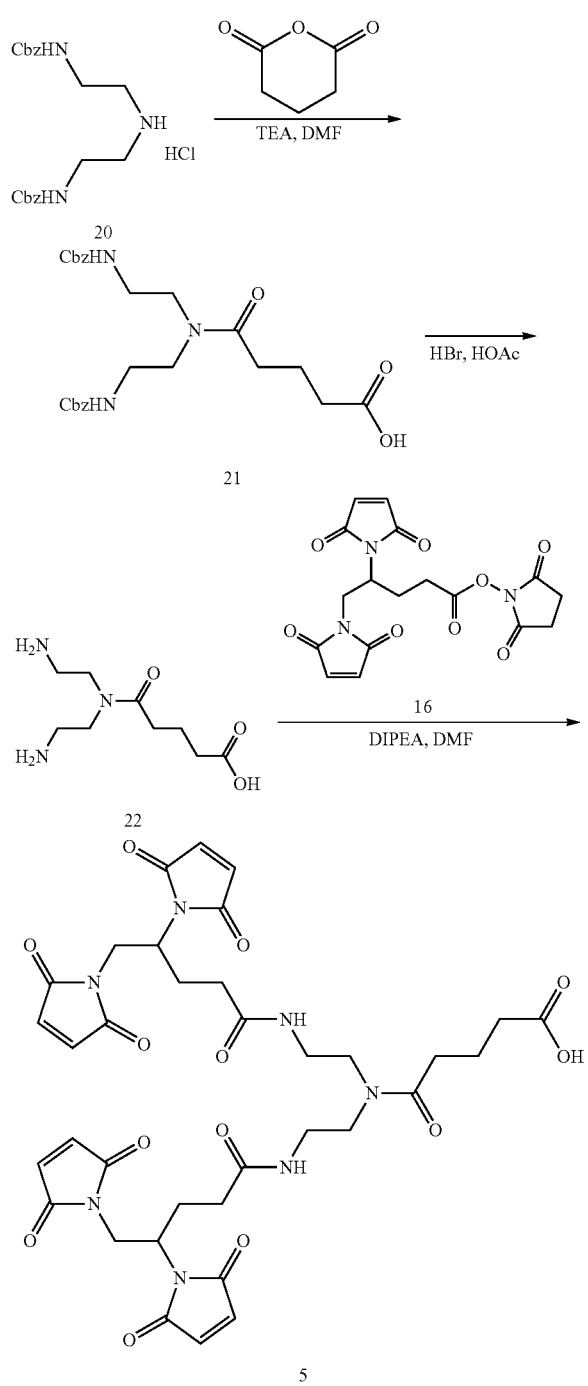

Step 1: Synthesis of 5-(bis(2-(benzyloxycarbonylamino)ethyl)amino)-5-oxopentanoic Acid (21)

Bis(2-(benzyloxycarbonylamino)ethyl)amine hydrochloride (20) (815 mg, 2 mmol, prepared according to European Journal of Medicinal Chemistry, 2009, 44, 678-688) and TEA (0.70 mL, 5 mmol) were dissolved in DMF (5 mL), to which glutaric anhydride (228 mg in 1 mL DMF, 2 mmol) was then added dropwise. The reaction mixture was stirred at room temperature overnight, and then water (20 mL) was added. The mixture was extracted with DCM (15 mL×3), and the combined organic phase was sequentially washed with brine, dried over anhydrous sodium sulfate, filtered, and concentrated under reduced pressure. The residue was purified by silica gel column chromatography (eluent: DCM/MeOH 30:1) to give compound 21 (872 mg) as a pale yellow solid.

LC-MS (method 3): Rt=1.21 min; m/z (ES+) 486.3 $(M+H)^+$.

Step 2: Synthesis of 5-(bis(2-aminoethyl)amino)-5-oxopentanoic Acid Dihydrobromide (22)

A solution of HBr in acetic acid (33%, 3 mL) was added dropwise to compound 21 (522 mg, 1.1 mmol), and then the reaction mixture was stirred at room temperature for 15 min. Diethyl ether (20 mL) was added to the mixture, and the yellow precipitate was separated by centrifugation. The solid was suspended in diethyl ether (10 mL), and then was collected by centrifugation. The two-step process was repeated three times, after which the solid obtained was dried in vacuo (60° C.) to give hydrobromide of compound 22 (350 mg) as a yellow solid.

LC-MS (method 4): Rt=0.28 min; m/z (ES+) 218.0 $(M+H)^+$.

Step 3: Synthesis of Compound 5

Compound 22 hydrobromide (45 mg, 119 μmol) and compound 16 (50 mg, 128 μmol) were dissolved in DMF (5 mL), to which DIPEA (37 mg, 287 μmol) was then added. The reaction mixture was stirred at room temperature for 2 h, and then purified by RP-HPLC (method 6: 30%-60% B in 8 min→95% B in 4) to give compound 5 (30 mg) as a white solid.

LC-MS (method 2): Rt=1.62 min; m/z (ES+) 765.9 $(M+H)^+$.

$^1$H NMR (500 MHz, DMSO-$d_6$) δ7.95 (t, 1H), 7.84 (t, 1H), 7.00 (s, 4H), 6.97 (d, 4H), 4.01-3.95 (m, 2H), 3.80-3.75 (m, 2H), 3.61-3.56 (m, 2H), 3.25-3.16 (m, 4H), 3.15-3.06 (m, 4H), 2.27 (t, 2H), 2.23-2.15 (m, 4H), 2.04-1.98 (m, 4H), 1.96-1.88 (m, 2H), 1.72-1.66 (m, 2H).

Example 6

Synthesis of Compound 6 (Linker 6)

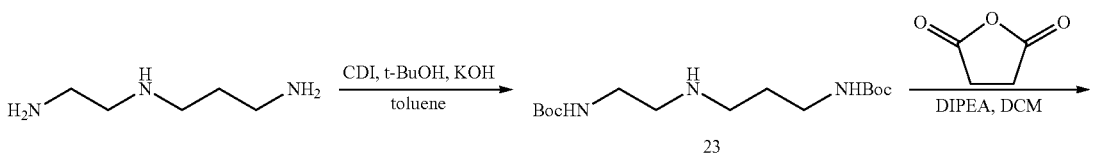

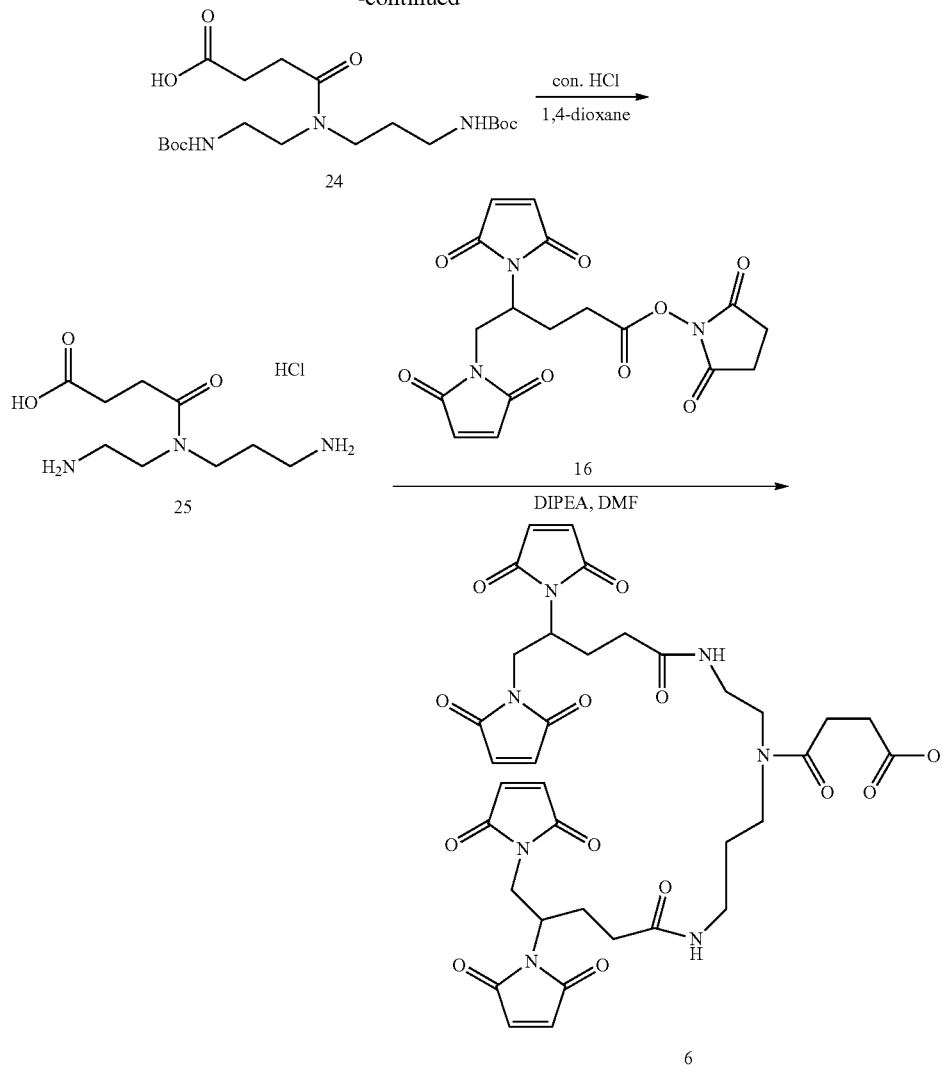

Step 1: Synthesis of (2-(tert-butoxycarbonylamino)ethyl)(3-(tert-butoxycarbonyl-amino)propyl)amine (23)

CDI (2.9 g, 18.0 mmoL), tert-butyl alcohol (1.33 g, 18.0 mmoL) and potassium hydroxide (24 mg, 0.43 mmoL) were sequentially added to toluene (30 mL), and the reaction mixture was stirred at 60° C. for 3 h. N-(2-aminoethyl)propane-1,3-diamine (1.0 g, 8.55 mmol) was added to the mixture, and then the reaction mixture was stirred at 60° C. for 3 h. The reaction mixture was cooled to room temperature, and concentrated under reduced pressure to remove the solvent. DCM (50 mL) was added to the residue, and then the mixture was washed with water (30 mL×3). The organic phase was dried over anhydrous sodium sulfate, filtered, and concentrated under reduced pressure to give compound 23 (1.0 g) as colorless oil. The crude product was used directly in the next step without purification.

Step 2: Synthesis of 4-((2-(tert-butoxycarbonylamino)ethyl)(3-(tert-butoxy carbonyl-amino)propyl)amino)-4-oxobutanoic Acid (24)

Compound 23 (1.0 g) was dissolved in DCM (15 mL), to which succinic anhydride (0.47 g, 4.73 mmol) and DIPEA (1.22 g, 9.46 mmol) were then sequentially added. The reaction mixture was stirred at room temperature for 18 h, and then washed with water (30 mL×2). The organic phase was dried over anhydrous sodium sulfate, filtered, and concentrated under reduced pressure to give compound 24 (1.2 g) as colorless oil. The crude product was used directly for next step without purification.

LC-MS (method 5): Rt=1.68 min; m/z (ES+) 418.3 (M+H)$^+$.

Step 3: Synthesis of 4-((2-aminoethyl)(3-aminopropyl)amino)-4-oxobutanoic Acid (25)

1,4-dioxane (6 mL) and concentrated hydrochloric acid (3 mL) were sequentially added to compound 24 (1.2 g), and the reaction mixture was stirred at room temperature for 2 h. The mixture was concentrated under reduced pressure to remove the solvent. The residue was dissolved in toluene, and then concentrated under reduced pressure to remove the solvent (repeated for 3 times). The residue was dried in vacuo to give compound 25 (520 mg) as a pale yellow solid.

LC-MS (method 5): Rt=0.32 min; m/z (ES+) 218.2 (M+H)$^+$.

Step 4: Synthesis of Compound 6

Compound 25 (24 mg, 83 μmol) and compound 16 (65 mg, 166 μmol) were dissolved in DMF (0.4 mL), to which DIPEA (43 mg, 332 μmol) was then added. The reaction mixture was stirred at room temperature for 4 h, and then purified by RP-HPLC (method 6: 32%-60% B in 8 min→95% B in 4) to give compound 6 (8 mg) as a white solid.

LC-MS (method 2): Rt=1.58 min; m/z (ES+) 766.2 (M+H)$^+$.

$^1$H NMR (500 MHz, CD$_3$OD) δ 6.80-6.78 (m, 8H), 4.19-4.13 (m, 2H), 4.01-3.95 (m, 2H), 3.70-3.67 (m, 2H), 3.48-3.36 (m, 5H), 3.30-3.06 (m, 3H), 2.68-2.62 (m, 4H), 2.44-2.38 (m, 2H), 2.25-2.06 (m, 6H), 1.82-1.70 (m, 2H).

Example 7

Synthesis of Compound 7 (Linker 7)

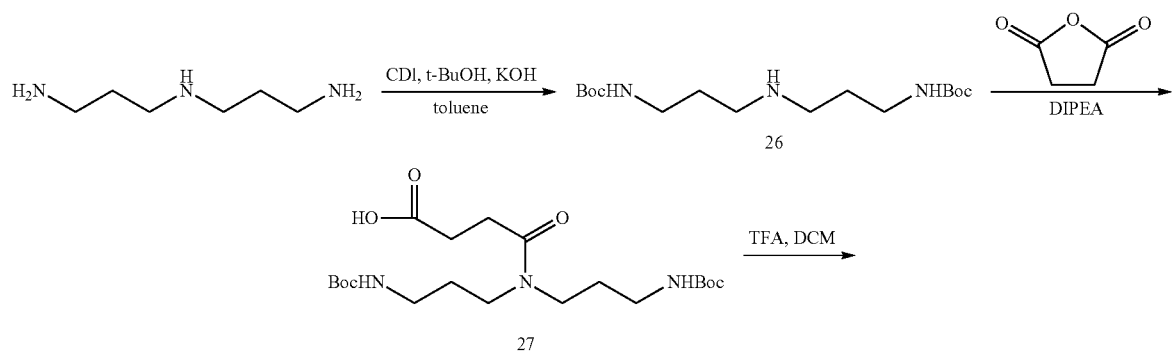

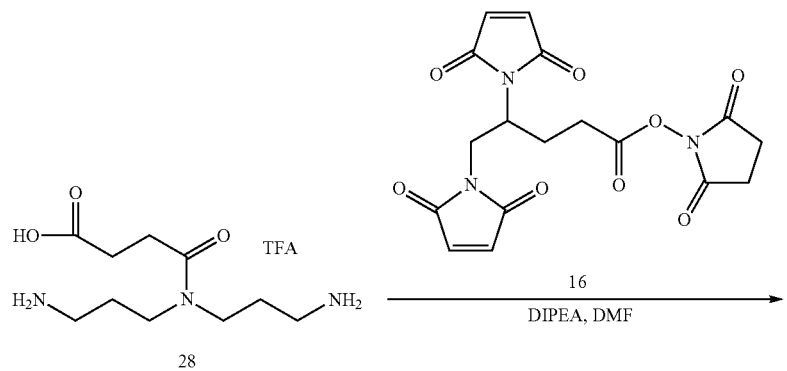

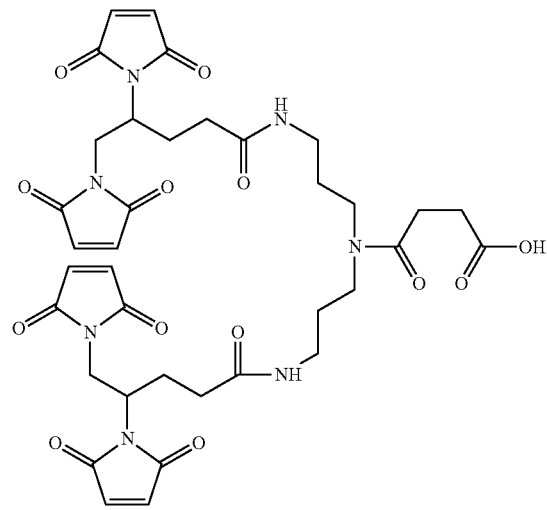

Step 1: Synthesis of bis(3-(tert-butoxycarbonylamino)propyl)amine (26)

CDI (3.4 g, 21 mmoL), tert-butylalcohol (1.55 g, 21 mmoL) and potassium hydroxide (28 mg, 0.50 mmoL) were added to toluene (30 mL) sequentially, and the reaction mixture was stirred at 60° C. for 3 h. N-(3-aminopropyl)-1,3-propyl diamine (1.31 g, 10 mmol) was added to the mixture, and the reaction mixture was stirred at 60° C. for 3 h. The reaction mixture was cooled to room temperature, and concentrated to remove the solvent. To the residue was added DCM (50 mL), and then the mixture was washed with water (30 mL×3). The organic phase was dried oven anhydrous sodium sulfate, filtered, and concentrated under reduced pressure to give compound 26 (1.0 g) as a white solid. The crude product was used directly in next step without purification.

Step 2: Synthesis of 4-(bis(3-(tert-butoxycarbonylamino)propyl)amino)-4-oxobutanoic Acid (27)

Compound 26 (1.0 g) was dissolved in DCM (15 mL), to which succinic anhydride (0.36 g, 3.6 mmol) and DIPEA (0.78 g, 6.0 mmol) were then sequentially added. The reaction mixture was stirred at room temperature for 18 h, and then concentrated under reduced pressure to remove the solvent. The residue was purified by silica gel column chromatography (eluent: DCM/MeOH 15:1) to give compound 27 (420 mg) as colorless oil.

Step 3: Synthesis of 4-(bis(3-aminopropyl)amino)-4-oxobutanoic Acid (28)

Compound 27 (420 mg) was dissolved in DCM (900 μL), and the solution was cooled to 0° C., to which TFA (300 uL) was added. The reaction mixture was stirred at room temperature for 3 h, and then concentrated under reduced pressure to remove the solvent. The residue was dissolved in toluene, and concentrated to remove the solvent (repeated 3 times). The residue was dried in vacuo to give compound 28 (480 mg) as pale yellow oil.

LC-MS (method 4): Rt=0.28, 0.34 min; m/z (ES+) 232.2 (M+H)+.

Step 4: Synthesis of Compound 7

Compound 28 (60 mg, 130 μmol) and compound 16 (101 mg, 260 μmol) were dissolved in DMF (0.6 mL), to which DIPEA (67 mg, 520 μmol) was then added. The reaction mixture was stirred at room temperature for 2 h, and then purified by RP-HPLC (method 6: 35%-58% B in 8 min→95% B in 4) to give compound 7 (35 mg) as a white solid.

LC-MS (method 2): Rt=1.47 min; m/z (ES+) 780.2 (M+H)+.

$^1$H NMR (500 MHz, CD$_3$OD) δ 6.80-6.78 (m, 8H), 4.18-4.13 (m, 2H), 4.00-3.95 (m, 2H), 3.71-3.67 (m, 2H), 3.42-3.35 (m, 4H), 3.25-3.08 (m, 4H), 2.68-2.67 (m, 4H), 2.45-2.38 (m, 2H), 2.25-2.08 (m, 6H), 1.86-1.80 (m, 2H), 1.73-1.68 (m, 2H).

Example 8

Synthesis of Compound 8 (Linker 8)

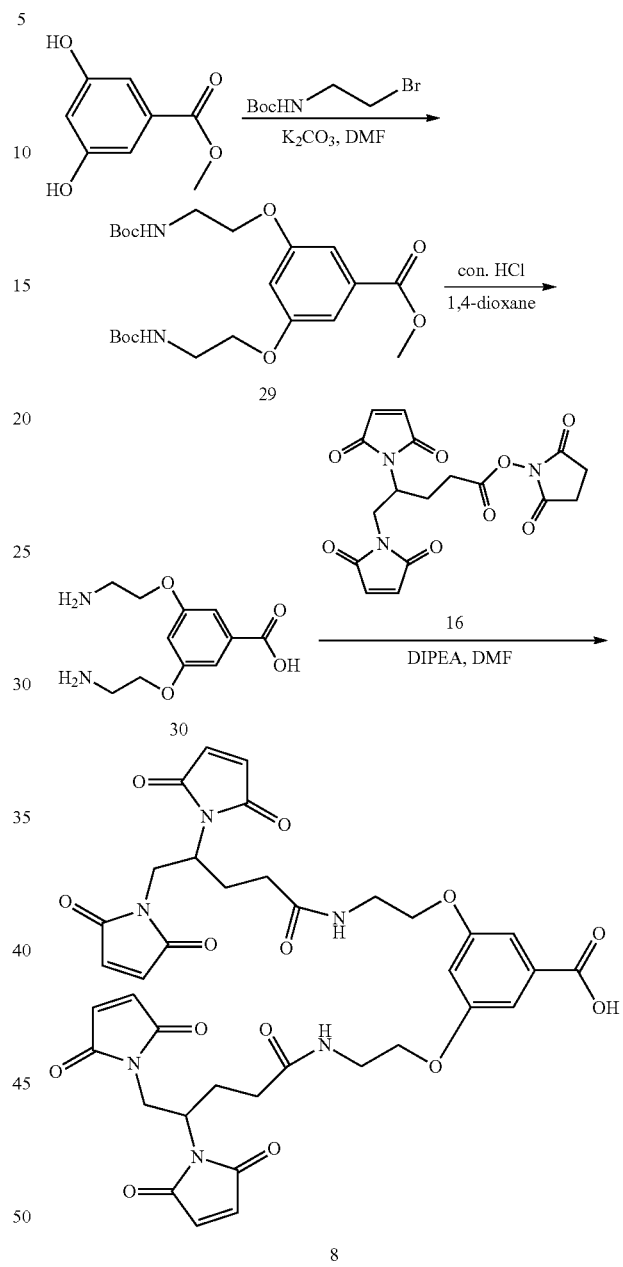

Step 1: Synthesis of methyl 3,5-bis(2-(tert-butoxycarbonylamino)ethoxy)benzoate (29)

Methyl 3,5-dihydroxybenzoate (200 mg, 1.19 mmol) and tert-butyl 2-bromoethylcarbamate (666 mg, 2.98 mmol) were dissolved in DMF (10 mL), to which potassium carbonate (411 mg, 2.98 mmol) was then added. The reaction mixture was stirred at 50° C. for 18 h, and then concentrated to remove the solvent. The residue was purified by silica gel column chromatography (eluent: PE/EA 10:1) to give compound 29 (450 mg) as colorless oil.

LC-MS (method 1): Rt=1.97 min; m/z (ES+) 477.0 (M+Na)+.

Step 2: Synthesis of 3,5-bis(2-aminoethoxy)benzoic Acid (30)

Compound 29 (200 mg) was dissolved in 1,4-dioxane (1 mL), to which concentrated hydrochloric acid (1 mL) was then added. The reaction mixture was stirred at 80° C. for 2 h, and then concentrated under reduced pressure to remove the solvent. To the residue was added toluene (3 mL), and then the mixture was concentrated under reduced pressure to remove the solvent. The same process was repeated several times until a solid was obtained. The solid was suspended in ethyl acetate, and then collected by filtration. The solid was dried in vacuo to give compound 30 (100 mg) as a brown solid. The crude product was used directly in next step without purification.

LC-MS (method 1): Rt=0.32 min; m/z (ES+) 241.0 (M+H)$^+$.

Step 3: Synthesis of Compound 8

Compound 30 (10 mg, 32 μmol) and compound 16 (25 mg, 64 μmol) were dissolved in DMF (0.5 mL), to which DIPEA (17 mg, 128 μmol) was then added. The reaction mixture was stirred at room temperature for 2 h, and then purified by RP-HPLC (method 6: 35%-65% B in 8 min→95% B in 4) to give compound 8 (6 mg) as a white solid.

LC-MS (method 4): Rt=1.34 min; m/z (ES+) 789.2 (M+H)$^+$.

$^1$H NMR (500 MHz, DMSO-d$_6$) δ 8.05 (t, 2H), 7.04 (d, 2H), 7.00 (s, 4H), 6.96 (s, 4H), 6.72 (t, 1H), 4.02-3.94 (m, 6H), 3.80-3.74 (m, 2H), 3.61-3.56 (m, 2H), 3.37-3.33 (m, 4H), 2.23-2.14 (m, 2H), 2.06 (t, 4H), 1.98-1.90 (m, 2H).

Example 9

Synthesis of Compound 9 (Linker 9)

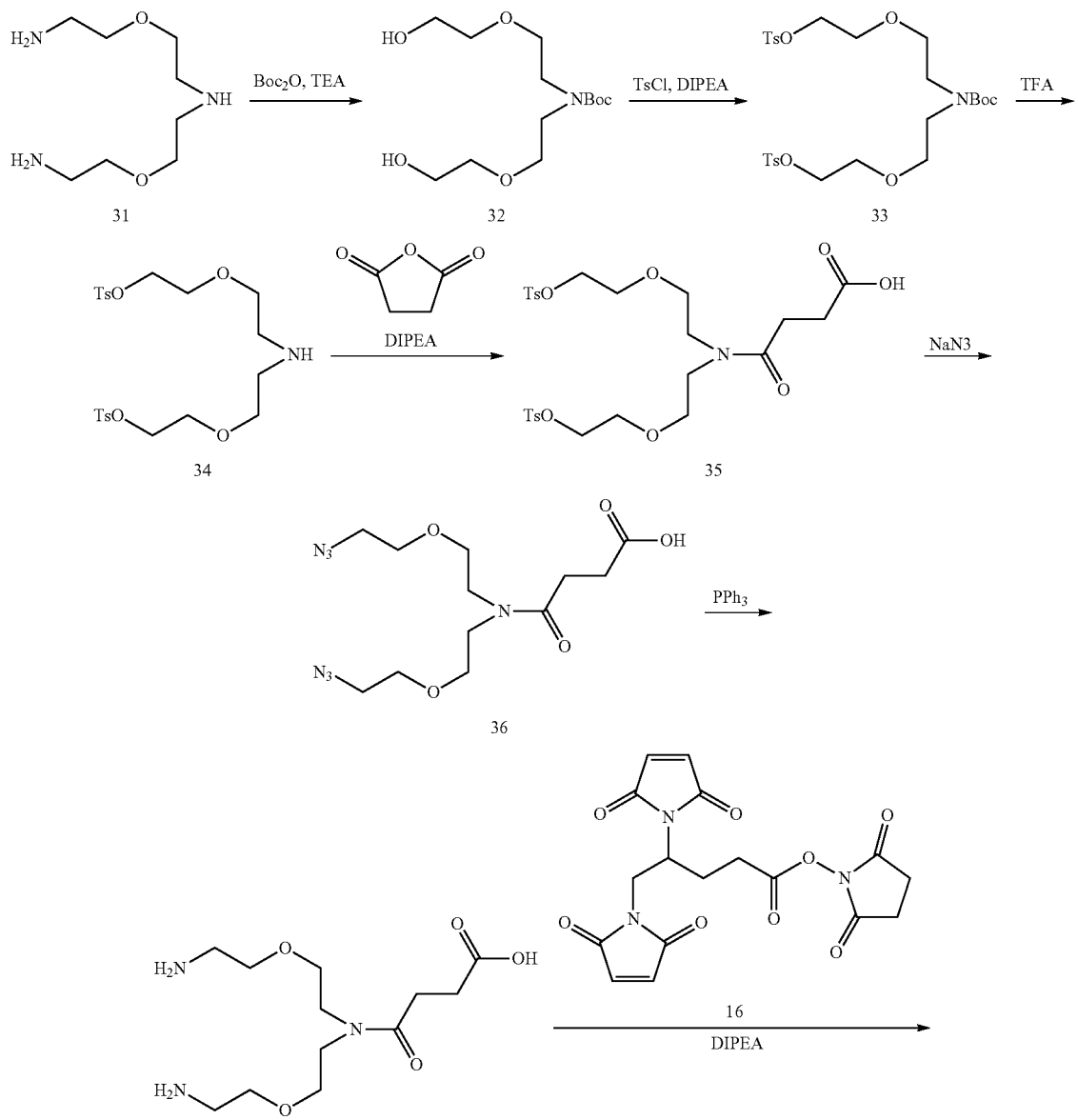

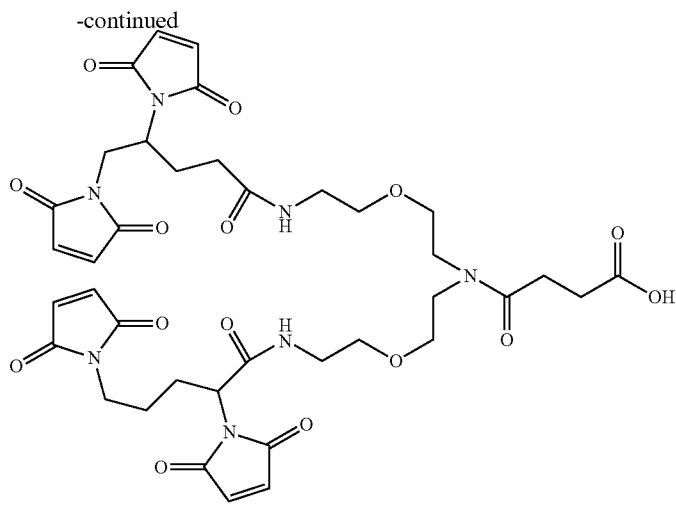

9

Step 1: Synthesis of tert-butyl bis(2-(2-hydroxyethoxy)ethyl)carbamate (32)

Bis(2-(2-hydroxyethoxy)ethyl)amine (31) (4.2 g, 21.8 mmol, prepared according to Journal of Organic Chemistry, 1995, 60, 6097-6102) and TEA were dissolved in DCM (30 mL), to which di-tert-butyl dicarbonate (5.69 g, 26.1 mmol) was then added. The reaction mixture was stirred at room temperature for 18 h, and then concentrated under reduced pressure to remove the solvent. The residue was purified by silica gel column chromatography (eluent: DCM/MeOH 30:1→15:1) to give compound 32 (2.3 g) as pale yellow oil.

LC-MS (method 1): Rt=1.41 min; m/z (ES+) 316.1 (M+Na)$^+$.

Step 2: Synthesis of tert-butyl bis(2-(2-(tosyloxy)ethoxy)ethyl)carbamate (33)

Compound 32 (2.3 g, 7.85 mmol) and TEA (3.17 g, 31.4 mmol) were dissolved in DCM (40 mL), to which TsCl (4.49 g, 23.6 mmol) was then added slowly. The reaction mixture was stirred at room temperature for 18 h, and then concentrated under reduced pressure to remove the solvent. The residue was purified by silica gel column chromatography (eluent: PE/EA 3:1) to give compound 33 (3.3 g) as colorless oil.

LC-MS (method 4): Rt=1.88 min; m/z (ES+) 624.2 (M+Na)$^+$.

Step 3: Synthesis of bis(2-(2-(tosyloxy)ethoxy)ethyl)amine (34)

Compound 33 (3.3 g, 5.49 mmol) was dissolved in DCM (9 mL), and the reaction mixture was cooled down to 0° C., to which TFA (3 mL) was then slowly added. The reaction mixture was stirred at room temperature for 2 h, and then concentrated under reduced pressure to remove the solvent. The residue was dissolved in DCM, and washed with saturated sodium bicarbonate. The aqueous phase was extracted by DCM (10 mL), and the combined organic phase was dried over anhydrous sodium sulfate, filtered, and concentrated under reduced pressure to give compound 34 (2.5 g) as colorless oil. The crude product was used directly in next step without purification.

Step 4: Synthesis of 4-(bis(2-(2-(tosyloxy)ethoxy)ethyl)amino)-4-oxobutanoic Acid (35)

Compound 34 (2.5 g, 4.99 mmol) was dissolved in DCM (15 mL), to which succinic anhydride (0.75 g, 7.48 mmol) and DIPEA (1.93 g, 15.0 mmol) were added sequentially. The reaction mixture was stirred at room temperature for 2 h, and then washed with water (20 mL). The organic phase was dried over anhydrous sodium sulfate, filtered, and concentrated under reduced pressure to give colorless oil. Further purification by silica gel column chromatography (eluent: DCM/MeOH 20:1) gave compound 35 (1.6 g) as colorless oil.

LC-MS (method 4): Rt=1.64 min; m/z (ES+) 602.1 (M+H)$^+$.

Step 5: Synthesis of 4-(bis(2-(2-azidoethoxy)ethyl)amino)-4-oxobutanoic Acid (36)

Compound 35 (1.6 g, 2.66 mmol) was dissolved in DMF (10 mL), to which sodium azide (0.52 g, 7.99 mmol) was then added. The reaction mixture was stirred at 50° C. for 5 h, and then concentrated under reduced pressure to remove the solvent. The residue was purified by silica gel column chromatography (eluent: DCM/MeOH 20:1) to give compound 36 (600 mg) as colorless oil.

LC-MS (method 1): Rt=1.55 min; m/z (ES+) 344.1 (M+H)$^+$.

Step 6: Synthesis of 4-(bis(2-(2-aminoethoxy)ethyl)amino)-4-oxobutanoic Acid (37)

Compound 36 (600 mg, 1.75 mmol) was dissolved in THF (10 mL) and water (126 µL), to which triphenylphosphine (1.37 g, 5.25 mmol) was then added. The reaction mixture was stirred at room temperature for 18 h, while insoluble oil was found on the flask wall and bottom. THF was carefully removed, and the colorless oil was washed with THF (3 mL×3) and then added with water (10 mL). The solution was lyophilized to give compound 37 (500 mg) as a white solid.

LC-MS (method 5): Rt=0.35, 0.46 min; m/z (ES+) 292.1 (M+H)$^+$.

Step 7: Synthesis of Compound 9

Compound 37 (20 mg, 68 µmol) and compound 16 (53 mg, 137 µmol) were dissolved in DMF (0.6 mL), to which DIPEA (71 mg, 548 µmol) was then added. The reaction mixture was stirred at room temperature for 2 h, and then purified by RP-HPLC (method 6: 30%-60% B in 8 min→95% B in 4) to give compound 9 (9 mg) as a white solid.

LC-MS (method 2): Rt=1.61 min; m/z (ES+) 840.0 (M+H)⁺.

¹H NMR (500 MHz, DMSO-d₆) δ 7.83-7.79 (m, 2H), 7.00 (s, 4H), 6.97 (s, 4H), 4.00-3.94 (m, 2H), 3.79-3.74 (m, 2H), 3.60-3.56 (m, 2H), 3.50-3.47 (m, 4H), 3.39 (s, 4H), 3.36-3.29 (m, 4H), 3.15-3.09 (m, 4H), 2.55 (t, 2H), 2.39 (t, 2H), 2.21-2.14 (m, 2H), 2.03-2.01 (m, 4H), 1.95-1.88 (m, 2H).

Example 10

Synthesis of Compound 10 (Linker 10)

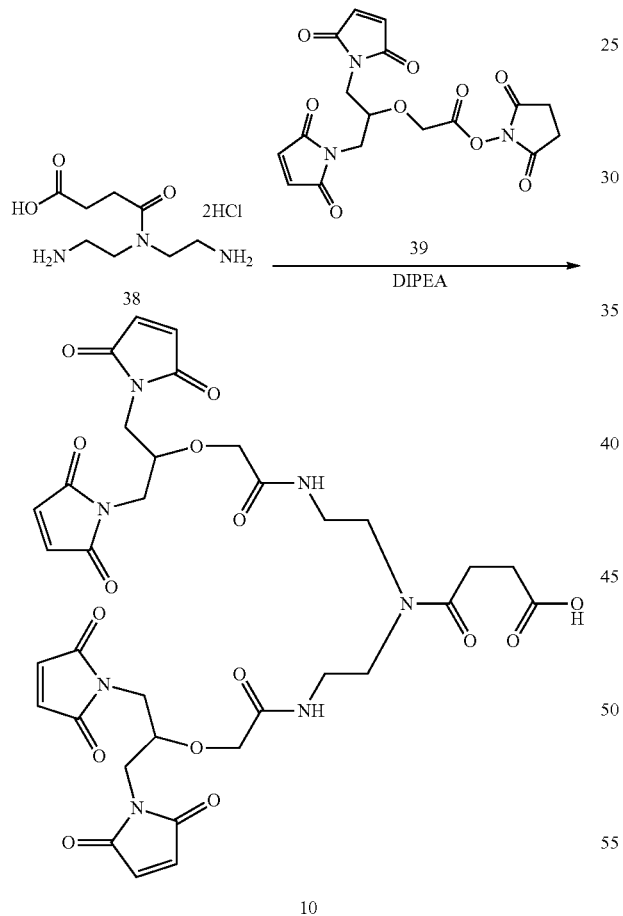

10

Compound 38 (15 mg, 54 µmol, prepared according to WO2014114207) and compound 39 (44 mg, 108 µmol, prepared according to WO2014114207) were dissolved in DMF (0.6 mL), to which DIPEA (28 mg, 216 µmol) was then added. The reaction mixture was stirred at room temperature for 2 h, and then purified by RP-HPLC (method 6: 37%-58% B in 8 min→95% B in 4) to give compound 10 (15 mg) as a white solid.

LC-MS (method 2): Rt=1.63 min; m/z (ES+) 784.0 (M+H)⁺.

¹H NMR (500 MHz, DMSO-d₆) δ11.98 (br s, 1H), 7.59 (t, 1H), 7.44 (t, 1H), 7.05 (s, 8H), 3.88 (s, 2H), 3.85 (s, 2H), 3.82-3.77 (m, 2H), 3.52-3.50 (m, 8H), 3.29-3.19 (m, 6H), 3.15-3.12 (m, 2H), 2.49 (t, 2H), 2.41 (t, 2H).

Example 11

Synthesis of Compound 11 (Linker 11)

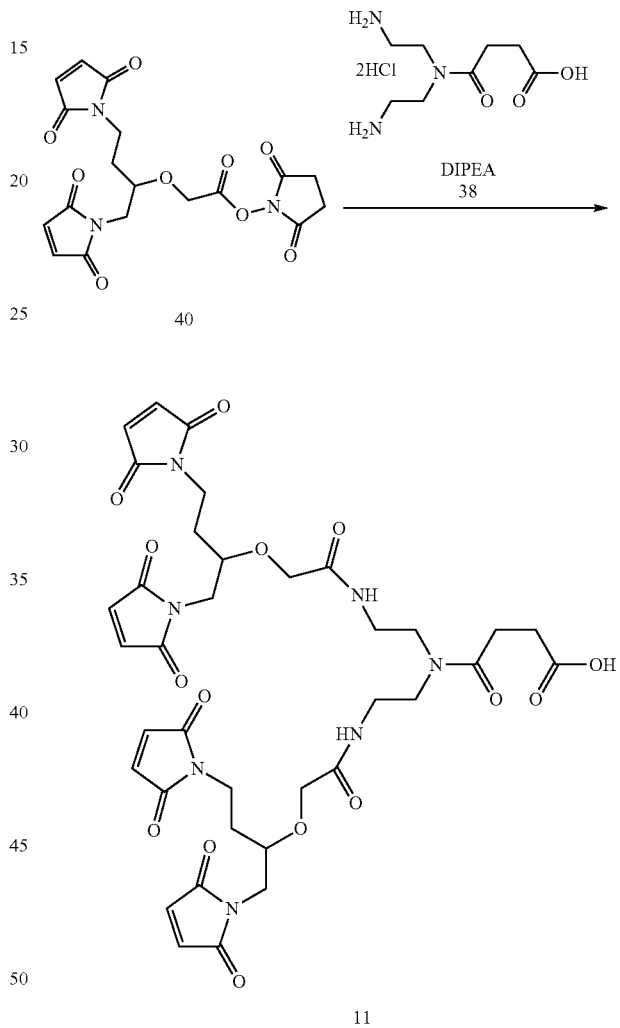

11

Compound 38 (15 mg, 54 µmol) and compound 40 (45 mg, 108 µmol, prepared according to WO2014114207) were dissolved in DMF (0.5 mL), to which DIPEA (28 mg, 216 µmol) was then added. The reaction mixture was stirred at room temperature for 2 h, and then purified by RP-HPLC (method 6: 38%-58% B in 8 min→95% B in 4) to give compound 11 (14 mg) as a white solid.

LC-MS (method 2): Rt=1.65 min; m/z (ES+) 812.0 (M+H)⁺.

¹H NMR (500 MHz, DMSO-d₆) δ12.01 (br s, 1H), 7.75 (t, 1H), 7.62 (t, 1H), 7.04 (s, 4H), 7.00 (s, 4H), 4.02-3.95 (m, 2H), 3.84-3.79 (m, 2H), 3.58-3.45 (m, 10H), 3.33-3.19 (m, 8H), 2.53 (t, 2H), 2.40 (t, 2H), 1.66-1.56 (m, 4H).

Example 12

Synthesis of Compound 12 (Linker 12)

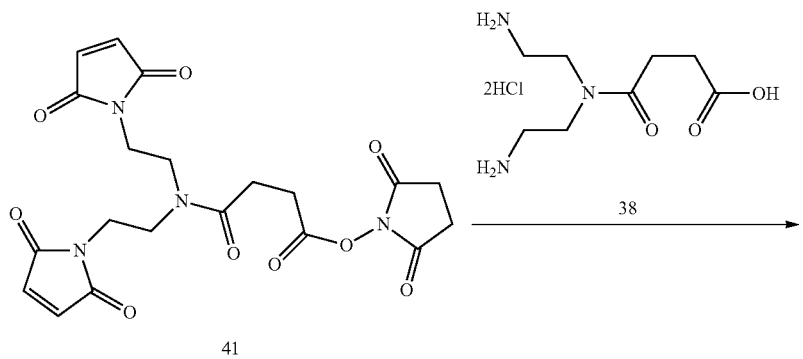

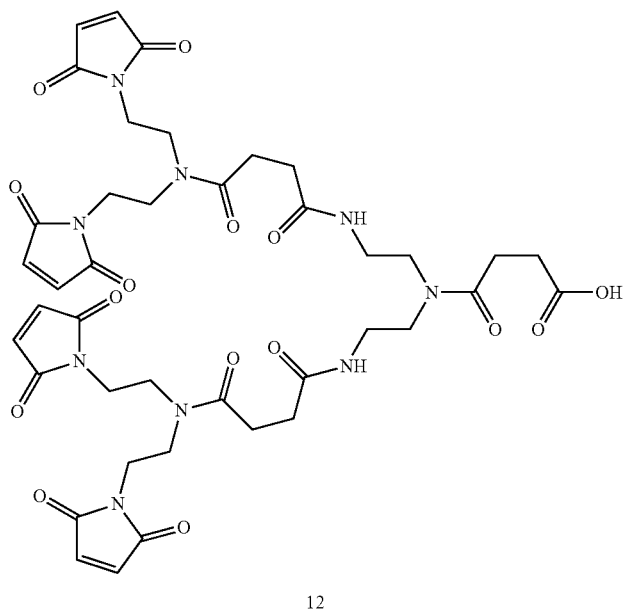

Compound 38 (15 mg, 54 μmol) and compound 41 (50 mg, 108 μmol, prepared according to WO2014114207) were dissolved in DMF (0.5 mL), to which DIPEA (28 mg, 216 μmol) was then added. The reaction mixture was stirred at room temperature for 2 h, and then purified by RP-HPLC (method 6: 35%-60% B in 8 min→95% B in 4 min) to give compound 12 (14 mg) as a white solid.

LC-MS (method 2): Rt=1.58 min; m/z (ES+) 894.0 (M+H)$^+$.

$^1$H NMR (500 MHz, DMSO-d$_6$) δ7.97 (t, 1H), 7.82 (t, 1H), 7.04 (s, 4H), 6.96 (s, 4H), 3.58 (t, 4H), 3.52 (t, 4H), 3.39-3.38 (m, 8H), 3.29 (t, 2H), 3.23 (t, 2H), 3.19-3.16 (m, 2H), 3.12-3.08 (m, 2H), 2.51-2.50 (m, 2H), 2.41 (t, 2H), 2.35-2.32 (m, 4H), 2.23-2.18 (m, 4H).

Example 13

Synthesis of Compound 13 (Linker 13)

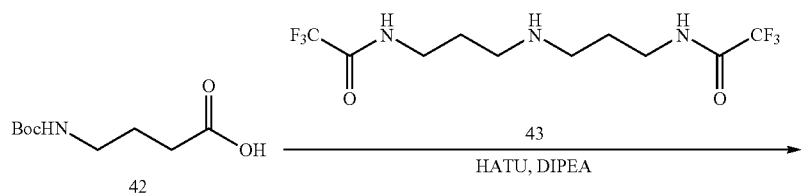

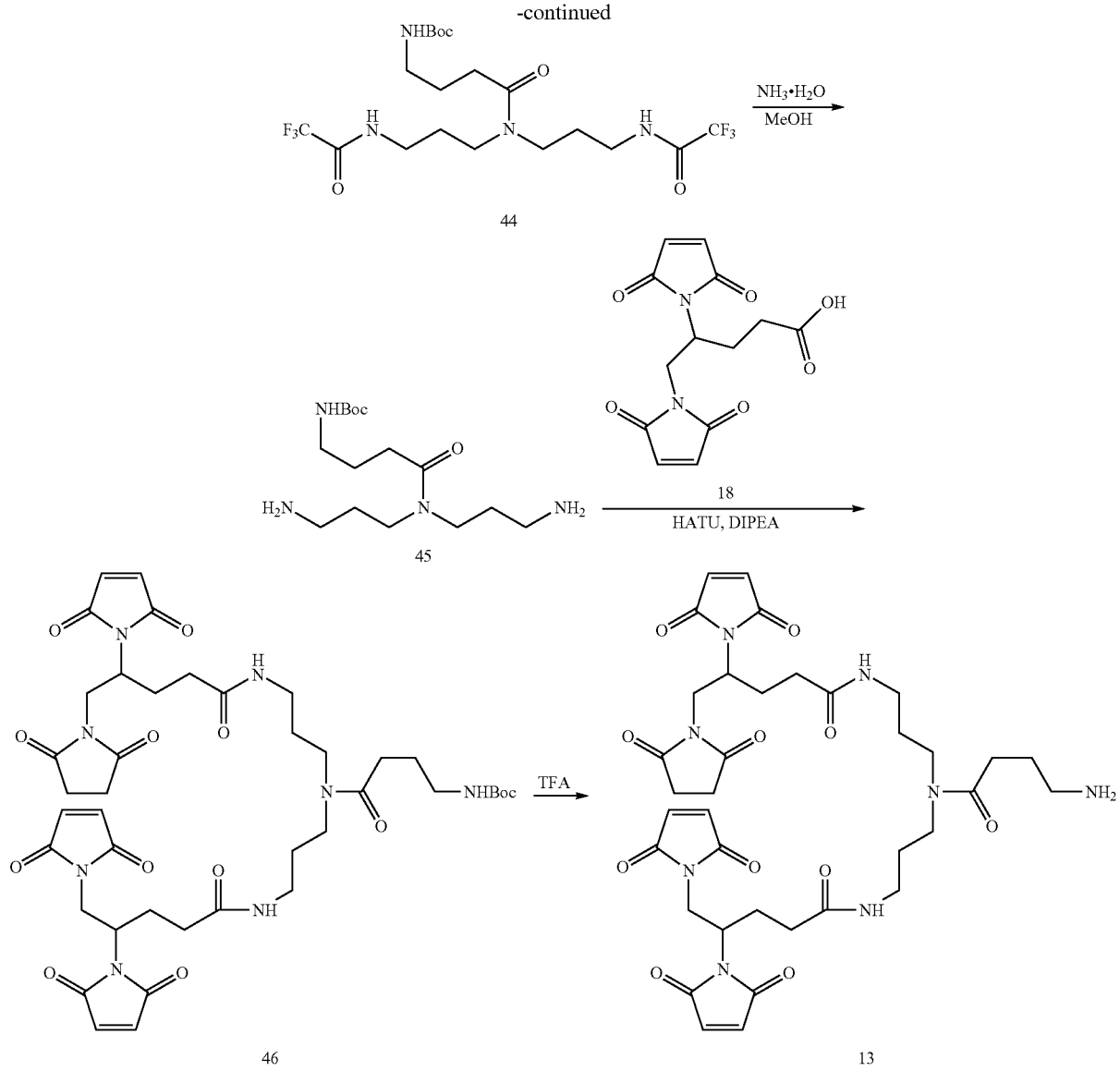

Step 1: Synthesis of tert-butyl 4-(bis(3-(2,2,2-trifluoroacetamido)propyl)amino)-4-oxobutylcarbamate (44)

4-(Tert-butoxycarbonylamino)butanoic acid (42) (203 mg, 1.0 mmol, prepared according to US2015/111864) and bis(3-(2,2,2-trifluoroacetamido)propyl)amine (43) (388 mg, 1.2 mmol, prepared according to WO2006/20779) were dissolved in DMF (3 mL), to which HATU (456 mg, 1.2 mmol) and DIPEA (258 mg, 2 mmol) were then added. The reaction mixture was stirred at room temperature for 3 h, and then concentrated. The residue was purified by RP-HPLC (method 6: 45%-75% B in 8 min→95% B in 4 min) to give compound 44 (250 mg) as a colorless colloidal solid.

LC-MS (method 1): Rt=1.81 min; m/z (ES+) 409.0 (M+H)+.

$^1$H NMR (500 MHz, CDCl$_3$) δ 8.34 (br s, 1H), 7.949 (s, 1H), 5.03 (br s, 1H), 3.42-3.30 (m, 4H), 3.30-3.17 (m, 4H), 3.09 (s, 2H), 2.39-2.27 (m, 2H), 1.91-1.82 (m, 2H), 1.82-1.73 (m, 2H), 1.73-1.63 (m, 2H), 1.37 (s, 9H).

Step 2 and 3: Synthesis of tert-butyl 4-(bis(3-(4,5-bis(2,5-dioxo-2,5-dihydro-1H-pyrrol-1-yl)pentanamido)propyl)amino)-4-oxobutylcarbamate (46)

Compound 44 (20 mg, 39 μmol) was dissolved in methanol (1 mL), to which aqueous ammonia (28%, 1 mL) was then added. The reaction mixture was refluxed for 4 h, and then concentrated to remove the solvent. The residue was dissolved in methanol again and concentrated (repeated three times).

The thus-obtained intermediate 45 was dissolved in DMF (1 mL) and DCM (1 mL), to which compound 18 (35 mg, 0.12 mmol), HATU (60 mg, 0.158 mmol) and DIPEA (30 mg, 0.23 mmol) were then sequentially added. The reaction mixture was stirred at room temperature for 2 h, and then concentrated to remove the solvent. The residue was purified by RP-HPLC (method 6: 50%-80% B in 8 min→95% B in 4 min) to give compound 46 (20 mg) as a white solid.

LC-MS (method 3): Rt=1.33 min; m/z (ES+) 865.5 (M+H)+.

$^1$H NMR (500 MHz, DMSO-d$_6$) δ7.81 (t, 1H), 7.72 (t, 1H), 7.00 (s, 4H), 6.98 (s, 2H), 6.97 (s, 2H), 6.80 (t, 1H), 4.02-3.94 (m, 2H), 3.82-3.73 (m, 2H), 3.64-3.54 (m, 2H), 3.24-3.10 (m, 4H), 3.05-2.85 (m, 6H), 2.26-2.12 (m, 4H), 2.08-1.86 (m, 6H), 1.63-1.43 (m, 6H), 1.37 (s, 9H).

Step 4: Synthesis of Compound 13

Compound 46 (20 mg, 23 μmol) was dissolved in DCM (3 mL), to which TFA (1 mL) was then added. The reaction mixture was stirred at room temperature for 1 h, and then concentrated to remove the solvent. The residue was purified by RP-HPLC (method 6: 30%-60% B in 8 min→95% B in 4 min) to give compound 13 in TFA salt form (10 mg) as a white solid.

LC-MS (method 2): Rt=1.46 min; m/z (ES+) 765.0 (M+H)$^+$.

$^1$H NMR (500 MHz, DMSO-d$_6$) δ 7.83 (t, 1H), 7.78-7.68 (m, 4H), 7.01 (s, 4H), 6.99 (s, 2H), 6.98 (s, 2H), 4.02-3.94 (m, 2H), 3.82-3.74 (m, 2H), 3.63-3.55 (m, 2H), 3.19 (t, 4H), 3.06-2.88 (m, 4H), 2.86-2.77 (m, 2H), 2.37 (t, 2H), 2.26-2.12 (m, 2H), 2.09-1.87 (m, 6H), 1.80-1.71 (m, 2H), 1.64-1.46 (m, 4H).

Example 14

Synthesis of Compound 14 (Linker 14)

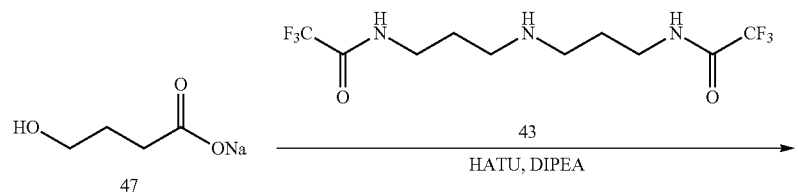

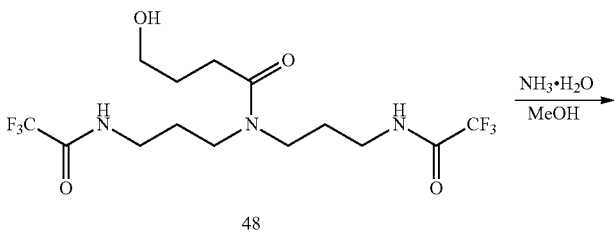

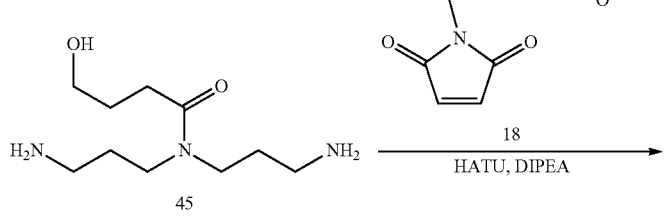

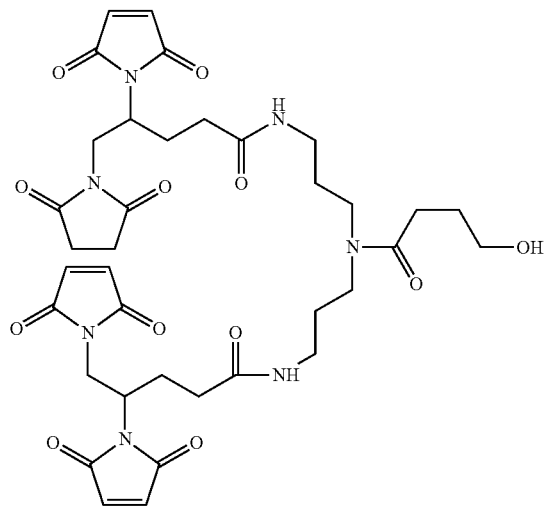

14

Step 1: Synthesis of 4-hydroxy-N,N-bis(3-(2,2,2-trifluoroacetamido)propyl)butanamide (48)

Sodium 4-hydroxybutanoate (47) (126 mg, 1.0 mmol, prepared according to WO2014/152127) and bis(3-(2,2,2-trifluoroacetamido)propyl)amine 43 (388 mg, 1.2 mmol) were dissolved in DMF (3 mL), to which HATU (456 mg, 1.2 mmol) and DIPEA (258 mg, 2 mmol) were then added. The reaction mixture was stirred at room temperature for 3 h, and then concentrated. The residue was purified by RP-HPLC (method 6: 40%-70% B in 8 min→95% B in 4 min) to give compound 48 (68 mg) as a colorless colloidal solid.

LC-MS (method 5): Rt=1.55 min; m/z (ES+) 410.0 (M+H)+.

$^1$H NMR (500 MHz, DMSO-d$_6$) δ9.48 (t, 1H), 9.37 (t, 1H), 3.39 (t, 2H), 3.31-3.05 (m, 8H), 2.29 (t, 2H), 1.81-1.70 (m, 2H), 1.70-1.57 (m, 4H).

Step 2, 3: Synthesis of Compound 14

Compound 48 (20 mg, 49 μmol) was dissolved in methanol (1 mL), to which aqueous ammonia (28%, 1 mL) was then added. The reaction mixture was refluxed for 2 h, and then concentrated to remove the solvent. The residue was dissolved in methanol again and concentrated, while such process was repeated three times.

The thus-obtained intermediate 49 was dissolved in DMF (1 mL) and DCM (1 mL), to which compound 18 (43 mg, 0.15 mmol), HATU (74 mg, 0.20 mmol) and DIPEA (38 mg, 0.29 mmol) were then sequentially added. The reaction mixture was stirred at room temperature for 2 h, and then concentrated to remove the solvent. The residue was purified by RP-HPLC (method 6: 35%-65% B in 8 min→95% B in 4 min) to give compound 14 (5 mg) as a white solid.

LC-MS (method 2): Rt=1.62 min; m/z (ES+) 765.9 (M+H)+.

$^1$H NMR (500 MHz, DMSO-d$_6$) δ7.82 (t, 1H), 7.72 (t, 1H), 7.00 (s, 4H), 6.98 (s, 2H), 6.97 (s, 2H), 4.02-3.94 (m, 2H), 3.82-3.73 (m, 2H), 3.62-3.56 (m, 2H), 3.37 (t, 2H), 3.24-3.13 (m, 4H), 3.03-2.87 (m, 4H), 2.26 (t, 2H), 2.23-2.13 (m, 2H), 2.08-1.87 (m, 6H), 1.68-1.43 (m, 6H).

Example 15

Synthesis of Tetramaleimide Linker-Drug (1-vcMMAE)

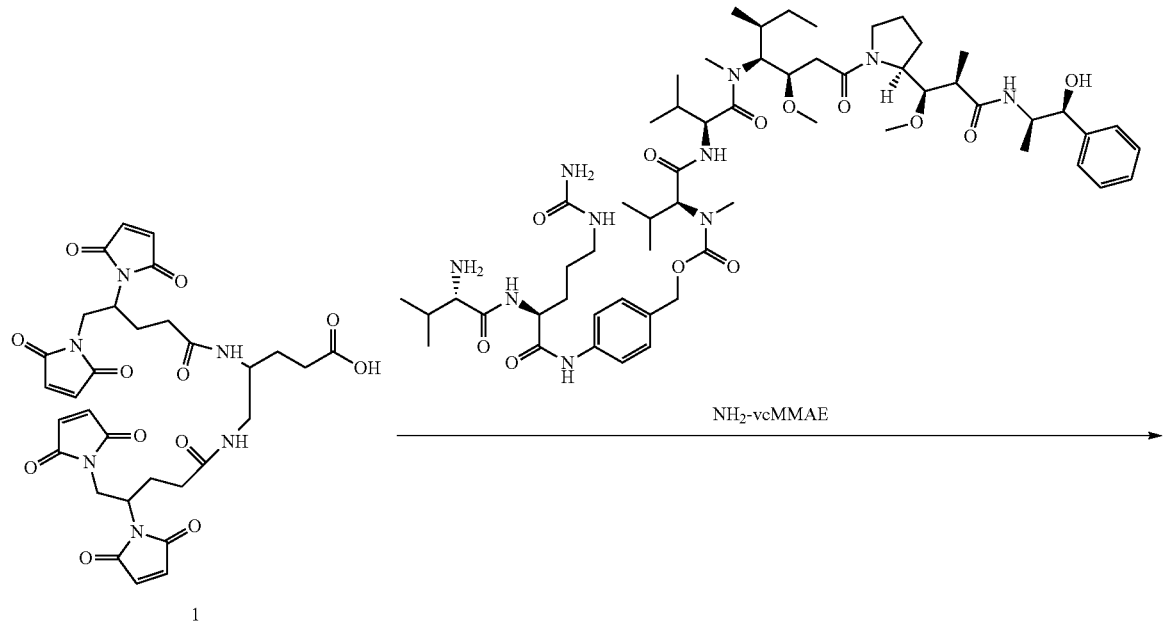

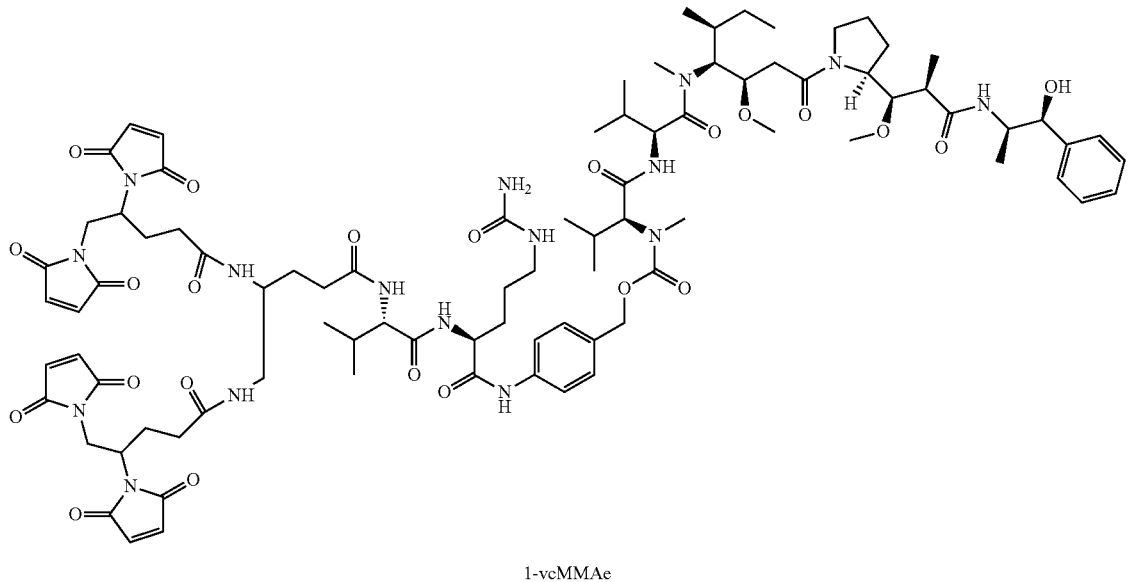

1-vcMMAe

Compound 1 (4.1 mg, 6 μmol) and NH$_2$-vcMMA (TFA salt, 6.7 mg, 6 mol, prepared according to WO2013/173337) were dissolved in DMF (300 μL), to which DIPEA (2.3 mg, 9 μmol) and HATU (3.4 mg, 9 μmol) were then sequentially added. The reaction mixture was stirred at room temperature for 18 h, and then purified by prep-RP-HPLC (method 6: 45%-75% B in 8 min→95% B in 4 min) to give compound 1-vcMMAE (4.8 mg) as white powder.

LC-MS (method 2): R$_f$=1.84 min; m/z (ES$^+$) 892.8 [½ (M+2H)]$^+$.

Example 16

Synthesis of Other Tetramaleimide Linker-Drug

Other tetramaleimide linker-drugs were synthesized via the similar method as that for 1-vcMMAE in example 15, except that compound 1 was replaced with linker compounds 2-12. The linker-drugs and their characterization data were listed in Table 1, wherein the linker-drug 2-vcMMAE to 12-vcMMAE were named according to the tetramaleimide linker compounds 2 to 12.

TABLE 1

Linker-drugs of the invention and their characterizations

| Compound | LC-MS<br>Method; $R_t$ (min); m/z 1/2[M + 2H]$^+$ |
|---|---|
| 2-vcMMAE | 2; 1.90; 900.9 |
| 3-vcMMAE | 2; 2.02; 903.5 |
| 4-vcMMAE | 4; 1.56; 908.9 |
| 5-vcMMAE | 2; 1.82; 935.3 |
| 6-vcMMAE | 2; 1.95; 936.0 |
| 7-vcMMAE | 2; 1.95; 943.1 |
| 8-vcMMAE | 2; 1.87; 947.3 |
| 9-vcMMAE | 4; 1.55; 973.0 |
| 10-vcMMAE | 4; 1.56; 945.5 |
| 11-vcMMAE | 4; 1.57; 959.0 |
| 12-vcMMAE | 4; 1.53; 1000.5 |

Example 17

Preparation and Characterization of Antibody-Drug Conjugates

Tris(2-carboxyethyl)phosphine (TCEP, 10 eq, stock solution 10 mM) was added to a solution of antibody H (IgG1) (2-10 mg/mL, containing 25 mM boric acid-sodium borate buffer, 25 mM NaCl and 1 mM diethylene triamine pentacetic acid (DTPA), pH 7.0-8.0). The reaction mixture was incubated at 37° C. in a shaker for 2 h, and then cooled to ~10° C., followed by buffer-exchange with a PBS buffer (100 mM $KH_2PO_4$—$K_2HPO_4$, 100 mM NaCl, 1 mM DTPA, pH 7.0-8.0) via ultrafiltration (Merck Millipore Amicon® Ultra, 50000 MWCO) or gel-filtration. The solution was cooled at 10° C., to which DMSO and compound 1-vcMMAE prepared in example 15 (stock solution in DMSO, 3-6 equivalent) were sequentially added, in which the volume percent of DMSO was controlled at ~15%. The conjugation reaction was conducted at 10° C. for 0.5 h.

Excess cysteine solution was added to the reaction mixture to quench the unreacted compound 1-vcMMAE, and the quenching reaction was kept at 10° C. for 30 min. The reaction mixture was ultrafiltered (Merck Millipore Amicon® Ultra, 50000 MWCO) or gel-filtered to remove excess 1-vcMMAE-cysteine adducts and excess cysteine. The filtrate was sterile filtered through 0.22 μm filter (Merck Millex-GV Filter), and the solution of conjugate H-1-vcMMAE thus obtained was kept at 4° C.

Conjugates H-2-vcMMAE to H-12-vcMMAE were prepared from antibody H according to the same method as above, except for replacing compound 1-vcMMAE with compounds 2-vcMMAE to 12-vcMMAE. Conjugate P-7-vcMMAE was prepared from antibody P according to the same method as above, except for replacing compound 1-vcMMAE with compound 7-vcMMAE.

1) Determination of Average DAR

The average DAR was measured by UV absorption method (Clin. Cancer Res. 2004, 10, 7063-7070; WO 2011/039721). Agilent 1100 HPLC with the size-exclusion chromatography (SEC) column (TSKgel G3000SWXL, 7.8*300 mm, Tosoh Bioscience Shanghai) was used.

$$DAR=(\varepsilon_{Ab248}-R*\varepsilon_{Ab280})/(R*\varepsilon_{D280}-\varepsilon_{D248})$$

wherein, $\varepsilon_{Ab248}$ and $\varepsilon_{Ab280}$ are molar extinction coefficients for the antibody at 248 nm and 280 nm, respectively. $\varepsilon_{D280}$ and $\varepsilon_{D248}$ are molar extinction coefficients for vcMMAE at 248 nm and 280 nm, respectively. $R=A_{248}/A_{280}$, wherein $A_{248}$ and $A_{280}$ are the absorbances of the ADC at 248 nm and 280 nm, respectively (peak area of the monomer on SEC spectrum was used to represent the absorbance in the invention).

The average DARs of the ADCs of the invention were listed in table 2.

TABLE 2

The average DAR results of the ADCs in the invention (equivalent ratio of the linker-drug to antibody was 3)

| ADC | Average DAR | ADC | Average DAR |
|---|---|---|---|
| H-1-vcMMAE | 1.99 | H-7-vcMMAE | 1.99 |
| H-2-vcMMAE | 1.99 | H-8-vcMMAE | N/A |
| H-3-vcMMAE | N/A | H-9-vcMMAE | 1.96* |
| H-4-vcMMAE | 1.96 | H-10-vcMMAE | 2.46* |
| H-5-vcMMAE | 2.05 | H-11-vcMMAE | 2.75 |
| H-6-vcMMAE | 1.88 | H-12-vcMMAE | 2.51 |
| P-7-vcMMAE | 2.20*& | | |

N/A: not available.
*equivalent ratio of the linker-drug to antibody was 4.
&DAR was calculated from HIC method, see reference Anal. Chem. 2013, 85, 1699-1704.

As shown in table 2, the average DARs of the ADCs of the invention could be well-controlled around 2, which is due to the accurate site and number control by the site-specific linkers of the invention.

2) Native MS

8 μL of PNGase F (New England Biolabs, USA) was added to 400 μg of conjugate H-5-vcMMAE, and the mixture was incubated at 37° C. overnight (15 h). The deglycosylated ADC sample was buffer-exchanged into ammonium acetate buffer (20 mM, pH 7.0), and the buffer exchange procedure was repeated for 5 times.

The mass spectrometer used was high-resolution Orbitrap Exactive Plus EMR (Thermo Fisher Scientific, Germany), and the ion source is TriVersa NanoMate® (Advion, USA). The sample concentration was adjusted to 2 μg/μL, and direct injection was adopted. The mass data was collected under the positive ion mode, and the native mass data was analyzed by Protein Deconvolution 4.0 software (Thermo Fisher Scientific, Germany).

The native MS spectrum of conjugate H-5-vcMMAE was shown in FIG. 1, which shows that DAR=2 was the main component of the product.

3) SDS-PAGE

SDS-PAGE was measured using NuPAGE™, 4-12%, Bis-Tris Gel (Thermal Fisher) on XCell SureLock® Mini-Cell protein electrophoresis instrument (Thermal Fisher). A sample (≥10 μg by weight) was combined with loading buffer, and the mixture was heated at 70° C. in water bath for 10 min. The sample and standard protein (5 μL/hole) were added to the spacer gel comb holes sequentially, and the electrophoresis was conducted at 220 V for 50 min. The gel was removed, rinsed by deionized water, and then stained in SimplyBlue™ SafeStain (Thermal Fisher) on a shaker for 3 h. The stained gel was rinsed by deionized water for three times, and destained on a shaker for 4 h. The destained gel was transferred to an imager to record the gel image.

Figure 2A:
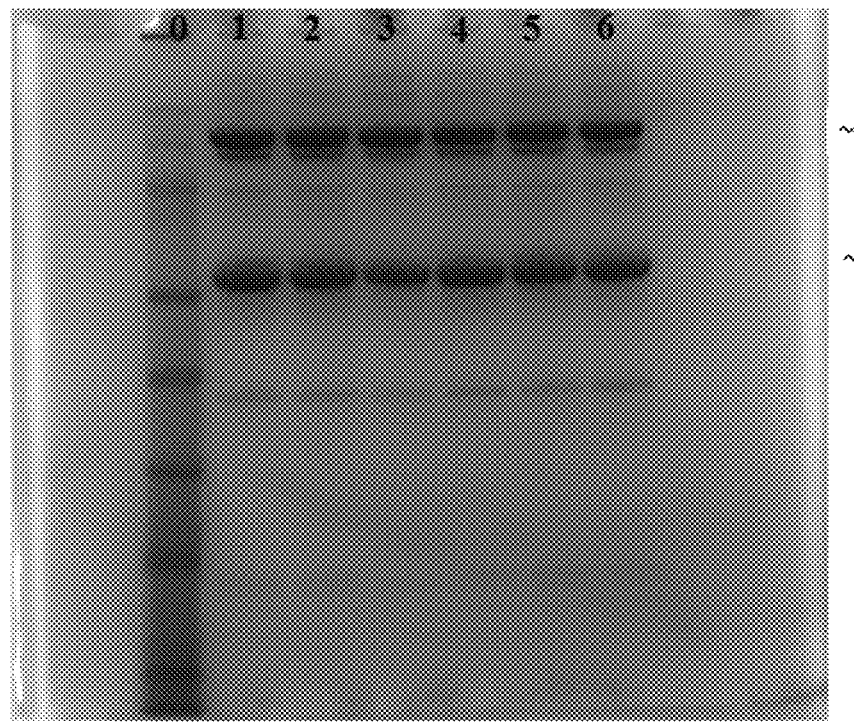
FIGS. 2a-2b illustrate the SDS-PAGE results of the antibody-drug conjugates based on tetramaleimide linkers, wherein 2a represents the SDS-PAGE result of H-1-vcM-MAE to H-6-vcMMAE (corresponding to 1-6 respectively); 2b represents the SDS-PAGE result of H-7-vcMMAE to H-12-vcMMAE (corresponding to 7-12 respectively).
Figure 2B:
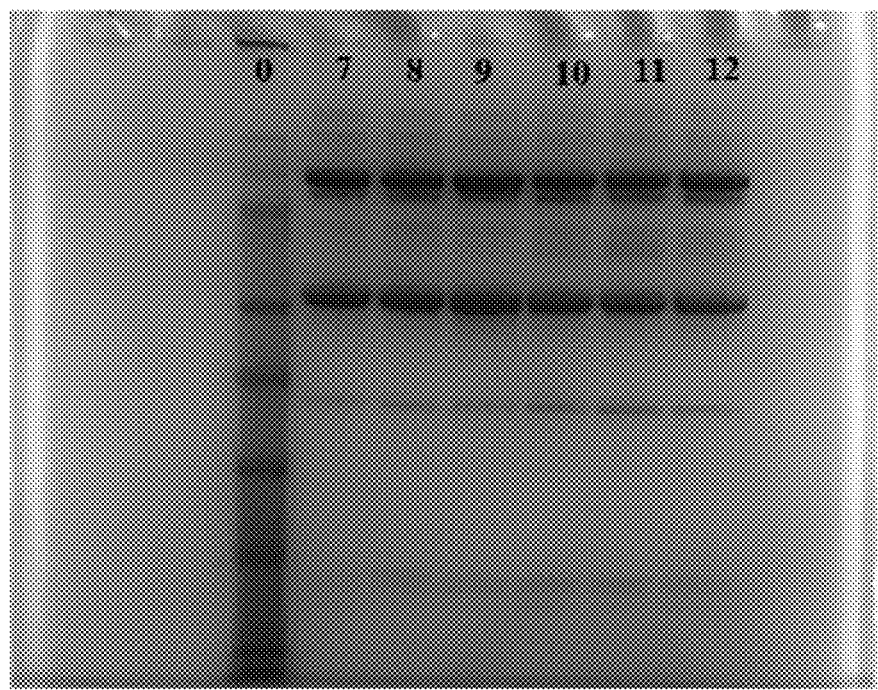
Figure 3A:
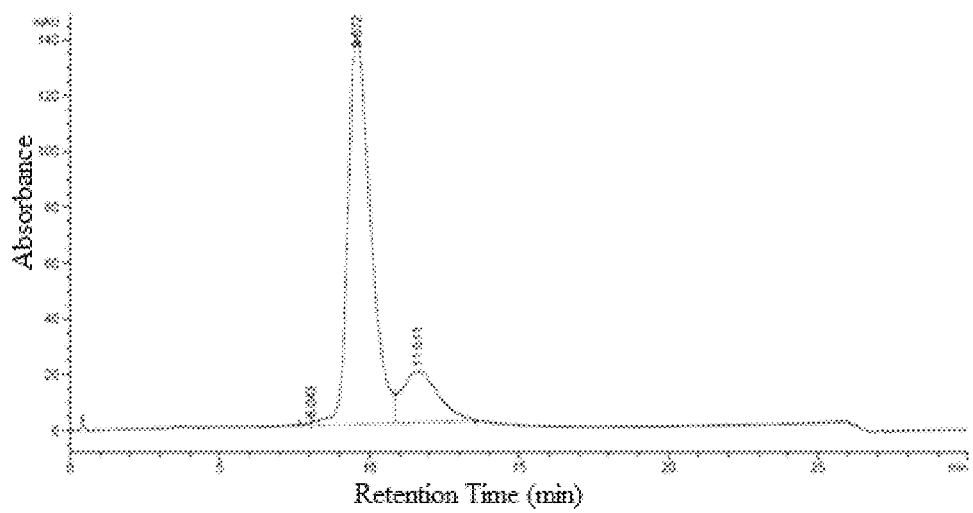
FIGS. 3a-3l illustrate the HIC results of the antibody-drug conjugates, wherein 3a-3l correspond to H-1-vcMMAE to H-12-vcMMAE respectively; 3m corresponds to P-7-vcM-MAE.
Figure 3B:
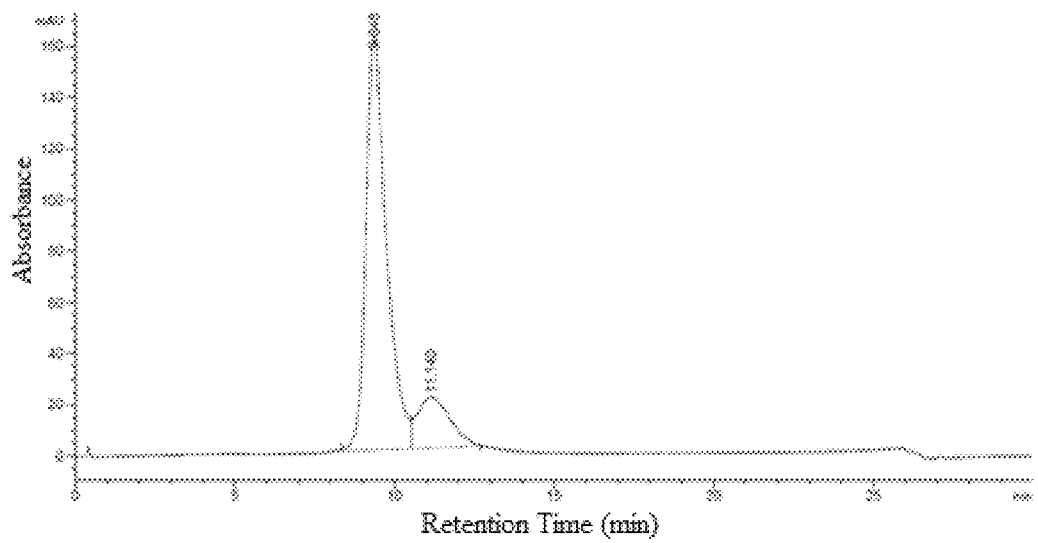
Figure 3C:
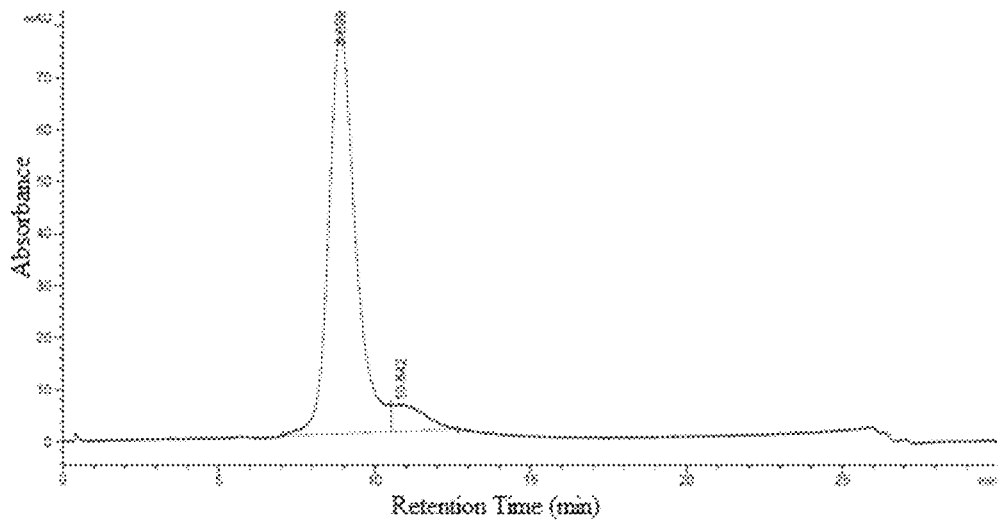
Figure 3D:
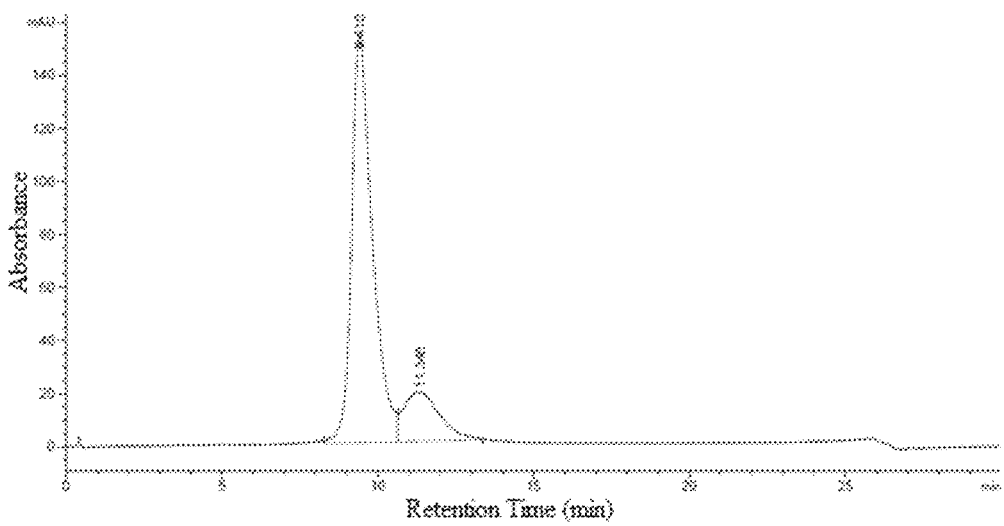
Figure 3E:
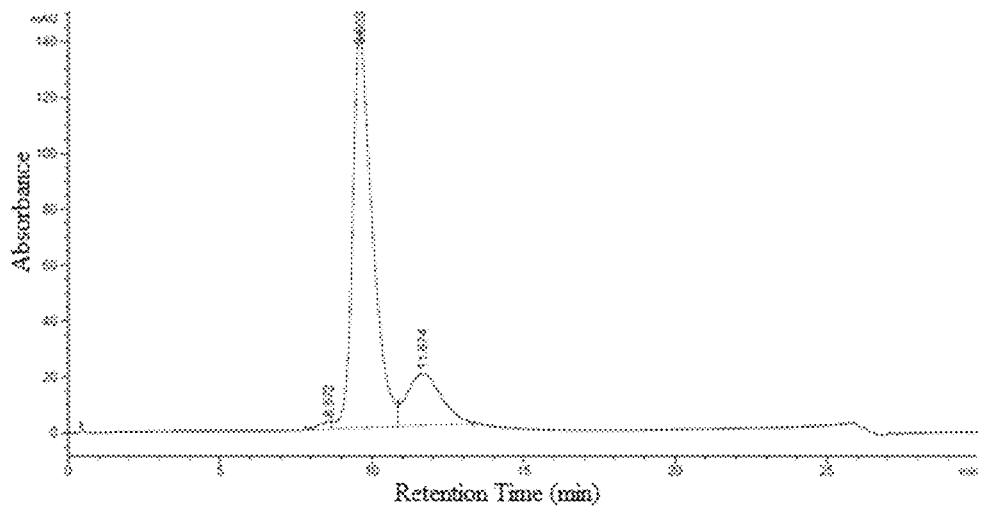
Figure 3F:
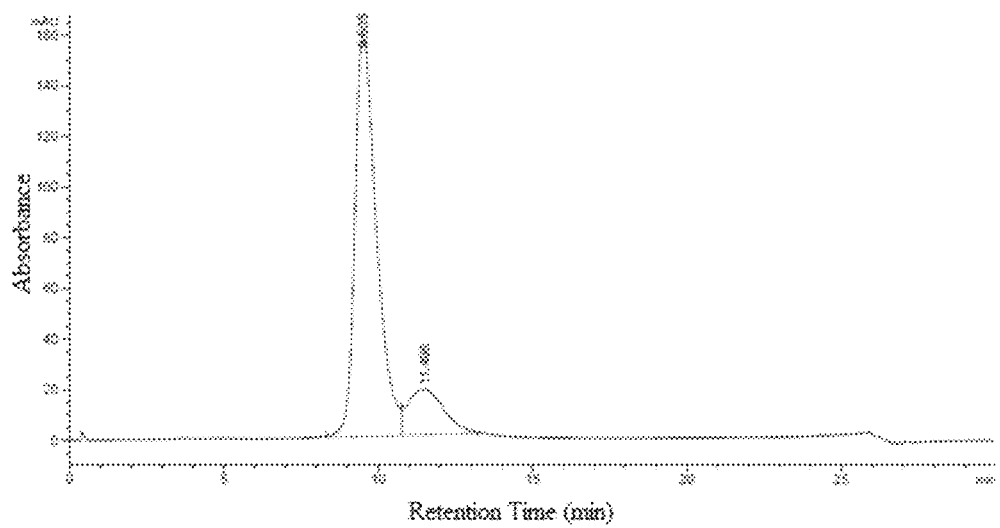
Figure 3G:
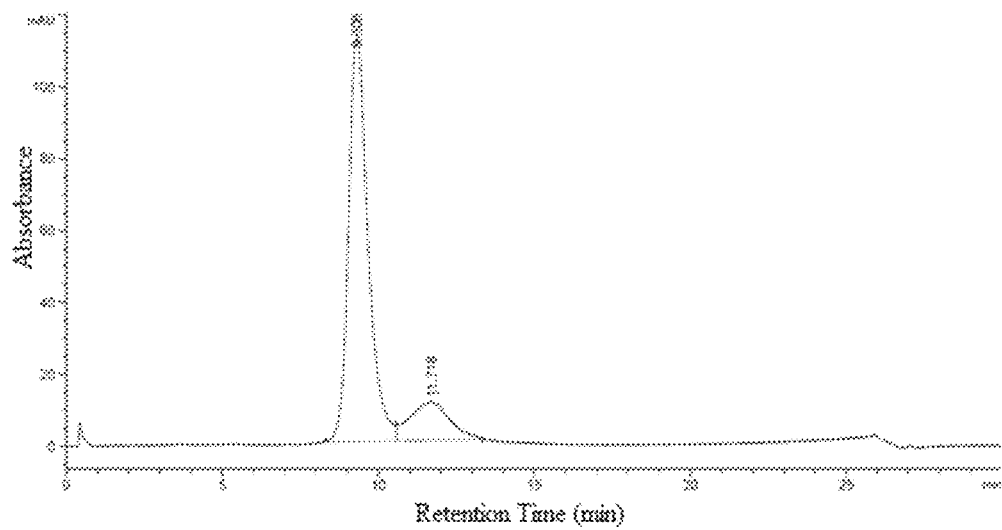
Figure 3H:
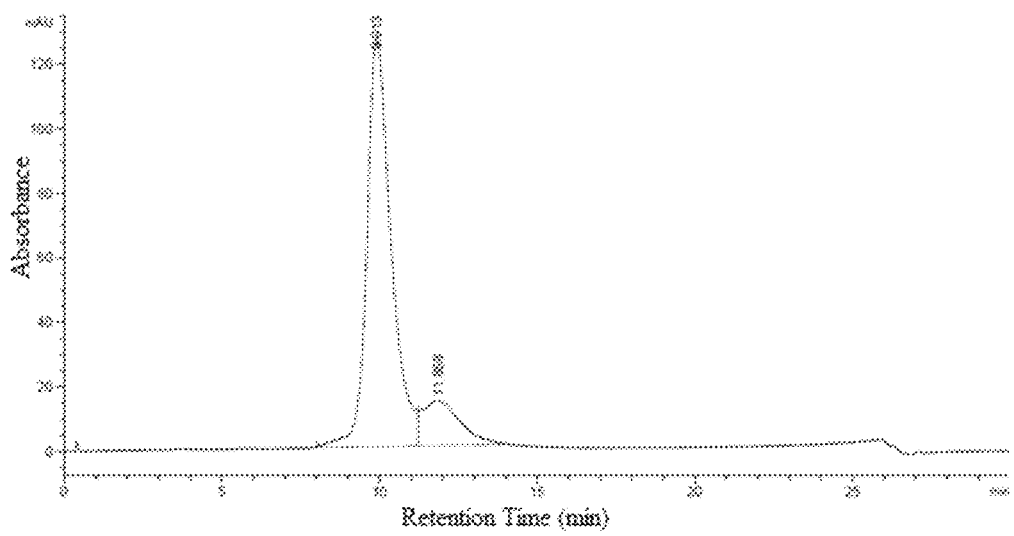
Figure 3I:
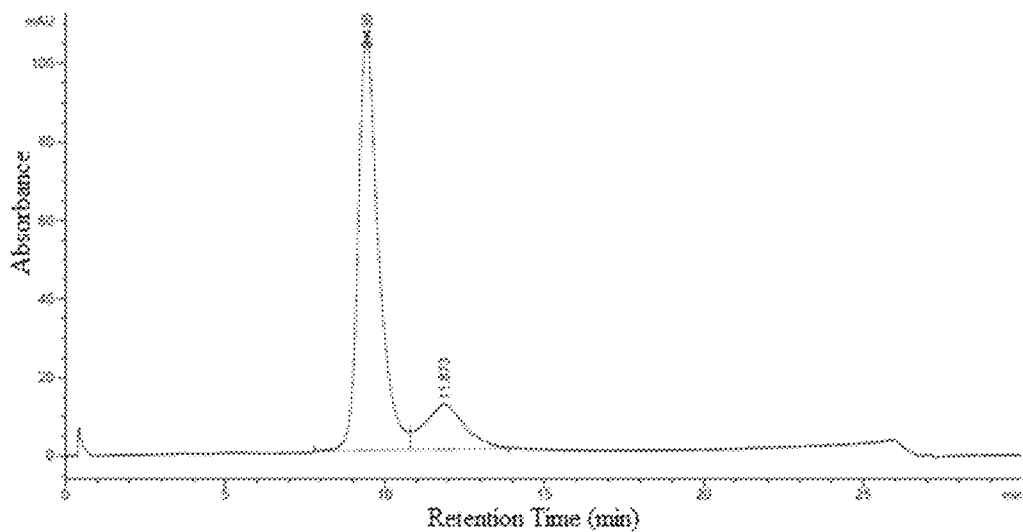
Figure 3J:
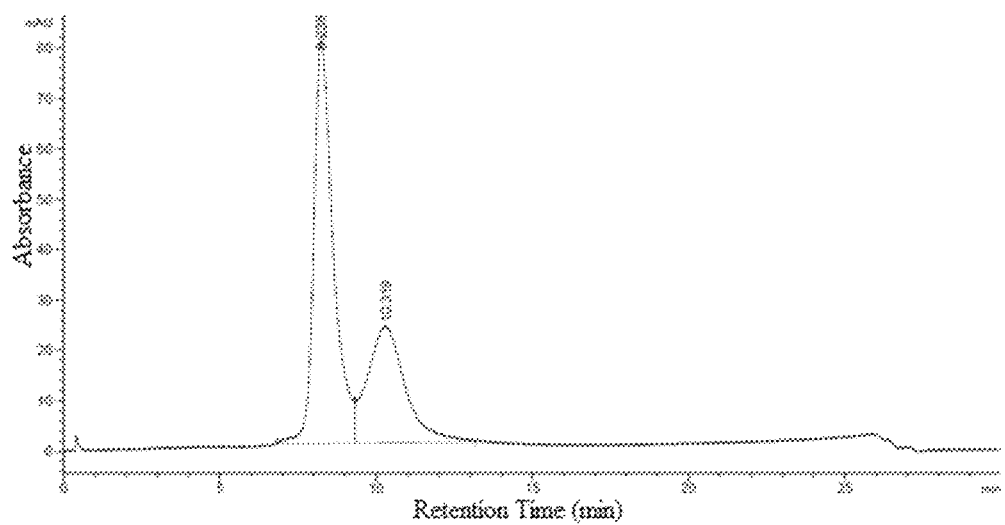
Figure 3K:
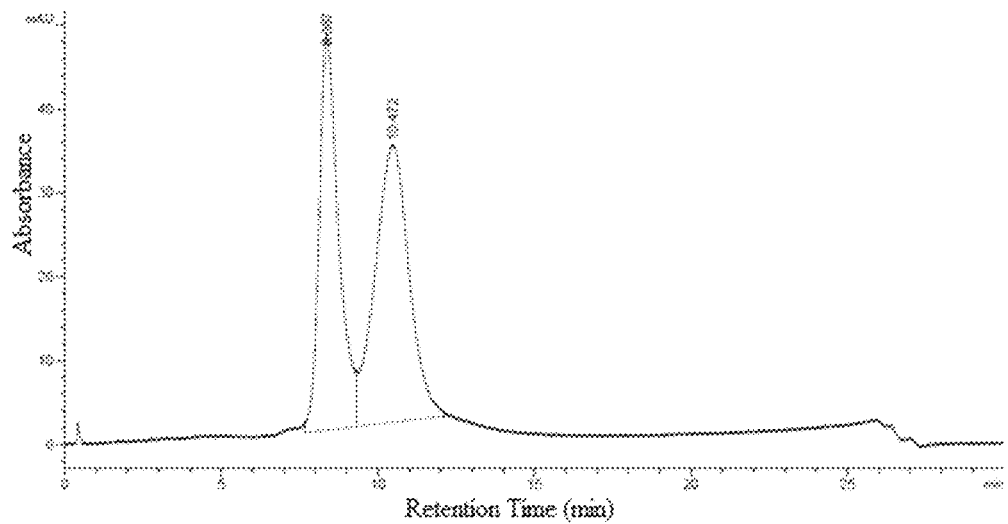
Figure 3L:
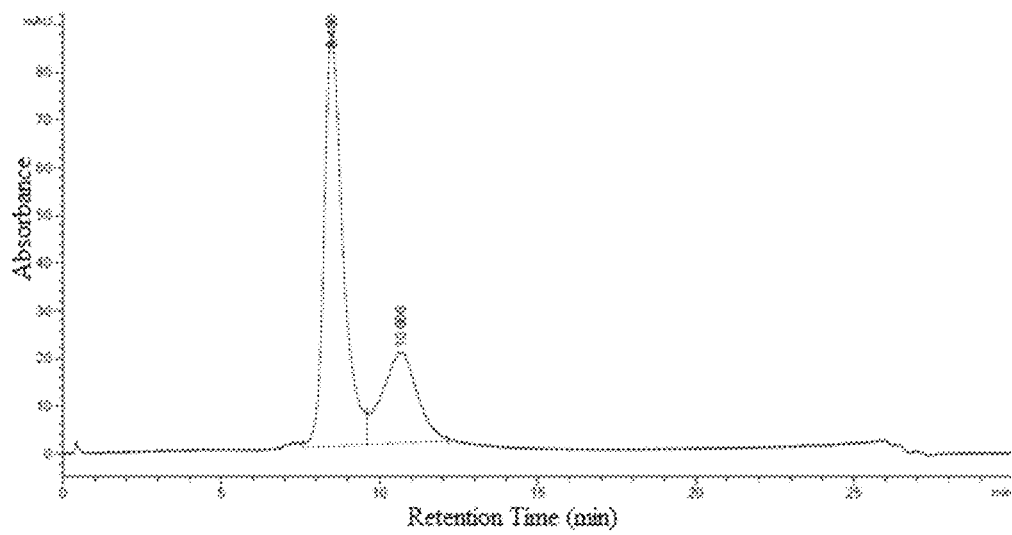
Figure 3M:
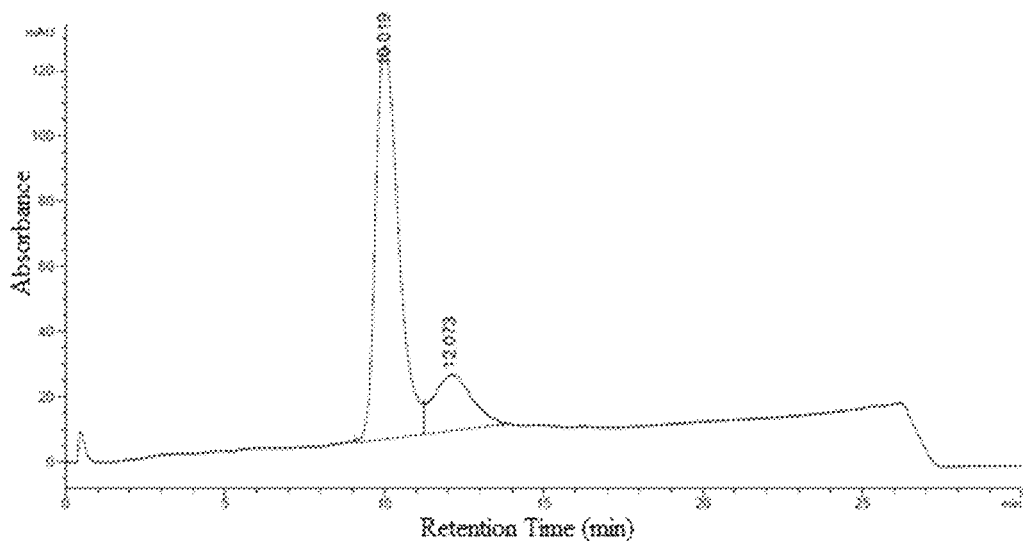

The SDS-PAGE results are shown in FIGS. 2a-2b, which shows that the main components in sample H-1-vcMMAE to H-12-vcMMAE were full antibody HHLL (full ADC) and half antibody HL (full ADC lost heavy chain interaction). The result proves that the tetramaleimide linkers of the invention can crosslink the inter chains of the reduced antibody, and thus effectively control the number of drugs per antibody (DAR).

4) Hydrophobic Interaction Chromatography (HIC) Analysis

HIC was measured on an Agilent 1100 chromatograph. TSKgel butyl-NPR column (4.6×35 mm, 2.5 μm, Tosoh Bioscience Shanghai) was applied as the immobile phase. The method was consisted of a linear gradient from 100% buffer A (50 mM potassium phosphate (pH 7.0)+1.5 M ammonium sulfate) to 100% buffer B (80% v/v 50 mM sodium phosphate (pH 7.0), 20% v/v isopropanol) over 25 minutes. The flow rate was 0.8 mL/min, the column temperature was 30° C., and the detection wavelengths were 230 and 280 nm.

HIC analysis results are shown in FIGS. 3a-3m, which show that the main components of the ADC samples (H-1-vcMMAE to H-12-vcMMAE, and P-7-vcMMAE) are DAR=2 components. The result proves that the tetramaleimide linkers of the invention could be used to effectively control the DAR and distribution of the ADC product.

Test Example 1

Determination of the Antigen Binding Ability of the ADCs of the Invention by Enzyme-Linked Immunosorbent Assay (ELISA)

Indirect ELISA was used to analyze binding ability of the antibody or antibody-drug conjugate to the corresponding antigen. The Her2 antigen was immobilized on a solid-phase support (96 well microplate) by coating to form a solid-phase antigen, and then unbound antigen was removed by washing. Serial dilutions of test antibody or antibody-drug conjugate were added, wherein specific antibody or antibody-drug conjugate bound to the antigen and formed solid-phase antigen-antibody complexes. The antibody or antibody-drug conjugate unbound to the solid-phase antigen was removed by washing. The enzyme labeled anti-antibody was added to bind to the above-formed complexes. After washing, substrate solution was added, and the optical density was read by a microplate reader at 450 nm/630 nm, based on which the curve was drawn and the $EC_{50}$ was calculated.

The binding abilities of the ADCs of the invention to Her2 antigen were listed in Table 3.

TABLE 3

The binding ability of the ADCs of the invention to Her2 antigen

| ADC | $EC_{50}$ (ng/mL) | ADC | $EC_{50}$ (ng/mL) |
|---|---|---|---|
| H | 33.5 | | |
| H-1-vcMMAE | 14.5 | H-7-vcMMAE | 34.0 |
| H-2-vcMMAE | 15.7 | H-8-vcMMAE | 28.9 |
| H-3-vcMMAE | 33.2 | H-9-vcMMAE | 25.8 |
| H-4-vcMMAE | 15.7 | H-10-vcMMAE | 36.6 |
| H-5-vcMMAE | 25.9 | H-11-vcMMAE | 38.1 |
| H-6-vcMMAE | 19.1 | H-12-vcMMAE | 33.8 |

As shown in Table 3, compared to naked antibody, the binding ability of the ADCs prepared from tetramaleimide linkers to the antigen shows no significant difference.

Test Example 2

Cell Proliferation Inhibition of the ADCs of the Invention
Cell Proliferation Assay Cell proliferation inhibition of an antibody or ADC is measured by the following method. Mammalian cells expressing tumor-associated antigens or receptor proteins (Her2 expressing breast cancer cell, SK-BR-3, was used in this assay) were seed in 96-well plate at a concentration of 8000 cells/well, and the cells were suspended in DMEM (GIBCO). The initial ADC concentration was 2 μg/mL, which was 3 times gradient diluted with DMEM containing 2% FBS (GIBCO). The initial cell culture media was removed and 200 μL of ADC was added to each well. The cells were incubated for 72 h, and the media was removed. 100 μL of CCK-8 was added, followed by incubation of 30 min. The absorption was read by a microplate reader at 450 nm/630 nm, based on which the curve was drawn and the $IC_{50}$ was calculated.

The cell proliferation inhibition result of the ADCs of the invention was listed in table 4.

TABLE 4

Cell Proliferation Inhibition Result of the ADCs of the Invention

| ADC | $IC_{50}$ (ng/mL) | ADC | $IC_{50}$ (ng/mL) |
|---|---|---|---|
| H-1-vcMMAE | 5.1 | H-7-vcMMAE | 8.8 |
| H-2-vcMMAE | 7.9 | H-8-vcMMAE | 9.1 |
| H-3-vcMMAE | 7.7 | H-9-vcMMAE | 5.1 |
| H-4-vcMMAE | 8.8 | H-10-vcMMAE | 6.3 |
| H-5-vcMMAE | 8.6 | H-11-vcMMAE | 6.1 |
| H-6-vcMMAE | 9.4 | H-12-vcMMAE | 7.4 |
| P-7-vcMMAE | 8.8 | | |

Table 4 shows that the ADCs of the invention have excellent cell proliferation inhibition activity All references mentioned in the present application are incorporated herein by reference to the same extent as if each individual reference is individually incorporated by reference. In addition, it should be understood that after reading the present invention, those skilled in the art can make various changes or modifications to the present invention, and these equivalent forms also fall within the scope defined by the appended claims of the present application.

What is claimed is:

1. An antibody-drug conjugate of formula IV:

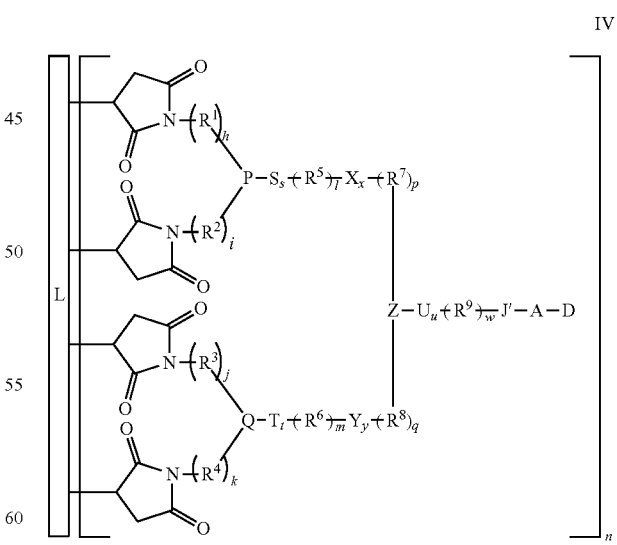

IV wherein

L is an antibody or antibody fragment;

A is optionally other linker than tetramaleimide linker, including cleavable and noncleavable linker;

D is a drug molecule;

four maleimide groups are simultaneously linked to the same antibody or antibody fragment;

P and Q are each independently selected from $CR^{10}$, N and aryl;

S and T are each independently selected from C=O and O;

X and Y are each independently selected from —C(O)N($R^{11}$)—, —N($R^{12}$)C(O)— and —O—;

Z is selected from $CR^{13}$, N and aryl;

U is selected from C=O and O;

J' is selected from C=O, O and $NR^{14}$;

h, i, j, k, l, m, p, q, s, t, x, y, u and w are each independently selected from 0 and 1;

$R^1$, $R^2$, $R^3$, $R^4$, $R^5$, $R^6$, $R^7$, $R^8$ and $R^9$ are each independently selected from $C_1$-$C_6$ alkylene, and $C_1$-$C_6$ alkylene containing O in the backbone;

$R^{10}$, $R^{11}$, $R^{12}$, $R^{13}$ and $R^{14}$ are each independently selected from H and $C_1$-$C_6$ alkyl; and n is an integer of 1 to 4.

2. An antibody-drug conjugate of formula IV according to claim 1, wherein the antibody targets cell surface receptors or tumor-related antigens.

3. An antibody-drug conjugate of formula IV according to claim 2, wherein the antibody is IgG1.

4. An antibody-drug conjugate of formula IV according to claim 3, wherein the drug is cytotoxic drug, anti-autoimmune disease drug, or anti-inflammation drug.

5. A pharmaceutical composition comprising an antibody-drug conjugate of formula IV according to claim 1 and pharmaceutically acceptable carriers.

6. A method of making an antibody-drug conjugates, comprising conjugating an antibody to a drug using a compound of formula I as a linker,

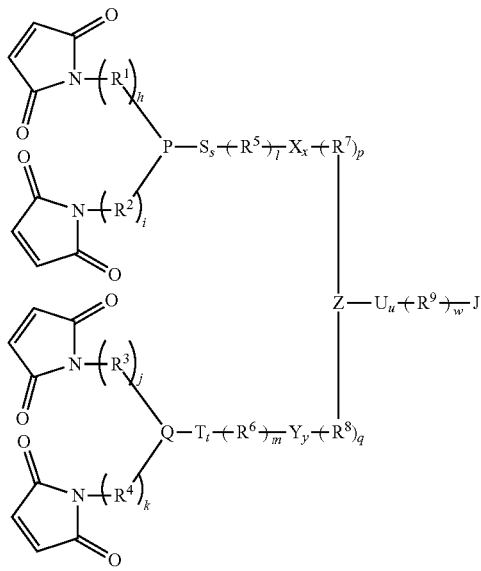

I and pharmaceutically acceptable salts thereof,
wherein

P and Q are each independently selected from $CR^{10}$, N and aryl;

S and T are each independently selected from C=O and O;

X and Y are each independently selected from —C(O)N($R^{11}$)—, —N($R^{12}$)C(O)— and —O—;

Z is selected from $CR^{13}$, N and aryl;

U is selected from C=O and O;

J is selected from —COOH, —OH and —$NHR^{14}$;

h, i, j, k, l, m, p, q, s, t, x, y, u and w are each independently selected from 0 and 1;

$R^1$, $R^2$, $R^3$, $R^4$, $R^5$, $R^6$, $R^7$, $R^8$ and $R^9$ are each independently selected from $C_1$-$C_6$ alkylene and $C_1$-$C_6$ alkylene containing O in the backbone;

$R^{10}$, $R^{11}$, $R^{12}$, $R^{13}$ and $R^{14}$ are each independently selected from H and $C_1$-$C_6$ alkyl.

7. An antibody-drug conjugate of formula IV according to claim 1 wherein A has a formula of C-$E_e$-$F_f$ or $G_g$;

wherein

C is a cleavable linker;

E and F are self-immolative linkers;

e and f are each independently selected from an integer of 0 to 5;

G is a noncleavable linker;

g is an integer of 0 to 5.

8. The method according to claim 6, wherein:

X and Y are each independently selected from —C(O)N($R^{11}$)—;

x and y are each independently selected from 0 and 1;

$R^{11}$ is selected from H and $C_1$-$C_6$ alkyl.

9. The method according to claim 6, wherein:

Z is selected from $CR^{13}$, N and $C_6$-$C_{10}$ aryl;

$R^{13}$ is selected from H and $C_1$-$C_6$ alkyl.

10. The method according to claim 6, wherein:

$R^1$, $R^2$, $R^3$ and $R^4$ are each independently selected from $C_1$-$C_6$ alkylene;

h, i, j and k are each independently selected from 0 and 1.

11. The method according to claim 6, wherein:

S and T are each independently selected from C=O and O;

$R^5$ and $R^6$ are each independently selected from $C_1$-$C_6$ alkylene;

l and m are each independently selected from 0 and 1;

s and t are each independently selected from 0 and 1.

12. The method according to claim 6, wherein:

$R^7$ and $R^8$ are each independently selected from $C_1$-$C_6$ alkylene and $C_1$-$C_6$ alkylene containing O in the backbone;

p and q are each independently selected from 0 and 1.

13. The method according to claim 6, wherein:

U is selected from C=O and O;

$R^9$ is selected from $C_1$-$C_6$ alkylene;

u and w are each independently selected from 0 and 1.

14. The method according to claim 6, wherein:

J is selected from —COOH, OH and $NH_2$.

15. The method according to claim 6, wherein the compounds are selected from:

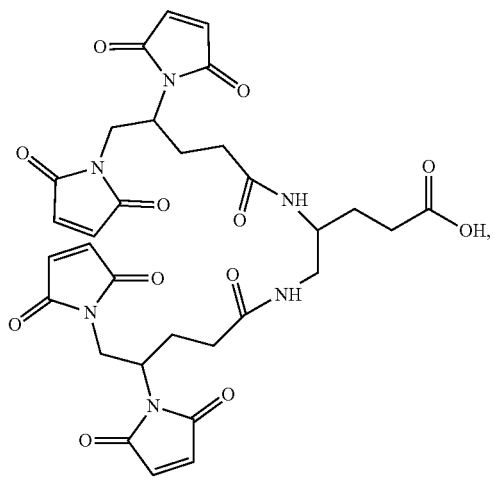
1
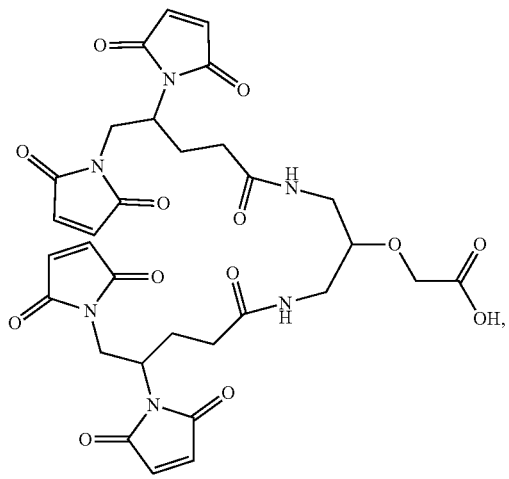
2
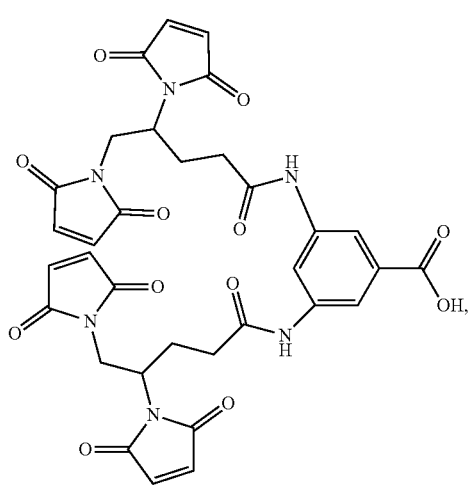
3
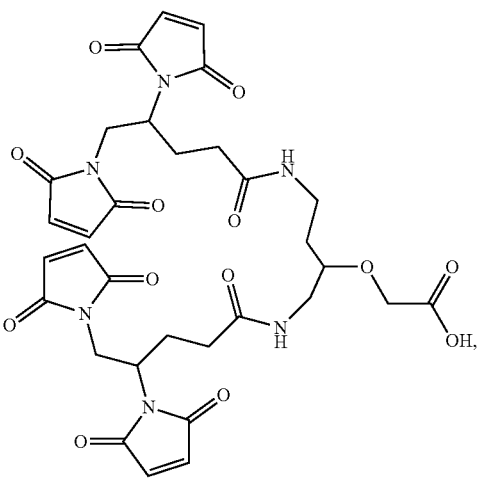
4

7
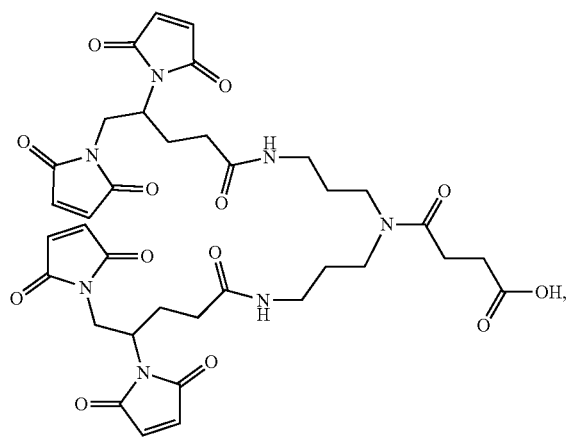
8
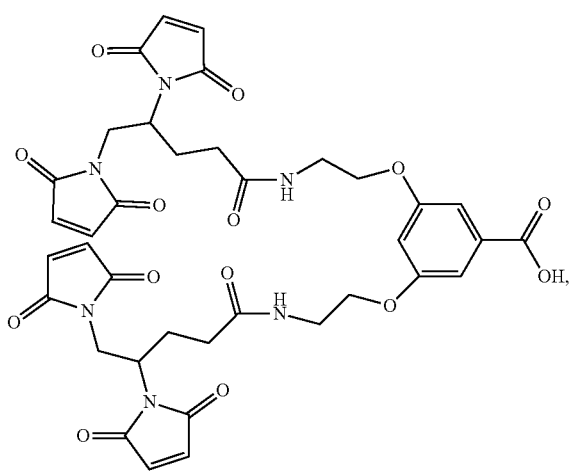
9
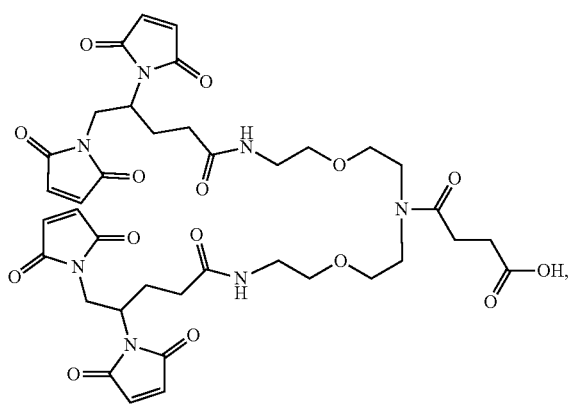
10
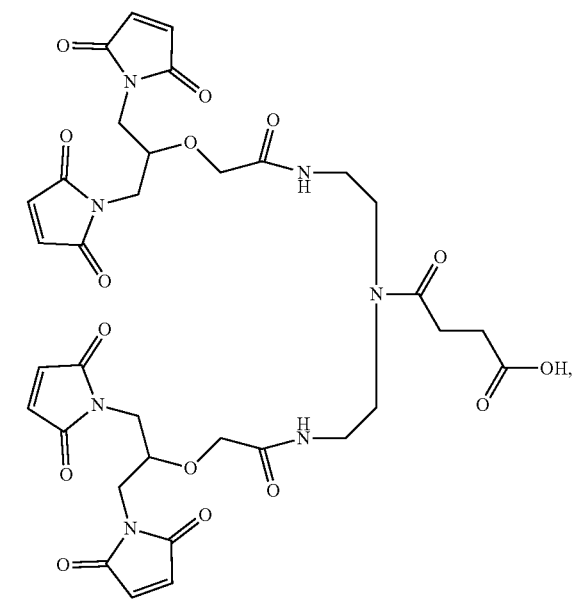
11

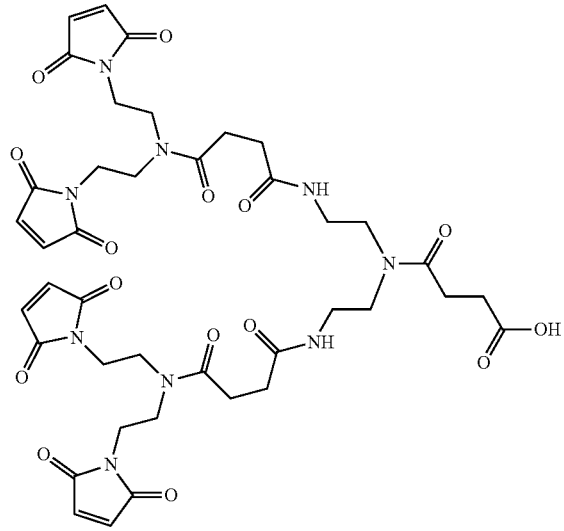
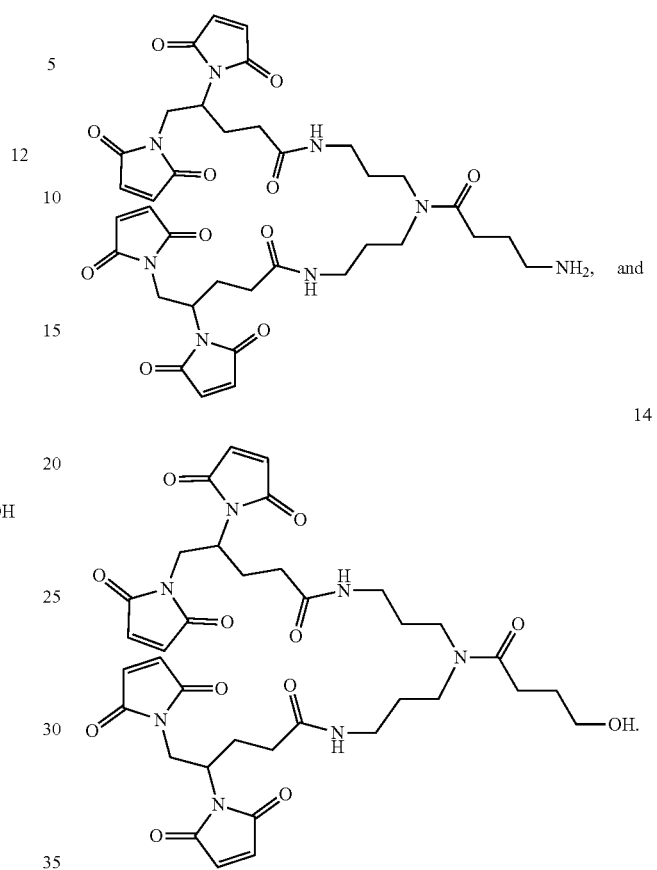
* * * * *